US011957788B2

(12) United States Patent
Radovic-Moreno et al.

(10) Patent No.: US 11,957,788 B2
(45) Date of Patent: *Apr. 16, 2024

(54) MULTIVALENT DELIVERY OF IMMUNE MODULATORS BY LIPOSOMAL SPHERICAL NUCLEIC ACIDS FOR PROPHYLACTIC OR THERAPEUTIC APPLICATIONS

(71) Applicant: Exicure Operating Company, Chicago, IL (US)

(72) Inventors: Aleksandar Filip Radovic-Moreno, Evanston, IL (US); Richard Kang, Wilmette, IL (US); Subbarao Nallagatla, Chicago, IL (US); Christopher C. Mader, Mendham, NJ (US); Sergei Gryaznov, San Mateo, CA (US)

(73) Assignee: Exicure Operating Company, Chicago, IL (US)

( * ) Notice: Subject to any disclaimer, the term of this patent is extended or adjusted under 35 U.S.C. 154(b) by 74 days.

This patent is subject to a terminal disclaimer.

(21) Appl. No.: 17/405,068

(22) Filed: Aug. 18, 2021

(65) Prior Publication Data

US 2022/0257512 A1 Aug. 18, 2022

Related U.S. Application Data

(63) Continuation of application No. 16/569,007, filed on Sep. 12, 2019, now Pat. No. 11,123,294, which is a continuation of application No. 15/315,538, filed as application No. PCT/US2015/034226 on Jun. 4, 2015, now Pat. No. 10,434,064.

(60) Provisional application No. 62/007,528, filed on Jun. 4, 2014.

(51) Int. Cl.
| | | |
|---|---|---|
| *A61K 9/127* | (2006.01) | |
| *A61K 39/00* | (2006.01) | |
| *A61K 39/02* | (2006.01) | |
| *A61K 39/12* | (2006.01) | |
| *A61K 39/35* | (2006.01) | |
| *A61K 39/385* | (2006.01) | |
| *A61K 47/69* | (2017.01) | |
| *B82Y 5/00* | (2011.01) | |

(52) U.S. Cl.
CPC ............ *A61K 9/1271* (2013.01); *A61K 39/00* (2013.01); *A61K 39/0011* (2013.01); *A61K 39/02* (2013.01); *A61K 39/12* (2013.01); *A61K 39/35* (2013.01); *A61K 39/385* (2013.01); *A61K 47/6911* (2017.08); *B82Y 5/00* (2013.01); *A61K 2039/55555* (2013.01); *A61K 2039/55561* (2013.01); *A61K 2121/00* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,289,872 A | 9/1981 | Denkewalter et al. |
| 4,469,863 A | 9/1984 | Ts'o et al. |
| 4,476,301 A | 10/1984 | Imbach et al. |
| 4,489,055 A | 12/1984 | Couvreur et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,789,737 A | 12/1988 | Miyoshi et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,958,013 A | 9/1990 | Letsinger |
| 4,981,957 A | 1/1991 | Lebleu et al. |
| 5,008,050 A | 4/1991 | Cullis et al. |
| 5,013,830 A | 5/1991 | Ohtsuka et al. |
| 5,023,243 A | 6/1991 | Tullis |
| 5,034,506 A | 7/1991 | Summerton et al. |
| 5,130,302 A | 7/1992 | Spielvogel et al. |
| 5,134,066 A | 7/1992 | Rogers et al. |
| 5,138,045 A | 8/1992 | Cook et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,214,136 A | 5/1993 | Lin et al. |
| 5,216,141 A | 6/1993 | Benner |
| 5,220,007 A | 6/1993 | Pederson et al. |

(Continued)

FOREIGN PATENT DOCUMENTS

| | | |
|---|---|---|
| AR | 070368 A2 | 3/2010 |
| AU | 2004218696 A1 | 11/2004 |

(Continued)

OTHER PUBLICATIONS

Extended European Search Report dated May 15, 2019 in connection with EP 19156455.8.
International Search Report and Written Opinion dated Oct. 13, 2015 for PCT/US2015/034226.
International Preliminary Report on Patentability dated Dec. 15, 2016 for PCT/US2015/034226.
[No Author Listed] Synthetic CpG ODNs Activate immune cells through the Toll-like receptor (TLR) Pathway. IDT Integrated DNA Technologies. Apr. 11, 2017. 3 pages.

(Continued)

*Primary Examiner* — Brian Whiteman
(74) *Attorney, Agent, or Firm* — Wolf, Greenfield & Sacks, P.C.

(57) ABSTRACT

Liposomal spherical nucleic acids that function as multivalent immune modulators are provided according to the invention. The liposomal spherical nucleic acids of the invention are useful prophylactic and therapeutic applications as well as research and diagnostic indications.

20 Claims, 15 Drawing Sheets

Specification includes a Sequence Listing.

(56) References Cited

U.S. PATENT DOCUMENTS

| | | |
|---|---|---|
| 5,229,490 A | 7/1993 | Tam |
| 5,235,033 A | 8/1993 | Summerton et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,264,618 A | 11/1993 | Felgner et al. |
| 5,276,019 A | 1/1994 | Cohen et al. |
| 5,278,302 A | 1/1994 | Caruthers et al. |
| 5,286,717 A | 2/1994 | Cohen et al. |
| 5,317,098 A | 5/1994 | Shizuya et al. |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,512,667 A | 4/1996 | Reed et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,545,730 A | 8/1996 | Urdea et al. |
| 5,547,842 A | 8/1996 | Hogan et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,810 A | 10/1996 | Weis et al. |
| 5,571,799 A | 11/1996 | Tkachuk et al. |
| 5,576,427 A | 11/1996 | Cook et al. |
| 5,578,717 A | 11/1996 | Urdea et al. |
| 5,578,718 A | 11/1996 | Cook et al. |
| 5,587,361 A | 12/1996 | Cook et al. |
| 5,587,371 A | 12/1996 | Sessler et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,646,269 A | 7/1997 | Matteucci et al. |
| 5,652,355 A | 7/1997 | Metelev et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,780,448 A | 7/1998 | Davis |
| 5,792,608 A | 8/1998 | Swaminathan et al. |
| 5,814,666 A | 9/1998 | Green et al. |
| 5,830,653 A | 11/1998 | Froehler et al. |
| 5,955,589 A | 9/1999 | Cook et al. |
| 6,005,096 A | 12/1999 | Matteucci et al. |
| 6,194,328 B1 | 2/2001 | Krieg et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,228,642 B1 | 5/2001 | Baker et al. |
| 6,239,116 B1 | 5/2001 | Krieg et al. |
| 6,271,209 B1 | 8/2001 | Smith et al. |
| 6,339,068 B1 | 1/2002 | Krieg et al. |
| 6,361,944 B1 | 3/2002 | Mirkin et al. |
| 6,406,705 B1 | 6/2002 | Davis et al. |
| 6,417,340 B1 | 7/2002 | Mirkin et al. |
| 6,429,199 B1 | 8/2002 | Krieg et al. |
| 6,495,324 B1 | 12/2002 | Mirkin et al. |
| 6,506,564 B1 | 1/2003 | Mirkin et al. |
| 6,534,062 B2 | 3/2003 | Raz et al. |
| 6,582,921 B2 | 6/2003 | Mirkin et al. |
| 6,610,308 B1 | 8/2003 | Haensler |
| 6,610,491 B2 | 8/2003 | Mirkin et al. |
| 6,656,730 B1 | 12/2003 | Manoharan |
| 6,677,122 B2 | 1/2004 | Mirkin et al. |
| 6,677,153 B2 | 1/2004 | Iversen |
| 6,682,895 B2 | 1/2004 | Mirkin et al. |
| 6,709,825 B2 | 3/2004 | Mirkin et al. |
| 6,720,147 B2 | 4/2004 | Mirkin et al. |
| 6,720,411 B2 | 4/2004 | Mirkin et al. |
| 6,750,016 B2 | 6/2004 | Mirkin et al. |
| 6,759,199 B2 | 7/2004 | Mirkin et al. |
| 6,767,702 B2 | 7/2004 | Mirkin et al. |
| 6,773,884 B2 | 8/2004 | Mirkin et al. |
| 6,777,186 B2 | 8/2004 | Mirkin et al. |
| 6,812,334 B1 | 11/2004 | Mirkin et al. |
| 6,818,753 B2 | 11/2004 | Mirkin et al. |
| 6,828,432 B2 | 12/2004 | Mirkin et al. |
| 6,849,725 B2 | 2/2005 | Junghans et al. |
| 6,861,221 B2 | 3/2005 | Mirkin et al. |
| 6,878,814 B2 | 4/2005 | Mirkin et al. |
| 7,001,616 B2 | 2/2006 | Batich et al. |
| 7,038,029 B2 | 5/2006 | Lopez |
| 7,098,320 B1 | 8/2006 | Mirkin et al. |
| 7,129,222 B2 | 10/2006 | Van Nest et al. |
| 7,176,296 B2 | 2/2007 | Agrawal et al. |
| 7,208,587 B2 | 4/2007 | Mirkin et al. |
| 7,223,741 B2 | 5/2007 | Krieg |
| 7,238,472 B2 | 7/2007 | Mirkin et al. |
| 7,250,403 B2 | 7/2007 | Van Nest et al. |
| 7,255,868 B2 | 8/2007 | Fearon et al. |
| 7,262,286 B2 | 8/2007 | Kandimalla et al. |
| 7,276,489 B2 | 10/2007 | Agrawal et al. |
| 7,332,586 B2 | 2/2008 | Franzen et al. |
| 7,354,907 B2 | 4/2008 | Agrawal et al. |
| 7,387,271 B2 | 6/2008 | Noelle et al. |

(56) References Cited

U.S. PATENT DOCUMENTS

| | | |
|---|---|---|
| 7,404,969 B2 | 7/2008 | Chen et al. |
| 7,427,405 B2 | 9/2008 | Agrawal et al. |
| 7,470,674 B2 | 12/2008 | Agrawal et al. |
| 7,514,099 B2 | 4/2009 | Chen et al. |
| 7,563,618 B2 | 7/2009 | Gryaznov et al. |
| 7,569,553 B2 | 8/2009 | Krieg |
| 7,569,554 B2 | 8/2009 | Kandimalla et al. |
| 7,615,539 B2 | 11/2009 | Uhlmann et al. |
| 7,628,990 B2 | 12/2009 | Tuck et al. |
| 7,666,674 B2 | 2/2010 | Klinman et al. |
| 7,709,617 B2 | 5/2010 | Kandimalla et al. |
| 7,713,535 B2 | 5/2010 | Agrawal et al. |
| 7,718,622 B2 | 5/2010 | Tuck et al. |
| 7,727,969 B2 | 6/2010 | Farokhzad et al. |
| 7,745,606 B2 | 6/2010 | Dina et al. |
| 7,776,834 B2 | 8/2010 | Agrawal et al. |
| 7,786,089 B2 | 8/2010 | Kandimalla et al. |
| 7,833,992 B2 | 11/2010 | Vargeese et al. |
| 7,851,453 B2 | 12/2010 | Agrawal et al. |
| 7,875,594 B2 | 1/2011 | Kandimalla et al. |
| 7,884,083 B2 | 2/2011 | Van Nest et al. |
| 7,884,197 B2 | 2/2011 | Kandimalla et al. |
| 7,960,362 B2 | 6/2011 | Kandimalla et al. |
| 7,964,578 B2 | 6/2011 | Vargeese et al. |
| 7,993,659 B2 | 8/2011 | Noelle et al. |
| 8,008,266 B2 | 8/2011 | Krieg et al. |
| 8,008,267 B2 | 8/2011 | Kandimalla et al. |
| 8,017,591 B2 | 9/2011 | Brzezicha et al. |
| 8,058,249 B2 | 11/2011 | Krieg et al. |
| 8,088,388 B2 | 1/2012 | Sokoll |
| 8,124,590 B2 | 2/2012 | Van Nest et al. |
| 8,128,944 B2 | 3/2012 | Jurk et al. |
| 8,158,768 B2 | 4/2012 | Dina et al. |
| 8,188,254 B2 | 5/2012 | Uhlmann et al. |
| 8,188,261 B2 | 5/2012 | Kandimalla et al. |
| 8,283,328 B2 | 10/2012 | Krieg et al. |
| 8,304,396 B2 | 11/2012 | Krieg et al. |
| 8,309,527 B2 | 11/2012 | Krieg et al. |
| 8,323,686 B2 | 12/2012 | Mirkin et al. |
| 8,333,980 B2 | 12/2012 | Van Nest et al. |
| 8,431,544 B1 | 4/2013 | Agrawal et al. |
| 8,470,342 B2 | 6/2013 | Klinman et al. |
| 8,586,555 B2 | 11/2013 | Fearon et al. |
| 8,846,080 B2 | 9/2014 | Biemans et al. |
| 8,853,375 B2 | 10/2014 | Kandimalla et al. |
| 8,871,732 B2 | 10/2014 | Dina et al. |
| 8,889,181 B2 | 11/2014 | Kwon |
| 8,933,046 B2 | 1/2015 | Machuy et al. |
| 8,940,310 B2 | 1/2015 | Barrat et al. |
| 8,945,590 B2 | 2/2015 | Fairman et al. |
| 8,968,746 B2 | 3/2015 | Baumhof et al. |
| 9,061,001 B2 | 6/2015 | van Drunen Littel-van den Hurk et al. |
| 9,066,978 B2 | 6/2015 | Ilyinskii et al. |
| 9,139,827 B2 | 9/2015 | Mirkin et al. |
| 9,192,667 B2 | 11/2015 | Hoves et al. |
| 9,200,287 B2 | 12/2015 | Uhlmann et al. |
| 9,212,366 B2 | 12/2015 | Wittig et al. |
| 9,216,155 B2 | 12/2015 | Thaxton et al. |
| 9,308,253 B2 | 4/2016 | Kim et al. |
| 9,364,433 B2 | 6/2016 | Andersson et al. |
| 9,421,254 B2 | 8/2016 | Berzofsky et al. |
| 9,499,815 B1 | 11/2016 | Schroff et al. |
| 9,506,056 B2 | 11/2016 | Mirkin et al. |
| 9,522,958 B2 | 12/2016 | Epstein et al. |
| 9,532,948 B2 | 1/2017 | Mirkin et al. |
| 9,549,901 B2 | 1/2017 | Shi et al. |
| 9,580,708 B2 | 2/2017 | Uhlmann et al. |
| 9,617,541 B2 | 4/2017 | Mirkin et al. |
| 9,617,547 B2 | 4/2017 | Gemba |
| 9,693,957 B2 | 7/2017 | Lin et al. |
| 9,764,031 B2 | 9/2017 | Ilyinskii et al. |
| 9,844,562 B2 | 12/2017 | Mirkin et al. |
| 9,868,955 B2 | 1/2018 | Guiducci et al. |
| 9,889,209 B2 | 2/2018 | Mirkin et al. |
| 9,901,616 B2 | 2/2018 | Dhar et al. |
| 9,907,845 B2 | 3/2018 | Reed et al. |
| 9,907,862 B2 | 3/2018 | Baumhof et al. |
| 9,919,058 B2 | 3/2018 | Klinman et al. |
| 9,950,063 B2 | 4/2018 | Reed et al. |
| 9,968,673 B2 | 5/2018 | Navarro y Garcia et al. |
| 9,976,147 B2 | 5/2018 | Kortylewski et al. |
| 9,987,355 B2 | 6/2018 | Reed et al. |
| 9,999,673 B2 | 6/2018 | Rajeev et al. |
| 10,006,032 B2 | 6/2018 | Schroff et al. |
| 10,029,016 B2 | 7/2018 | Irvine et al. |
| 10,041,074 B2 | 8/2018 | Ozsolak |
| 10,078,092 B2 | 9/2018 | Mutharasan et al. |
| 10,098,958 B2 | 10/2018 | Mirkin et al. |
| 10,144,933 B2 | 12/2018 | Gemba et al. |
| 10,149,905 B2 | 12/2018 | Gemba et al. |
| 10,155,950 B2 | 12/2018 | Munnes et al. |
| 10,182,988 B2 | 1/2019 | Mirkin et al. |
| 10,196,643 B2 | 2/2019 | Dina et al. |
| 10,208,310 B2 | 2/2019 | Mader et al. |
| 10,280,424 B2 | 5/2019 | Kleuss et al. |
| 10,322,173 B2 | 6/2019 | Gemba et al. |
| 10,328,026 B2 | 6/2019 | Thaxton et al. |
| 10,370,656 B2 | 8/2019 | Mirkin et al. |
| 10,391,116 B2 | 8/2019 | Mirkin et al. |
| 10,398,784 B2 | 9/2019 | Mirkin et al. |
| 10,413,565 B2 | 9/2019 | Plebanek et al. |
| 10,434,064 B2 | 10/2019 | Radovic-Moreno et al. |
| 10,456,463 B2 | 10/2019 | Davis et al. |
| 10,517,927 B2 | 12/2019 | Thaxton et al. |
| 10,568,898 B2 | 2/2020 | Thaxton et al. |
| 10,619,210 B2 | 4/2020 | Ahuja et al. |
| 10,653,780 B2 | 5/2020 | Hope et al. |
| 10,682,400 B2 | 6/2020 | Ali et al. |
| 10,704,043 B2 | 7/2020 | Daniel et al. |
| 10,760,080 B2 | 9/2020 | Mader et al. |
| 10,792,251 B2 | 10/2020 | Mirkin et al. |
| 10,837,018 B2 | 11/2020 | Radovic-Moreno et al. |
| 10,851,379 B2 | 12/2020 | Munnes et al. |
| 10,894,963 B2 | 1/2021 | Radovic-Moreno et al. |
| 11,123,294 B2 | 9/2021 | Radovic-Moreno et al. |
| 2002/0156033 A1 | 10/2002 | Bratzler et al. |
| 2002/0172711 A1 | 11/2002 | Martin et al. |
| 2002/0172953 A1 | 11/2002 | Mirkin et al. |
| 2002/0197269 A1 | 12/2002 | Lingnau et al. |
| 2003/0026782 A1 | 2/2003 | Krieg |
| 2003/0050261 A1 | 3/2003 | Krieg et al. |
| 2003/0091599 A1 | 5/2003 | Davis et al. |
| 2003/0104044 A1 | 6/2003 | Semple et al. |
| 2003/0129251 A1 | 7/2003 | Van Nest et al. |
| 2003/0133988 A1 | 7/2003 | Fearon et al. |
| 2003/0138413 A1 | 7/2003 | Vicari et al. |
| 2003/0147966 A1 | 8/2003 | Franzen et al. |
| 2003/0170162 A1 | 9/2003 | Nayfeh et al. |
| 2003/0181412 A1 | 9/2003 | Erikson |
| 2003/0212026 A1 | 11/2003 | Krieg et al. |
| 2004/0014956 A1 | 1/2004 | Woolf et al. |
| 2004/0053384 A1 | 3/2004 | Sligar et al. |
| 2004/0087534 A1 | 5/2004 | Krieg et al. |
| 2004/0092468 A1 | 5/2004 | Schwartz |
| 2004/0131628 A1 | 7/2004 | Bratzler et al. |
| 2004/0143112 A1 | 7/2004 | Krieg et al. |
| 2004/0170560 A1 | 9/2004 | Fossheim et al. |
| 2004/0247680 A1 | 12/2004 | Farokhzad et al. |
| 2004/0248099 A1 | 12/2004 | Goppelt et al. |
| 2004/0266719 A1 | 12/2004 | McCluskie et al. |
| 2005/0009773 A1 | 1/2005 | Kandimalla et al. |
| 2005/0089890 A1 | 4/2005 | Cubicciotti |
| 2005/0090671 A1 | 4/2005 | Chang et al. |
| 2005/0096263 A1 | 5/2005 | Keay et al. |
| 2005/0130911 A1 | 6/2005 | Uhlmann et al. |
| 2005/0136258 A1 | 6/2005 | Nie et al. |
| 2005/0169888 A1 | 8/2005 | Hartmann et al. |
| 2006/0002949 A1 | 1/2006 | Glenn et al. |
| 2006/0003962 A1 | 1/2006 | Ahluwalia et al. |
| 2006/0014713 A1 | 1/2006 | Agrawal et al. |
| 2006/0019916 A1 | 1/2006 | Krieg et al. |
| 2006/0019917 A1 | 1/2006 | Guerciolini et al. |
| 2006/0083781 A1 | 4/2006 | Shastri et al. |

(56) References Cited

U.S. PATENT DOCUMENTS

| | | |
|---|---|---|
| 2006/0105343 A1 | 5/2006 | Zetter et al. |
| 2006/0140875 A1 | 6/2006 | Krieg et al. |
| 2006/0147456 A1 | 7/2006 | Lebecque et al. |
| 2006/0188560 A1 | 8/2006 | Cheresh et al. |
| 2006/0251623 A1 | 11/2006 | Bachmann et al. |
| 2006/0252037 A1 | 11/2006 | Kolesnick et al. |
| 2006/0275371 A1 | 12/2006 | Dai et al. |
| 2006/0292174 A1 | 12/2006 | de los Rios et al. |
| 2007/0066554 A1 | 3/2007 | Krieg et al. |
| 2007/0093439 A1 | 4/2007 | Agrawal et al. |
| 2007/0148251 A1 | 6/2007 | Hossainy et al. |
| 2007/0184068 A1 | 8/2007 | Renner et al. |
| 2007/0218501 A1 | 9/2007 | Fogelman et al. |
| 2007/0243132 A1 | 10/2007 | Russell-Jones et al. |
| 2007/0243196 A1 | 10/2007 | Bruck et al. |
| 2007/0249555 A1 | 10/2007 | Barbaras et al. |
| 2007/0298257 A1 | 12/2007 | Ludwig et al. |
| 2008/0003232 A1 | 1/2008 | Wang et al. |
| 2008/0045473 A1 | 2/2008 | Uhlmann et al. |
| 2008/0057128 A1 | 3/2008 | Li et al. |
| 2008/0124366 A1 | 5/2008 | Ohlfest et al. |
| 2008/0175893 A1 | 7/2008 | Huang et al. |
| 2008/0181928 A1 | 7/2008 | Hakimi-Mehr et al. |
| 2008/0194463 A1 | 8/2008 | Weller et al. |
| 2008/0206265 A1 | 8/2008 | Kandimalla et al. |
| 2008/0213177 A1 | 9/2008 | Rademacher et al. |
| 2008/0220072 A1 | 9/2008 | Unger et al. |
| 2008/0274454 A1 | 11/2008 | Mirkin et al. |
| 2008/0279785 A1 | 11/2008 | Kandimalla et al. |
| 2008/0306016 A1 | 12/2008 | Mirkin et al. |
| 2008/0311182 A1 | 12/2008 | Ferrari et al. |
| 2009/0018028 A1 | 1/2009 | Lindsay et al. |
| 2009/0053169 A1 | 2/2009 | Castillo et al. |
| 2009/0081157 A1 | 3/2009 | Kornbluth et al. |
| 2009/0081244 A1 | 3/2009 | Glenn et al. |
| 2009/0148384 A1 | 6/2009 | Fischer et al. |
| 2009/0155173 A1 | 6/2009 | Scherman et al. |
| 2009/0191185 A1 | 7/2009 | Selander |
| 2009/0191188 A1 | 7/2009 | Krieg et al. |
| 2009/0209629 A1 | 8/2009 | Mirkin et al. |
| 2009/0286853 A1 | 11/2009 | Gryaznov et al. |
| 2009/0317802 A1 | 12/2009 | Bhatia et al. |
| 2009/0322327 A1 | 12/2009 | Gao |
| 2009/0324706 A1 | 12/2009 | Mirkin et al. |
| 2010/0003287 A1 | 1/2010 | Mills et al. |
| 2010/0003317 A1 | 1/2010 | Akinc et al. |
| 2010/0092486 A1 | 4/2010 | Kandimalla et al. |
| 2010/0111968 A1 | 5/2010 | Branigan et al. |
| 2010/0136682 A1 | 6/2010 | Mirkin et al. |
| 2010/0144848 A1 | 6/2010 | Vogel et al. |
| 2010/0166842 A1 | 7/2010 | Lu et al. |
| 2010/0183634 A1 | 7/2010 | Luo et al. |
| 2010/0184844 A1 | 7/2010 | Mirkin et al. |
| 2010/0203142 A1 | 8/2010 | Zhang et al. |
| 2010/0233141 A1 | 9/2010 | Polach et al. |
| 2010/0233270 A1 | 9/2010 | Mirkin et al. |
| 2010/0267814 A1 | 10/2010 | Bennett et al. |
| 2010/0303803 A1 | 12/2010 | Schroff et al. |
| 2011/0020242 A1 | 1/2011 | Zheng et al. |
| 2011/0021334 A1 | 1/2011 | Maier |
| 2011/0052680 A1 | 3/2011 | Hendrickson et al. |
| 2011/0052697 A1 | 3/2011 | Farokhzad et al. |
| 2011/0111974 A1 | 5/2011 | Mirkin et al. |
| 2011/0158937 A1 | 6/2011 | Kandimalla et al. |
| 2011/0201594 A1 | 8/2011 | Murthi et al. |
| 2011/0201672 A1 | 8/2011 | Krieg et al. |
| 2011/0223257 A1 | 9/2011 | Zhao et al. |
| 2011/0229529 A1 | 9/2011 | Irvine et al. |
| 2011/0237435 A1 | 9/2011 | Ryan |
| 2011/0244026 A1 | 10/2011 | Guild et al. |
| 2011/0256224 A1 | 10/2011 | Sigalov |
| 2011/0262347 A1 | 10/2011 | Ruoslahti et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2011/0305734 A1 | 12/2011 | Edelson et al. |
| 2012/0082616 A1 | 4/2012 | Trawick et al. |
| 2012/0093804 A1 | 4/2012 | Schroff et al. |
| 2012/0093914 A1 | 4/2012 | Schubert |
| 2012/0107303 A1 | 5/2012 | Kandimalla et al. |
| 2012/0149843 A1 | 6/2012 | Chien et al. |
| 2012/0244230 A1 | 9/2012 | Mirkin et al. |
| 2012/0258126 A1 | 10/2012 | Scholler et al. |
| 2012/0282186 A1 | 11/2012 | Mirkin et al. |
| 2012/0301499 A1 | 11/2012 | Bachmann et al. |
| 2013/0004520 A1 | 1/2013 | Andersson et al. |
| 2013/0028857 A1 | 1/2013 | Gao et al. |
| 2013/0034599 A1 | 2/2013 | Thaxton et al. |
| 2013/0071403 A1 | 3/2013 | Rolland et al. |
| 2013/0089614 A1 | 4/2013 | Zhang et al. |
| 2013/0095039 A1 | 4/2013 | Lu et al. |
| 2013/0101512 A1 | 4/2013 | Mirkin et al. |
| 2013/0123333 A1 | 5/2013 | Mirkin et al. |
| 2013/0149374 A1 | 6/2013 | Lee et al. |
| 2013/0177625 A1 | 7/2013 | Kim et al. |
| 2013/0178611 A1 | 7/2013 | Seya et al. |
| 2013/0196951 A1 | 8/2013 | Schoenfisch et al. |
| 2013/0252852 A1 | 9/2013 | Pfeiffer et al. |
| 2013/0287814 A1 | 10/2013 | Schroff et al. |
| 2013/0295129 A1 | 11/2013 | Irvine et al. |
| 2013/0315831 A1 | 11/2013 | Shi et al. |
| 2014/0005258 A1 | 1/2014 | Mirkin et al. |
| 2014/0010830 A1 | 1/2014 | Schroff et al. |
| 2014/0065425 A1 | 3/2014 | Bogdanov |
| 2014/0199379 A1 | 7/2014 | Tartour et al. |
| 2014/0227327 A1 | 8/2014 | Bencherif et al. |
| 2014/0294927 A1 | 10/2014 | Thaxton et al. |
| 2015/0080320 A1 | 3/2015 | Desai |
| 2015/0086985 A1 | 3/2015 | Giljohann et al. |
| 2015/0104501 A1 | 4/2015 | Um et al. |
| 2015/0118264 A1 | 4/2015 | Baumhof et al. |
| 2016/0186178 A1 | 6/2016 | Radovic-Moreno et al. |
| 2016/0194642 A1 | 7/2016 | Gryaznov et al. |
| 2016/0237429 A1 | 8/2016 | Cubillos-Ruiz et al. |
| 2016/0274134 A1 | 9/2016 | Mutharasan et al. |
| 2016/0310425 A1 | 10/2016 | Mirkin et al. |
| 2016/0339090 A1 | 11/2016 | Hacohen et al. |
| 2016/0348114 A1 | 12/2016 | Kleuss et al. |
| 2016/0375115 A1 | 12/2016 | Binder et al. |
| 2017/0042920 A1 | 2/2017 | Bantia |
| 2017/0130231 A1 | 5/2017 | Chae et al. |
| 2017/0175121 A1 | 6/2017 | Gryaznov |
| 2017/0240960 A1 | 8/2017 | Giljohann et al. |
| 2017/0306331 A1 | 10/2017 | Mader et al. |
| 2018/0042848 A1 | 2/2018 | Gryaznov et al. |
| 2018/0043023 A1 | 2/2018 | Ilyinskii et al. |
| 2018/0214376 A1 | 8/2018 | Giljohann |
| 2019/0142739 A1 | 5/2019 | Patel et al. |
| 2020/0030440 A1 | 1/2020 | Bazmorelli et al. |
| 2020/0069587 A1 | 3/2020 | Radovic-Moreno et al. |
| 2020/0069596 A1 | 3/2020 | Wagner |
| 2020/0188521 A1 | 6/2020 | Kang et al. |
| 2020/0248183 A1 | 8/2020 | Nallagatla et al. |
| 2020/0255837 A9 | 8/2020 | Anderson et al. |
| 2020/0297867 A1 | 9/2020 | Kang et al. |
| 2020/0308579 A1 | 10/2020 | Kang |
| 2020/0339989 A1 | 10/2020 | Daniel et al. |
| 2020/0339996 A1 | 10/2020 | Mader et al. |
| 2021/0002640 A1 | 1/2021 | Kang et al. |

FOREIGN PATENT DOCUMENTS

| | | |
|---|---|---|
| CN | 1357042 A | 7/2002 |
| CN | 1474831 A | 2/2004 |
| CN | 101180400 A | 5/2008 |
| CN | 102036652 A | 4/2011 |
| CN | 102165061 A | 8/2011 |
| CN | 103212089 A | 7/2013 |
| EP | 1 251 872 A1 | 10/2002 |
| EP | 1 221 955 B1 | 9/2005 |
| EP | 1628531 A2 | 3/2006 |
| EP | 1648913 A2 | 4/2006 |
| EP | 1768699 A1 | 4/2007 |
| EP | 1 700 603 A3 | 6/2007 |

(56) References Cited

FOREIGN PATENT DOCUMENTS

| | | |
|---|---|---|
| EP | 1802757 A2 | 7/2007 |
| EP | 1 889 911 A2 | 2/2008 |
| EP | 1350262 B1 | 6/2008 |
| EP | 1991678 A2 | 11/2008 |
| EP | 2162117 A2 | 3/2010 |
| EP | 1408110 B1 | 6/2011 |
| EP | 2391718 A2 | 12/2011 |
| EP | 2399608 A1 | 12/2011 |
| EP | 1807094 B1 | 1/2012 |
| EP | 2563384 A2 | 3/2013 |
| EP | 2656858 A1 | 10/2013 |
| EP | 2874651 A1 | 5/2015 |
| EP | 2759306 B1 | 4/2016 |
| EP | 2 360 252 B1 | 2/2017 |
| EP | 3136858 A1 | 3/2017 |
| EP | 3137105 A2 | 3/2017 |
| JP | 2004-315433 A | 11/2004 |
| JP | 2011-507807 A | 3/2011 |
| JP | 2011-518826 A | 6/2011 |
| JP | 2014-503475 A | 2/2014 |
| JP | 2014-528955 A | 10/2014 |
| KR | 2011/0039798 A | 4/2011 |
| WO | WO 1989/002439 A1 | 3/1989 |
| WO | WO 1992/021330 A1 | 12/1992 |
| WO | WO 1993/007883 A1 | 4/1993 |
| WO | WO 1993/021528 A1 | 10/1993 |
| WO | WO 1994/001550 A1 | 1/1994 |
| WO | WO 1995/006731 A2 | 3/1995 |
| WO | WO 1996/034876 A1 | 11/1996 |
| WO | WO 1997/012896 A1 | 4/1997 |
| WO | WO 97/48715 A1 | 12/1997 |
| WO | WO 1998/004740 A1 | 2/1998 |
| WO | WO 1998/018810 A1 | 5/1998 |
| WO | WO 1998/039352 A1 | 9/1998 |
| WO | WO 1999/014226 A2 | 3/1999 |
| WO | WO 2000/020645 A1 | 4/2000 |
| WO | WO 2000/042188 A2 | 7/2000 |
| WO | WO 2001/000876 A1 | 1/2001 |
| WO | WO 2001/003709 A1 | 1/2001 |
| WO | WO 2001/022990 A2 | 4/2001 |
| WO | WO 2001/049869 A1 | 7/2001 |
| WO | WO 2001/051665 A2 | 7/2001 |
| WO | WO 2001/073123 A2 | 10/2001 |
| WO | WO 2002/044321 A2 | 6/2002 |
| WO | WO 2002/096262 A2 | 12/2002 |
| WO | WO 2003/008539 A2 | 1/2003 |
| WO | WO 2003/030941 A1 | 4/2003 |
| WO | WO 2003/051278 A2 | 6/2003 |
| WO | WO 2003/086280 A2 | 10/2003 |
| WO | WO 2003/101386 A1 | 12/2003 |
| WO | WO 2004/047870 A1 | 6/2004 |
| WO | WO 2005/030259 A2 | 4/2005 |
| WO | WO 2005/063201 A2 | 7/2005 |
| WO | WO 2005/063288 A1 | 7/2005 |
| WO | WO 2005/116226 A2 | 12/2005 |
| WO | WO 2006/012695 A1 | 2/2006 |
| WO | WO 2006/015560 A1 | 2/2006 |
| WO | WO 2006/080946 A2 | 8/2006 |
| WO | WO 2006/088833 A2 | 8/2006 |
| WO | WO 2006/099445 A2 | 9/2006 |
| WO | WO 2006/110350 A2 | 10/2006 |
| WO | WO 2006/110350 A3 | 10/2006 |
| WO | WO 2006/128121 A2 | 11/2006 |
| WO | WO 2006/138145 A1 | 12/2006 |
| WO | WO 2007/008463 A2 | 1/2007 |
| WO | WO 2006/108405 A3 | 2/2007 |
| WO | WO 2007/047455 A2 | 4/2007 |
| WO | WO 2007/055682 A2 | 5/2007 |
| WO | WO 2007/055704 A2 | 5/2007 |
| WO | WO 2007/064857 A2 | 6/2007 |
| WO | WO 2007/089607 A2 | 8/2007 |
| WO | WO 2007/096134 A1 | 8/2007 |
| WO | WO 2007/106683 A2 | 9/2007 |
| WO | WO 2008/014979 A2 | 2/2008 |
| WO | WO 2008/042156 A1 | 4/2008 |
| WO | WO 2008/097328 A2 | 8/2008 |
| WO | WO 2008/098248 A2 | 8/2008 |
| WO | WO 2008/127789 A2 | 10/2008 |
| WO | WO 2009/012786 A2 | 1/2009 |
| WO | WO 2009/061515 A1 | 5/2009 |
| WO | WO 2009/073984 A1 | 6/2009 |
| WO | WO 2009/105260 A2 | 8/2009 |
| WO | WO 2009/131704 A2 | 10/2009 |
| WO | WO 2009/131931 A1 | 10/2009 |
| WO | WO 2009/133378 A2 | 11/2009 |
| WO | WO 2009/120887 A3 | 12/2009 |
| WO | WO 2010/017152 A2 | 2/2010 |
| WO | WO 2010/017154 A2 | 2/2010 |
| WO | WO 2010/060110 A1 | 5/2010 |
| WO | WO 2010/085959 A1 | 8/2010 |
| WO | WO 2010/088395 A2 | 8/2010 |
| WO | WO 2010/091293 A1 | 8/2010 |
| WO | WO 2010/105209 A1 | 9/2010 |
| WO | WO 2010/120420 A2 | 10/2010 |
| WO | WO 2011/017456 A2 | 2/2011 |
| WO | WO 2011/017690 A2 | 2/2011 |
| WO | WO 2010/147387 A3 | 5/2011 |
| WO | WO 2011/053940 A2 | 5/2011 |
| WO | WO 2011/072133 A1 | 6/2011 |
| WO | WO 2011/079290 A2 | 6/2011 |
| WO | WO 2011/091065 A2 | 7/2011 |
| WO | WO 2011/113054 A2 | 9/2011 |
| WO | WO 2011/143608 A1 | 11/2011 |
| WO | WO 2012/006634 A2 | 1/2012 |
| WO | WO 2012/022948 A1 | 2/2012 |
| WO | WO 2012/055933 A1 | 5/2012 |
| WO | WO 2012/068470 A2 | 5/2012 |
| WO | WO 2012/084991 A1 | 6/2012 |
| WO | WO 2012/097177 A2 | 7/2012 |
| WO | WO 2013/012628 A2 | 1/2013 |
| WO | WO 2013/049941 A1 | 4/2013 |
| WO | WO 2013/098813 A1 | 7/2013 |
| WO | WO 2013/151771 A1 | 10/2013 |
| WO | WO 2013/177419 A1 | 11/2013 |
| WO | WO 2014/012479 A1 | 1/2014 |
| WO | WO 2014/025795 A1 | 2/2014 |
| WO | WO 2014/052188 A1 | 4/2014 |
| WO | WO 2014/123935 A1 | 8/2014 |
| WO | WO 2014/169264 A2 | 10/2014 |
| WO | WO 2014/201245 A1 | 12/2014 |
| WO | WO 2015/013673 A1 | 1/2015 |
| WO | WO 2015/013675 A1 | 1/2015 |
| WO | WO 2015/153975 A1 | 10/2015 |
| WO | WO 2015/168379 A2 | 11/2015 |
| WO | WO 2015/187966 A1 | 12/2015 |
| WO | WO 2015/195628 A2 | 12/2015 |
| WO | WO 2016/057549 A1 | 4/2016 |
| WO | WO 2016/115320 A1 | 7/2016 |
| WO | WO 2016/134104 A1 | 8/2016 |
| WO | WO 2017/011662 A1 | 1/2017 |
| WO | WO 2017/035278 A1 | 3/2017 |
| WO | WO 2017/136467 A1 | 8/2017 |
| WO | WO 2017/184427 A1 | 10/2017 |
| WO | WO 2017/193081 A1 | 11/2017 |
| WO | WO 2017/193084 A1 | 11/2017 |
| WO | WO 2017/193087 A1 | 11/2017 |
| WO | WO 2018/053508 A1 | 3/2018 |
| WO | WO 2019/168558 A1 | 9/2019 |
| WO | WO 2020/168005 A1 | 8/2020 |
| WO | WO 2020/219985 A1 | 10/2020 |

OTHER PUBLICATIONS

[No Author Listed] Modern Pharmaceutical Design. 2006. Chapter 5. p. 273. English language summary. 2 pages.

Acton et al., Identification of scavenger receptor SR-BI as a high density lipoprotein receptor. Science. Jan. 26, 1996;271(5248):518-20.

Agbasi-Porter et al., Transcription inhibition using oligonucleotide-modified gold nanoparticles, Bioconjugate Chem., 17(5):1178-83 (2006).

Agrawal et al., Antisence therapeutics: Is it as simple as complementary base recognition? Mol. Med. Today. 2000; 6: 72-81.

(56) References Cited

OTHER PUBLICATIONS

Aissaoui et al., Efficient topical delivery of plasmid DNA to lung in vivo mediated by putative triqqered, PEGylated pDNA nanoparticles, J. Control Release. 154:275-84 (2011).
Akbarzadeh et al., Liposome: classification, preparation, and applications, Nanoscale Res Lett. Feb. 22, 2013;8(1):102. doi: 10.1186/1556-276X-8-102.
Akhter et al., Gold nanoparticles in theranostic oncology: current state-of-the-art. Expert Opin Drug Deliv. Oct. 2012;9(10):1225-43. Epub Aug. 16, 2012.
Alemdaroglu et al., DNA Block Copolymer Micelles—A Combinatorial Tool for Cancer Nanotechnology. Advanced Materials. Mar. 2008;20(5)899-902. https://doi.org/10.1002/adma.200700866l.
Ali et al., Vaccines Combined with Immune Checkpoint Antibodies Promote Cytotoxic T-cell Activity and Tumor Eradication. Cancer Immunol Res. Feb. 2016;4(2):95-100. doi: 10.1158/2326-6066.CIR-14/0126. Epub Dec. 15, 2015.
Altieri, Survivin, versatile modulation of cell division and apoptosis in cancer. Oncogene 2003; 22: 8581- 9.
Andrews et al., Conjugation of Lipid and CpG-Containing Oligonucleotide Yields an Efficient Method for Liposome Incorporation. Bioconjugate Chem. 2011;22:1279-1286.
Anton et al., Design and production of nanoparticles formulated from nano-emulsion templates—a review. J. Control Release. 2008; 128(3):185-99.
Asthana et al., Mannosylated chitosan nanoparticles for delivery of antisense oligonucleotides for macrophage targeting. Biomed Res Int. 2014;2014:526391. doi: 10.1155/2014/526391. Epub Jun. 26, 2014.
Bae et al., Oil-encapsulating PEO-PPO-PEO/PEG shell cross-linked nanocapsules for target-specific delivery of paclitaxel, Biomacromolecules. 8:650-6 (2007).
Bae et al., Targeted drug delivery to tumors: myths, reality and possibility. J Control Release. Aug. 10, 2011;153(3):198-205. doi: 10.1016/j.jconrel.2011.06.001. Epub Jun. 6, 2011.
Ballas et al., Induction of NK activity in murine and human cells by CpG motifs in oligodeoxynucleotides and bacterial DNA. J Immunol. Sep. 1, 1996;157(5):1840-5.
Banchelli, M. et al., "Phospholipid Membranes Decorated by Cholesterol-Based Oligonucleotides as Soft Hybrid Nanostructures," J. Phys. Chem., 2008, 112 (35), 10942-10952.
Banerjee et al., Poly(ethylene glycol)-Prodrug Conjugates: Concept, Design, and Applications, J.; Druo De/iv. 2012:103973 (2012).
Banga et al., Drug-loaded Polymeric Spherical Nucleic Acids: Enhancing Colloidal Stability and Cellular Uptake of Polymeric Nanoparticles through DNA Surface-functionalization. Biomacromol. Feb. 13, 2017;18(2):483-9. doi:10.1021/acs.biomac.6b01563.
Banga et al., Liposomal spherical nucleic acids. J Am Chem Soc. Jul. 16, 2014;136(28):9866-9. doi: 10.1021/ja504845f. Epub Jul. 1, 2014.
Bardeesy et al., Pancreatic cancer biology and genetics, Nat. Rev. Cancer. 2002;2(12):897-909.
Barrat et al., Nucleic acids of mammalian origin can act as endogenous ligands for Toll-like receptors and may promote systemic lupus erythematosus. J Exp Med. Oct. 17, 2005;202(8):1131-9.
Berton et al., Highly loaded nanoparticulate carrier using an hydrophobic antisense oligonucleotide complex. Eur. J. Pharma. Sci. 1999;9:163-70.
Bhattarai et al., "Enhanced Gene and siRNA Delivery by Polycation-Modified Mesoporous Silica Nanoparticles Loaded with Chloroquine," Pharm. Res., 2010, 27, 2556-2568.
Birck et al., Mutation and allelic loss of the PTEN/MMAC1 gene in primary and metastatic melanoma biopsies. J. Invest. Dermatol. 114: 277-80.
Bisht et al., Polymeric nanoparticle-encapsulated curcumin ("nanocurcumin"): a novel strategy for human cancer therapy. J. Nanobiotechnology. 2007;5:3. 18 pages.
Bitounis et al., Optimizing Druggability through Liposomal Formulations: New Approaches to an Old Concept. ISRN Pharm. 2012;2012:738432. doi: 10.5402/2012/738432. Epub Feb. 9, 2012.

Bode et al. CpG DNA as a vaccine adjuvant. Expert Rev Vaccines. Apr. 2011;10(4):499-511. doi: 10.1586/erv.10.174.
Boudreault et al., Nanoscale tools to selectively destroy cancer cells. Chem Commun. May 14, 2008;(18):2118-20. doi: 10.1039/b800528a. Epub Apr. 7, 2008.
Bozzuto et al., Liposomes as nanomedical devices. Int J Nanomedicine. Feb. 2, 2015;10:975- 99. doi: 10.2147/IJN.S68861.
Bratu et al., Visualizing the distribution and transport of mRNAs in living cells. Proc. Natl. Acad. Sci. USA. 2003;100: 13308-13.
Briley et al., In Nanomaterials for Biomedicine; American Chemical Society. 2012;1119:1-20.
Brown et al., Surface treatment of the hydrophobic drug danazol to improve drug dissolution. Int. J. Pharmaceutics. 1998;165:227-37.
Bunge et al., Lipophilic Oligonucleotides Spontaneously Insert into Lipid Membranes, Bind Complementary DNA Strands, and Sequester into Lipid-Disordered Domains, Langmuir 2007, vol. 23, No. 8, pp. 4455-4464.
Burgess, Liposome preparation—Avanti® Polar Lipids. Sigma-Aldrich. 1998. 3 pages.
Cao et al., Reversible Cell-Specific Drug Delivery with Aptamer-Functionalized Liposomes, Anqew. Chem. Int. Ed. 2009;48:6494-8.
Capaccioli et al., Cationic lipids improve antisense oligonucleotide uptake and prevent degradation in cultured cells and inhuman serum. Biochem. Biophys. Res. Commun. 1993;197(2): 818-25.
Castoldi et al., A sensitive array for micro RNA expression profiling (miChip) based on locked nucleic acids (LNA). RNA. 2006;12: 913-20.
Cha et al., Hepatocellular carcinoma: current management. Curr. Probl. Surg. 2010;47(1):10-67.
Chandaroy et al., Temperature-controlled content release from liposomes encapsulating Pluronic F127. J Control Release. Sep. 11, 2001;76(1-2):27-37. doi: 10.1016/s0168-3659(01)00429-1.
Chari et al., Immunoconjugates containing novel maytansinoids: promising anticancer drugs. Cancer Res. 1992;52(1):127-31.
Charreyre et al., Fluorescence energy transfer study of the conformation of oligonucleotides covalently bound to polystyrene latex particles. Langmuir. 1997;13: 3103-10.
Chavany, et al., Adsorption of oligonucleotides onto polyisohexylcyanoacrylate nanoparticles protects them against nucleases and increases their cellular uptake. Pharma. Res. 1994;11(9): 1370-8.
Chen et al., Ionic strength-dependent persistence lengths of single-stranded RNA and DNA. Proc Natl Acad Sci USA. 2012;109:799-804.
Chen et al., Kinetics and thermodynamics of DNA hybridization on gold nanoparticles. Nucleic Acids Res. Jun. 2009;37(11):3756-65. doi: 10.1093/nar/gkp230. Epub Apr. 20, 2009.
Chen et al., Nanoparticle-aptamer: an effective growth inhibitor for human cancer cells. IMECE 2009-11966. Jul. 8, 2010;271-2. https://doi.org/10.1115/IMECE2009-11966. 2 pgs.
Cheng et al., Interdigitated phospholipid/alkanethiol bilayers assembled on APTMS-supported gold colloid electrodes. Electroanalysis. 2004;16(1-2):127-31. doi:10.1002/elan.200302929.
Cheng et al., Tandem synthesis of core-shell brush copolymers and their transformation to peripherally cross-linked and hollowed nanostructures. J Am Chem Soc. May 31, 2006;128(21):6808-9. Published on web May 6, 2006.
Chinnathambi et al., Binding mode of CpG Oligodeoxynucleotides to nanoparticles regulates bifurcated cytokine induction via Toll-like Receptor 9. Sci Reports. 2012;2:1-9.
Chirila et al., The use of synthetic polymers for delivery of therapeutic antisense oligodeoxynucleotides. Biomaterials. 2002;23: 321-42.
Cho et al., Immunostimulatory DNA-based vaccines induce cytotoxic lymphocyte activity by a T-helper cell-independent mechanism. Nat Biotechnol. May 2000;18(5):509-14.
Cho et al., Targeted delivery of siRNA-generating DNA nanocassettes using multifunctional nanoparticles. Small. Jun. 10, 2013;9(11):1964-73. doi: 10.1002/smll.201201973. Epub Jan. 6, 2013.
Cho et al., Therapeutic nanoparticles for drug delivery in cancer. Clin Cancer Res. Mar. 1, 2008;14(5):1310-6. doi: 10.1158/1078-0432.CCR-07-1441.

(56) References Cited

OTHER PUBLICATIONS

Choi et al., Mechanism for the endocytosis of spherical nucleic acid nanoparticle conjugates, Proc. Natl. Acad. Sci. U.S.A. 2013;110:7625-7630.
Chung et al., Nuclease-resistant DNA aptamer on gold nanoparticles for the simultaneous detection of Pb2+ and Hg2+ in human serum, Biosens. Bioelectron. 41 :827-32 (2013).
Cload et al., Polyether tethered oligonucleotide probes. J. Am. Chem. Soc. 1991;113(16): 6324-6.
Combadiere et al., Particle-based vaccines for transcutaneous vaccination. Comp Immunol Microbiol Infect Dis. Mar. 2008;31(2-3):293-315. Epub Oct. 30, 2007. Review.
Concise Encyclopedia of Polymer Science and Engineering, "Polynucleotides," J. I. Kroschwitz Ed., John Wiley & Sons, pp. 858-859 (1990).
Cook, Medicinal chemistry of antisense oligonucleotides—future opportunities, Anti-Cancer Drug Design, 6:585-607 (1991).
Cui et al., Topical immunization using nanoengineered genetic vaccines. J Control Release. May 17, 2002;81(1-2):173-84.
Cutler et al. J. Am. Chem. Soc. 134:1376-1391 (Year: 2012).
Cutler et al., Polyvalent nucleic acid nanostructures. J. Am. Chem. Soc. 2011;133:9254.
Cutler et al., Polyvalent oligonucleotide iron oxide nanoparticle "click" conjugates. Nano Lett. Apr. 14, 2010;10(4):1477-80. doi:10.1021/nl100477m.
Cutler et al., Spherical nucleic acids. J Am Chem Soc. Jan. 25, 2012;134(3):1376-91. doi: 10.1021/ja209351u. Epub Jan. 9, 2012.
Dave et al. ACS Nano vol. 5, pp. 1304-1312 (Year: 2011).
Dave et al., Programmable assembly of DNA-functionalized liposomes by DNA. ACS Nano. Feb. 22, 2011;5(2):1304-12. doi: 10.1021/nn1030093. Epub Jan. 4, 2011.
De Mesmaeker et al., Backbone modifications in oligonucleotides and peptide nucleic acid systems, Curr. Opin. in Struct. Biol., 5: 343-55 (1995).
Deering et al., Nucleic acid vaccines: prospects for non-viral delivery of mRNA vaccines. Expert Opin Drug Deliv. Jun. 2014;11(6):885-99. doi: 10.1517/17425247.2014.901308. Epub Mar. 26, 2014. Review.
Dessi et al., Role of cholesterol synthesis and esterification in the growth of CEM and MOLT4 lymphoblastic cells. Biochem J. Feb. 1, 1997;321 ( Pt 3):603-8.
Dhar et al., Polyvalent oligonucleotide gold nanoparticle conjugates as delivery vehicles for platinum (IV) warheads. J Am Chem Soc. Oct. 21, 2009;131(41):14652-3. doi: 10.1021/ja907182.
Diebold et al., Nucleic acid agonists for Toll-like receptor 7 are defined by the presence of uridine ribonucleotides. Eur J Immunol. Dec. 2006;36(12):3256-67.
Dikmen et al., Targeting critical steps of cancer metastasis and recurrence using telomerase template antagonists. Biochim Biophys Acta. Apr. 2009;1792(4):240-7. doi: 10.1016/j.bbadis.2009.01.018. Epub Feb. 9, 2009.
Dua et al., Liposome: Methods of Preparation and Applications. (IJPSR (2012) 3(2):14-20).
Durand et al., Circular dichroism studies of an oligodeoxyribonucleotide containing a hairpin loop made of a hexaethylene glycol chain: conformation and stability. Nucl. Acids Res. 1990;18(21): 6353-9.
Eckstein, Oligonucleotides and Analogues, 1st Ed. (Oxford University Press, New York) (1991).
Elbakry, A. et al., "Layer-by-Layer Assembled Gold Nanoparticles for siRNA Delivery," Nano Lett., 2009, 9 (5), 2059-2064.
Elghanian et al., Selective colorimetric detection of polynucleotides based on the distance-dependent optical properties of gold nanoparticles. Science. 1997;277(5329):1078-81.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Englisch et al., "Chemically Modified Oligonucleotides as Probes and Inhibitors" Angewandte Chemie, International Edition, 30:613-629 (1991).

Fan et al., Immunization via hair follicles by topical application of naked DNA to normal skin. Nat Biotechnol. 1999;17(9):870-872. doi:10.1038/12856.
Fattal et al., Biodegradable polyalkylcyanoacrylate nanoparticles for the delivery of oligonucleotides. J. Controlled Release. 1998;53:137-143.
Ferentz et al., Disulfide-crosslinked oligonucleotides. J. Am. Chem. Soc. 1991;113(10): 4000-2.
Ferrari, Cancer nanotechnology: opportunities and challenges. Nature Reviews Cancer. 2005;5: 161-71.
Fishwick et al., Phytochemistry vol. 16, Issue 10, 1977, pp. 1507-1510.
Forman et al., Toward Artificial Ion Channels: A Lipophilic G-Quadruplex. J. Am. Chem. Soc. 2000;122(17):4060-4067. DOI: 10.1021/ja9925148.
Forsbach et al., Identification of RNA sequence motifs stimulating sequence-specific TLR8-dependent immune responses. J Immunol. Mar. 15, 2008;180(6):3729-38.
Freier et al., The ups and downs of nucleic acid duplex stability: structure-stability studies on chemically-modified DNA:RNA duplexes, Nucleic Acids Research, 25:4429-43 (1997).
Freier et al., The ups and downs of nucleic acid duplex stability: structure-stability studies on chemically-modified DNA:RNA duplexes. Nucleic Acids Research. 1997;25(22):4429-4443.
Ghosh et al., Gold nanoparticles in delivery applications. Adv. Drug Deliv. Rev. 2008;60(11):1307-15.
Gibson et al., Paclitaxel-functionalized gold nanoparticles. J. Am. Chem. Soc. 2007;129(37):11653-61.
Giljohann et al., Gene regulation with polyvalent siRNA-nanoparticle conjugates. J Am Chem Soc. Feb. 18, 2009;131(6):2072-3.
Giljohann et al., Gold nanoparticles for biology and medicine. Angew Chem Int Ed Engl. Apr. 26, 2010;49(19):3280-94. doi: 10.1002/anie.200904359.
Giljohann et al., Oligonucleotide loading determines cellular uptake of DNA-modified gold nanoparticles. Nano Lett. Dec. 2007;7(12):3818-21. Epub Nov. 13, 2007.
Gissot et al., Nucleoside, nucleotide and oligonucleotide based amphiphiles: a successful marriage of nucleic acids with lipids. Org. Biomol. Chem. 2008;6:1324-33.
Godard, G. et al., "Antisense Effects of Cholesterol-Oligodeoxynucleotide Conjugates Associated with Poly(alkylcyanoacrylate) Nanoparticles," Eur. J. Biochem., 1995, 232 (2), 404-410.
Goncalves et al., Uptake of high density lipoprotein (HDL) cholesteryl esters by human acute leukemia cells. Leuk Res. Aug. 2005;29(8):955-9. Epub Feb. 24, 2005.
Goodrich et al., Non-coding-RNA regulators of RNA polymerase II transcription. Nat. Rev. Mol. Cell Biol. 2006;7(8):612-6.
Gramzinski et al., Interleukin-12 and gamma interferon-dependent protection against malaria conferred by CpG oligodeoxynucleotide in mice. Infection and Immunity. Mar. 2001:1643-9.
Graziani et al., Uptake of a cholesterol-rich emulsion by breast cancer. Gynecol Oncol. Jun. 2002;85(3):493-7.
Greish, Enhanced permeability and retention (EPR) effect for anti-cancer nanomedicine drug tarqetinq, Methods Mal. Biol. 624:25-37 (2010).
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Gryaznov, Oligonucleotide n3'.fwdarw.p5' phosphoramidates and thio-phoshoramidates as potential therapeutic agents. Chem Biodivers. Mar. 2010;7(3):477-93. doi: 10.1002/cbdv.200900187. Review.
Guiducci et al., Properties regulating the nature of the plasmacytoid dendritic cell response to Toll-like receptor 9 activation. J Exp Med. Aug. 7, 2006;203(8):1999-2008. Epub Jul. 24, 2006.
Gunnarsson et al., Liposome-Based Chemical barcodes for Single Molecule DNA Detection Using imaging Mass Spectrometry, Nano. Lett. 2010;10:732-37.
Gursel et al., Repetitive elements in mammalian telomeres suppress bacterial DNA-induced immune activation. J Immunol. Aug. 1, 2003;171(3):1393-400.

(56) References Cited

OTHER PUBLICATIONS

Hammond et al., An RNA-directed nuclease mediates post-transcriptional gene silencing in *Drosophilia* cells. Nature. 2000;404: 293-6.
Han et al., Drug and gene delivery using gold nanoparticles. NanoBiotechnology. Mar. 2007;3(1):40-5.
Hartmann et al., Delineation of a CpG phosphorothioate oligodeoxynucleotide for activating primate immune responses in vitro and in vivo. J Immunol. Feb. 1, 2000;164(3):1617-24.
Hayashi, Ultrafine particles. J. Vac. Sci. Technol. 1987;5(4):1375-1384.
He et al., Phospholipid-stabilized Au-nanoparticles. Biomacromolecules. May-Jun. 2005;6(3):1224-5.
Hegner et al., Modified DNA immobilized on bioreactive self-assembled monolayer on gold for dynamic force microscopy imaging in aqueous buffer solution. J. Vac. Sci. Technol. B, 1996;14(2):1418-21.
Heil et al., Species-specific recognition of single-stranded RNA via toll-like receptor 7 and 8. Science. Mar. 5, 2004;303(5663):1526-9. Epub Feb. 19, 2004.
Hellstrom et al., Epitaxial growth of DNA-assembled nanoparticle superlattices on patterned substrates. Nano Lett. 2013;13(12):6084-90. doi: 10.1021/n14033654. Epub Nov. 20, 2013.
Hill et al., "Controlling the Lattice Parameters of Gold Nanoparticle FCC Crystals with Duplex DNA Linkers," Nano Lett 8(8): 2341-2344 (2008).
Hong et al., Directed Assembly of Nucleic Acid-Based Polymeric Nanoparticles from Molecular Tetravalent Cores, *J. Am. Chem. Soc.* 137:8184-91 (2015).
Hope et al., Production of large unilamellar vesicles by a rapid extrusion procedures; characterization of size distribution, trapped volume and ability to maintain a membrane potential. Biochim Biophys Acta. Jan. 10, 1985;812(1):55-65. Abstractonly.
Hotz et al., VEGF antisense therapy inhibits tumor growth and improves survival in experimental pancreatic cancer. Surgery. Feb. 2005;137(2):192-9.
Houot et al., T-cell modulation combined with intratumoral CpG cures lymphoma in a mouse model without the need for chemotherapy. Blood. Apr. 2009;113(15):3546-52. doi: 10.1182/blood-2008-07-170274. Epub Oct. 21, 2008.
Hsu et al., Delivery of siRNA and other macromolecules into skin and cells using a peptide enhancer. Proc Natl Acad Sci U S A. 2011;108(38):15816-15821. doi:10.1073/pnas.1016152108.
Hurst et al., Maximizing DNA loading on a range of gold nanoparticle sizes, Anal. Chem. 2006;78:8313.
Hussain et al., A novel anionic dendrimer for improved cellular delivery of antisense oligonucleotides. J. Controlled Rel. 2004;99: 139-55.
Hwu et al., Targeted Paclitaxel by conjugation to iron oxide and gold nanoparticles. J. Am. Chem. Soc . . . 2009;131(1):66-8.
International Preliminary Report on Patentability dated Apr. 20, 2017 for PCT/US2015/054288.
International Preliminary Report on Patentability dated Aug. 31, 2017 for PCT/US2016/018395.
International Preliminary Report on Patentability dated Feb. 4, 2016 for PCT/US2014/048291.
International Preliminary Report on Patentability dated Feb. 4, 2016 for PCT/US2014/048294.
International Preliminary Report on Patentability dated Jan. 12, 2017 for PCT/US2015/038771.
International Preliminary Report on Patentability dated Jan. 25, 2018 for PCT/US2016/042291.
International Preliminary Report on Patentability dated Jul. 27, 2017 for PCT/US2016/013365.
International Preliminary Report on Patentability dated Oct. 13, 2016 for PCT/US2015/024255.
International Preliminary Report on Patentability dated Sep. 28, 2017 for PCT/US2016/022579.
International Search Report and Written Opinion dated Apr. 24, 2017 for PCT/US2017/016084.
International Search Report and Written Opinion dated Aug. 25, 2017 for PCT/US2017/031428.
International Search Report and Written Opinion dated Aug. 3, 2016 for PCT/US2016/018395.
International Search Report and Written Opinion dated Dec. 15, 2014 for PCT/US2014/048291.
International Search Report and Written Opinion dated Dec. 17, 2014 for PCT/US2014/048294.
International Search Report and Written Opinion dated Jul. 10, 2017 for PCT/US2017/0274174.
International Search Report and Written Opinion dated Jul. 28, 2017 for PCT/US2017/031419.
International Search Report and Written Opinion dated Jul. 8, 2015 for PCT/US2015/024255.
International Search Report and Written Opinion dated May 16, 2016 for PCT/US2016/013365.
International Search Report and Written Opinion dated May 23, 2016 for PCT/US2016/022579.
International Search Report and Written Opinion dated Nov. 18, 2015 for PCT/US2015/054288.
International Search Report and Written Opinion dated Oct. 6, 2016 for PCT/US2016/042291.
International Search Report and Written Opinion dated Sep. 14, 2017 for PCT/US2017/031423.
International Search Report and Written Opinion dated Sep. 30, 2015 for PCT/US2015/038771.
Jackson et al., How do microRNAs regulate gene expression? Sci STKE. 2007(367):rel.
Jahn et al., Microfluidic directed formation of liposomes of controlled size. Langmuir. May 22, 2007;23(11):6289-93. ; Epub Apr. 24, 2007.
Jain et al., Synthesis of protein-loaded hydrogel particles in an aqueous two-phase system for coincident antigen and CpG oligonucleotide delivery to antigen-presenting cells. Biomacromolecules. Sep.-Oct. 2005;6(5):2590-600.
Jakobsen et al., Assembly of liposomes controlled by triple helix formation, Bioconjugate Chem. 2013;24:1485-95.
Jaschke et al., Automated incorporation of polyethylene glycol in synthetic oligonucleotides. Tetrahedron Lett. 1993;34: 301-4.
Jason et al., Toxicology of antisense therapeutics. Toxicol. Appl. Pharmacol. 2004;201(1): 66-83.
Jayawickramarajah et al., Allosteric control of self-assembly: modulating the formation of guanine quadruplexes through orthogonal aromatic interactions. Angew Chem Int Ed Engl. 2007;46(40):7583-6.
Jensen et al., Spherical nucleic acid nanoparticle conjugates as an RNAi-based therapy for glioblastoma, Sci. Trans. Med., 5:209ra152 (2013).
Jeong et al., Novel intracellular delivery system of antisense oligonucleotide by self-assembled hybrid micelles composed of DNA/PEG conjugate and cationic fusogenic peptide. Bioconjugate Chem. 2003;14: 473-9.
Jin et al., Radiosensitization of paclitaxel, etanidazole and paclitaxel+ etanidazole nanoparticles on hypoxic human tumor cells in vitro. Biomaterials. 2007;28(25):3724-30.
Kaczmarek et al., 2,-Linking of lipids and other functions to uridine through 1,2,3-triazoles and membrane anchoring of the amphiphilic products. Eur J Org Chem. Mar. 1, 2010; 2010(8):1579-86. DOI: 10.1002/ejoc.200901073.
Kan et al., Role of Kupffer cells in iodized oil embolization. Invest. Radiol. 1994;29(11 ):990-3.
Kandimalla et al., Secondary structures in CpG oligonucleotides affect immunostimulatory activity. Biochem Biophys Res Commun. Jul. 11, 2003;306(4):948-53.
Kandimalla Immunostimulatory et al., Conjugation of Ligands at the 5'-End of CpG DNA Affects Immunostimulatory Activity. Bioconjugate Chemistry 2002 13 (5), 966-974. DOI: 10.1021/bc0200374.
Kanzler et al., Therapeutic targeting of innate immunity with Toll-like receptor agonists and antagonists. Nat Med. May 2007;13(5):552-9.

(56) References Cited

OTHER PUBLICATIONS

Karathanasis et al., Selective targeting of nanocarriers to neutrophils and monocytes. Ann Biomed Eng. Oct. 2009;37(10):1984-92. doi: 10.1007/s10439-009-9702-5. Epub Apr. 23, 2009.
Kasuya et al., Chapter 8—Bio-nanocapsule-liposome conjugates for in vivo pinpoint drug and gene delivery. Methods Enzymol. 2009;464:147-66.
Katz et al., Integrated nanoparticle-biomolecule hybrid systems: synthesis, properties, and applications. Angew. Chem. Int. Ed. 2004;43: 6042-108.
Katzman et al., Cholesterol-dependent infection of Burkitt's lymphoma cell lines by Epstein-Barr virus. J Gen Virol. Nov. 2003;84(Pt 11):2987-92.
Kelly et al., Targeted Liposomal Drug Delivery to Monocytes and Macrophages. J Drug Delivery. 2011;1-11.
Kerkmann et al., Immunostimulatory properties of CpG-oligonucleotides are enhanced by the use of protamine nanoparticles. Oligonucleotides. 2006 Winter;16(4):313-22.
Khmelinskaia et al., Effect of anchor positioning on binding and diffusion of elongated 3D DNA nanostructures on lipid membranes. J. Phys. D: Appl. Phys. Apr. 13, 2016;49(19):194001.
Kim et al., Cationic solid lipid nanoparticles reconstituted from low density lipoprotein components for delivery of siRNA. Mol Pharm. Jul.-Aug. 2008;5(4):622-31. doi: 10.1021/mp8000233. Epub May 8, 2008.
Kim et al., Direct synthesis of polymer nanocapsules with a noncovalently tailorable surface. Angew. Chem. Int. Ed. Engl. 2007;46(19):3471-4.
Kim et al., Direct synthesis of polymer nanocapsules: self-assembly of polymer hollow spheres through irreversible covalent bond formation. J. Am. Chem. Soc. 2010;132(28):9908-19.
Kim et al., Effect of bovine serum albumin on the stability of methotrexate-encapsulated liposomes, Arch. Pharmacal Res. 1991;14:336.
Kim, S. et al., "Systemic and Specific Delivery of Small Interfering RNAs to the Liver Mediated by Apolipoprotein A-I," Mol. Ther., 2007, 15 (6), 1145-1152.
Kimura-Suda et al., Base-Dependent Competive Adsorption of Single-Stranded DNA on Gold. Journal of the American Chemical Society. 2003;125: 9014-9015.
Kloosterman et al., In situ detection of miRNAs in animal embryos using LNA-modified oligonucleotide probes. Nat. Methods. 2006;3: 27-9.
Kolarova et al., Preparation of magnetic oligo (dT) particles. Biotechniques. 1996;20: 196-8.
Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.
Krieg et al., CpG motifs in bacterial DNA trigger direct B-cell activation. Nature. Apr. 6, 1995;374(6522):546-9. doi: 10.1038/374546a0.
Krieg et al., Sequence motifs in adenoviral DNA block immune activation by stimulatory CpG motifs. Proc Natl Acad Sci U S A. Oct. 13, 1998;95(21):12631-6. doi: 10.1073/pnas.95.21.12631.
Krieg. Antiinfective applications of toll-like receptor 9 agonists. Proc Am Thorac Soc. Jul. 2007;4(3):289-94.
Krug et al. Identification of CpG oligonucleotide sequences with high induction of IFN-alpha/beta in plasmacytoid dendritic cells. Eur J Immunol. Jul. 2001;31(7):2154-63.
Krutzfeldt et al., Silencing of microRNAs in vivo with 'antagomirs'. Nature. 2005;438(7068):685-9.
Landfester et al., From polymeric particles to multifunctional nanocapsules for biomedical applications using the miniemulsion process. J. Polymer Sci. Part A.2010; 48(3):493-515.
Langer. New methods of drug delivery. Science. Sep. 28, 1990;249(4976):1527-33.
Laquini et al., iPreparation, Characterization and Applications of Liposomes: State of the Art. J Colloid Sci and Biotechnol. 2012;1:147-68.
Leander, D., "Mixed-Monolayer Gold Nanoparticles for Cancer Therapeutics," Nanoscape, 2010, 7 (1), 11-14.
Lebedeva et al., Antisense oligonucleotides: Promise and reality. Annu. Rev. Pharmacol. Toxicol. 2001;41: 403-19.
Lee et al., A DNA-Gold Nanoparticle-Based Colormetric Competition Assay for the Detection of Cysteine. Nano Letter. 2008;8(2):529-533.
Lee et al., All-in-one target-cell-specific magnetic nanoparticles for simultaneous molecular imaging and siRNA delivery. Angew Chem Int Ed Engl. 2009;48(23):4174-9. doi:10.1002/anie.200805998.
Lee et al., Chip-based scanometric detection of mercuric ion using DNA-functionalized gold nanoparticles. Anal. Chem. 2008;80(17):6805-8.
Lee et al., Colorimetric detection of mercuric ion (Hg2+) in aqueous media using DNA-functionalized gold nanoparticles. Angew Chem Int Ed Engl. 2007;46(22):4093-6.
Lee, IH, Kwon HK, an S, Kim D, Kim S, Yu MK, Lee JH, Lee TS, Im SH, Jon S. Imageable antigen-presenting gold nanoparticle vaccines for effective cancer immunotherapy in vivo. Angew Chem Int Ed Engl. Aug. 27, 2012;51(35):8800-5. doi:10.1002/anie.201203193.
Lenert et al., Inhibitory oligonucleotides block the induction of AP-1 transcription factor by stimulatory CpG oligonucleotides in B cells. Antisense Nucleic Acid Drug Dev. 2003;13(3):143-50.
Lennox et al., Characterization of modified antisense oligonucleotides in Xenopus laevis embryos. Oligonucleotides. 2006 Spring;16(1):26-42.
Leon et al., Alterations in cholesterol regulation contribute to the production of intratumoral androgens during progression to castration-resistant prostate cancer in a mouse xenograft model. Prostate. Mar. 1, 2010;70(4):390-400. doi:10.1002/pros.21072.
Lesieur et al., Size analysis and stability study of lipid vesicles by high-performance gel exclusion chromatography, turbidity, and dynamic light scattering. Anal Biochem. Feb. 1, 1991;192(2):334-43.
Leslie et al., A new tool for oligonucleotides import into cells. Clin. Chem. 2009;55: 609-10.
Lewandowski et al., Topically delivered spherical nucleic acid nanoconjugates targeting TNF improve the psoriatic phenotype. J Invest Dermatol. 2015 135:S71. Abstract 413.
Lewis, Controlled release of bioactive agents from lactide/glycolide polymer. pp. 1-41, in Chasin et al. (eds.), Biodegradable Polymers as Drug Delivery Systems, Marcel Dekker (1990).
Li et al., "Molecular spherical nucleic acids," PNAS pp. 1-5 (2018).
Li et al., Combination delivery of antigens and CpG by lanthanides-based core-shell nanoparticles for enhanced immune response and dual-mode imaging. Adv Healthc Mater. Oct. 2013;2(10):1309-13. doi:10.1002/adhm.201200364. Epub Mar. 25, 2013.
Li et al., Dual-reactive surfactant used for synthesis of functional nanocapsules in miniemulsion. J. Am. Chem. Soc. 2010;132(23):7823-5.
Li et al., Molecular spherical nucleic acids. Proc Nati Acad Sci U S A. Apr. 24, 2018; 115(17):4340-4344. doi: 10.1073/pnas.1801836115. Epub Apr. 9, 2018.
Li et al., Nanofabrication by DNA self-assembly. Materials Today. Elsevier Science. May 1, 2009;12(5)24-32.
Li et al., Nucleolin-targeting liposomes guided by aptamer AS1411 for the delivery of siRNA for the treatment of malignant melanomas. Biomaterials. Apr. 2014;35(12):3840-50. doi: 10.1016/j.biomaterials.2014.01.019. Epub Jan. 31, 2014.
Li et al., Reversible and Chemically Programmable Micelle Assembly with DNA Block-Copolymer Amphiphiles, Nano Lett. 2004;4:1055.
Li et al., Targeted delivery of antisense oligodeoxynucleotide and small interference RNA into lung cancer cells. Mol Pharm. Sep.-Oct. 2006;3(5):579-88. doi: 10.1021/mp060039w. Publication Date:Jul. 12, 2006.
Lin et al., Effector/memory but not naive regulatory T cells are responsible for the loss of concomitant tumor immunity. J. Immunol. 2009;182: 6095-104.
Lin et al., Gold nanoparticle delivery of modified CpG stimulates macrophages and inhibits tumor growth for enhanced immunotherapy. PLoS One. May 15, 2013;8(5):e63550. doi: 10.1371/journal.pone.0063550. Print 2013.

(56) References Cited

OTHER PUBLICATIONS

Lin et al., Modeling genomic diversity and tumor dependency in malignant melanoma. Cancer Res. 2003;68: 664-73.
Link et al., Size and Temperature Dependence of the Plasmon Absorption of Colloidal Gold Nanoparticles. J. Phys. Chem. B. 1999;103(21):4212-7.
Linse et al., Temperature-dependent micellization in aqueous block copolymer solutions, Macromolecules. 25:5434-5439 (1992).
Liu et al., Argonaute2 is the catalytic engine of mammalian RNAi. Science. 2004;305(5689): 1437-41.
Liu et al., Bioconjugated pluronic triblock-copolymer micelle-encapsulated quantum dots for targeted imaging of cancer: in vitro and in vivo studies, Theranostics. 2:705-13 (2012).
Liu et al., DNA-based micelles: synthesis, micellar properties and size-dependent cell permeability, Chemistry. 2010;16:3791-7.
Liu et al., Membrane anchored immunostimulatory oligonucleotides for in vivo cell modification and localized immunotherapy. Angew Chem Int Ed Engl. Jul. 25, 2011;50(31):7052-5. doi: 10.1002/anie.201101266. Epub Jun. 17, 2011.
Liu et al., New Poly(D-glucaramidoamine)s Induce DNA Nanoparticle Formation and Efficient Gene Delivery into Mammalian Cells. J. Am. Chem. Soc. 2004;126:7422-7423.
Liu et al., Structure-based programming of lymph-node targeting in molecular vaccines. Nature. Mar. 27, 2014;507(7493):519-22. doi: 10.1038/nature12978.
Liu et al., Synthesis, stability, and cellular internalization of gold nanoparticles containing mixed peptide-poly(ethylene glycol) monolayers. Anal. Chem. 2007;79: 2221-9.
Liu, J. et al., Silica Nanoparticle Supported Lipid Bilayers for Gene Delivery, Chem. Commun., 2009, 5100-5102.
Ljubimova et al., Nanoconjugate based on polymalic acid for tumor targeting. Chem Biol Interact. Jan. 30, 20080;171(2):195-203. Epub Feb. 8, 2007.
Luo et al., Synthetic DNA delivery systems. Nat Biotechnol. Jan. 2000;18(1):33-7.
Luthi et al., Nanotechnology for synthetic high-density lipoproteins. Trens Mol Med. Dec. 2010;16(12):553-60. doi: 10.1016/j.molmed.2010.10.006. Epub Nov. 17, 2010.
Lytton-Jean et al., A thermodynamic investigation into the binding properties of DNA functionalized gold nanoparticle probes and molecular fluorophore probes. J Am Chem Soc. Sep. 21, 2005;127(37):12754-5.
Lytton-Jean et al., Highly Cooperative Behavior of Peptide Nucleic Acid-Linked DNA-Modified Gold-Nanoparticle and Comb-Polymer Aggregates, Advanced Materials, 21: 706 (2009).
Ma et al., Design and synthesis of RNA miniduplexes via a synthetic linker approach. 2. Generation of covalently closed, double-stranded cyclic HIV-1 TAR RNA analogs with high Tat-binding affinity. Nucl. Acids Res. 1993;21: 2585-9.
Ma et al., Design and synthesis of RNA miniduplexes via a synthetic linker approach. Biochemistry. 1993;32(7): 1751-8.
Major, M. et al., "Characterisation and Phase Behaviour of Phospholipid Bilayers Adsorbed on Spherical Polysaccharidic Nanoparticles," Biochimica et Biophysica Acta, 1997, 1327, 32-40.
Mangsbo et al., Enhanced tumor eradication by combining CTLA-4 or PD-1 blockade with CpG therapy. J Immunother. Apr. 2010;33(3):225-35. doi: 10.1097/CJI.0b013e3181c01fcb.
Manoharan et al., Lipidic nucleic acids. Tetrahedron Letters. May 22, 1995;36(21):3651-4.
Marabelle et al. Depleting tumor-specific Tregs at a single site eradicates disseminated tumors, J Clin Invest. 2013; 123(6):2447-2463.
Marshall et al., Novel chimeric immunomodulatory compounds containing short CpG oligodeoxyribonucleotides have differential activities in human cells. Nucleic Acids Res. Sep. 1, 2003;31(17):5122-33.
Martin et al., Ein neur Zugang zu 2'-O-alkylribonucleosiden and Eigenschaften deren oligonucleotide Hely, Chim. Acta, 78:486-504 (1995).

Martinson et al., Impact of Class A, B and C CpG-oligodeoxynucleotides on in vitro activation of innate immune cells in human immunodeficiency virus-1 infected individuals. Immunology. 2007;120(4):526-35.
Massich et al., Cellular response of polyvalent oligonucleotide-gold nanoparticle conjugates, ACS Nano. 4:5641-6 (2010).
Massich et al., Regulating immune response using polyvalent nucleic acid-gold nanoparticle conjugates. Mol Pharm. Nov.-Dec. 2009;6(6):1934-40.
Matijevic et al., Fine Particles Part II: Formation Mechanisms and Applications. MRS Bulletin pp. 16-47 (1990).
Mayer et al., Nucleic Acid and Peptide Aptamers: Methods and Protocols (Edited by Mayer, Humana Press) Methods in Molecular Bioloav (2009). 404 pages.
McAllister et al., Polymeric nanogels produced via inverse microemulsion polymerization as potential gene and antisense delivery agents, J. Am. Chem. Soc., 124:15198 (2002).
McBain, S. et al., "Polyethyleneimine Functionalized Iron Oxide Nanoparticles as Agents for DNA Deliver and Transfection," J. Mater. Chem., 2007, 17, 2561-2565.
McKay et al., Characterization of a potent and specific class of antisense oligonucleotide inhibitor of human protein kinase C-alpha expression. J Biol Chem. Jan. 15, 1999;274(3):1715-22.
Mendell, MicroRNAs: critical regulators of development, cellular physiology and malignancy. Cell Cycle. 2005;4(9):1179-84.
Ming et al., Albumin-based nanoconjugates for targeted delivery of ; therapeutic oligonucleotides. Biomaterials. Oct. 2013;34(32):7939-49. doi:; 10.1016/j.biomaterials.2013.06.066. Epub Jul. 19, 2013.
Mohamed et al., Effect of toll-like receptor 7 and 9 targeted therapy to prevent the development of hepatocellular carcinoma. Liver Int. Mar. 2015;35(3):1063-76. doi: 10.1111/liv.12626. Epub Jul. 30, 2014.
Monia et al., Nuclease resistance and antisense activity of modified oligonucleotides targeted to Ha-ras. J Biol Chem. Jun. 14, 2014;271(24):14533-40.
Mozos et al., The expression of the endoplasmic reticulum stress sensor BiP/GRP78 predicts response to chemotherapy and determines the efficacy of proteasome inhibitors in diffuse large b-cell lymphoma. Am J Pathol. Nov. 2011;179(5):2601-10.doi:10.1016/j.ajpath.2011.07.031. Epub Sep. 9, 2011.
Mui et al., Immune stimulation by a CpG-containing oligodeoxynucleotide is enhanced when encapsulated and delivered in lipid particles. J Pharmacol Exp Ther. Sep. 2001;298(3):1185-92.
Mulas et al., Cholesterol esters as growth regulators of lymphocytic leukaemia cells. Cell Prolif. Aug. 2011;44(4):360-71. doi: 10.1111/j.1365-2184.2011.00758.x. Epub Jun. 6, 2011.
Munde et al., Induced fit conformational changes of a "reversed amidine" heterocycle: optimized interactions in a DNA minor groove complex. J Am Chem Soc. May 2, 2007;129(17):5688-98. Epub Apr. 11, 2007.
Nam et al., Nanoparticle-based bio-bar codes for the ultrasensitive detection of proteins. Science. Sep. 26, 2003;301(5641):1884-6.
Niemeyer, C. et al., "Bifunctional DNA-Gold Nanoparticle Conjugates as Building Blocks for the Self-Assembly of Cross-Linked Particle Layers," Biochemical and Biophysical Research Communications, 2003, 311 (4), 995-999.
Nikolov et al., Bias-dependent admittance in hybrid bilayer membranes. Langmuir Aug. 2006.15;22(17):7156-8.
Ohishi et al., Hepatocellular carcinoma detected by iodized oil. Use of anticancer agents. Radiology. 1985;154(1):25-9.
Okayasu et al., Selective and persistent deposition and gradual drainage of iodized oil, Lipiodol in the hepatocellular carcinoma after injection into the feeding hepatic artery. Am. J. Clin. Pathol. 1988;90(5):536-44.
Opalinska et al., Nucleic-acid therapeutics: basic principles and recent applications. Nat. Rev. Drug Discov. 2002;1: 503-14.
Opdahl et al., Independent control of grafting density and conformation of single-stranded DNA brushes. Proc Natl Acad Sci U.S.A. 2007;104: 9-14.
Osman et al., Morpholino antisense oligonucleotides targeting intronic repressor Element1 improve phenotype in SMA mouse models. Human Molecular Genetics. 2014;23(18):4832-45.

(56) References Cited

OTHER PUBLICATIONS

Ozpolat et al., Nanomedicine based approaches for the delivery of siRNA in cancer. J. Intern. Med. 2010;267(1):44-53.
Parrish et al., Soluble Camptothecin Derivatives Prepared by Click Cycloaddition Chemistry on Functional Aliphatic Polyesters. Bioconjugate Chem. 2006;18: 263-267.
Patel et al., Peptide antisense nanoparticles. Proc Natl Acad Sci U S A. Nov. 11, 2011;105(45):17222-6. doi: 10.1073/pnas.0801609105.
Patel et al., Scavenger receptors mediate cellular uptake of polyvalent oligonucleotide-functionalized gold nanoparticles, Bioconj. Chem., 21:2250 (2010).
Patil et al., "Evidence for Novel Interdigitated Bilayer Formation of Fatty Acids During Three-Dimensional Self-Assembly on Silver Colloidal Particles," J. Am. Chem. Soc., 1997, 119 (39), 9281-9282.
Patil et al., DNA-based therapeutics and DNA delivery systems: a comprehensive review. AAPS J., 2005;7(1): E61-77.
Patwa et al., Hybrid lipid oligonucleotide conjugates: synthesis, self-assemblies and biomedical applications. Chem Soc Rev. 2011;40:5844-54.
Paul, New Way to Kill Lymphoma without Chemotherapy uses Golden Nanoparticles. Feinberg School of Medicine: Northwestern University. Jan. 22, 2013 4 pages. ww.feinberg.northwestern.edu/news/2013/01/lymphoma_nanoparticales.html.
Periyasamy et al., Nanomaterials for the local and targeted delivery of osteoarthritis drugs. J Nanomater. 2012:2012:Article 673968. 13 pages. doi:0.1155/2012/673968.
Peter et al., Characterization of suppressive oligodeoxynucleotides that inhibit Toll-like receptor-9-mediated activation of innate immunity. Immunology. Jan. 2008;123(1):118-28. Epub Oct. 23, 2007.
Pfeiffer et al., Bivalent Cholesterol-Based Coupling of Oligonucleotides to Lipid Membrane Assemblies. J. Am. Chem. Soc. 2004;126:10224-10225.
Pfeiffer et al., Quantification of oligonucleotide modifications of small unilamellar lipid vesicles. Anal. Chem. 2006;78:7493-8.
Plant et al., Self-assembled phospholipid/alkanethiol biomimetic bilayers on gold. Langmuir. 1993;9:2764-7.
Pokholenko et al., Lipid oligonucleotide conjugates as responsive nanomaterials for drug delivery. J of Materials Chemistry B. 2013;5329-34.
Polizzi et al., Water-soluble nitric oxide-releasing gold nanoparticles. Langmuir. Apr. 24, 2007;23(9):4938-43. Epub Mar. 22, 2007.
Pollard, A guide to simple and informative binding assays. Mol Biol Cell. Dec. 2010;21(23):4061-7. doi: 10.1091/mbc.E10-08-0683.
Ponnappa et al., Inhibition of tumor necrosis factor alpha secretion and prevention of liver injury in ethanol-fed rats by antisense oligonucleotides. Biochem Pharmacol. Feb. 15, 2005;69(4):569-77. Epub Dec. 30, 2004.
Prasad et al., Oligonucleotides tethered to a short polyguanylic acid stretch are targeted to macrophages: enhanced antiviral activity of a vesicular stomatitis virus-specific antisense oligonucleotide. Antimicrob Agents Chemother. Nov. 1999;43(11):2689-96.
Prausnitz et al., Transdermal drug delivery, Nat. Biotechnol., 2008;26: 1261-8.
Radovic-Moreno et al., Immunomodulatory spherical nucleic acids. Proc Natl Acad Sci U S A. Mar. 31, 2015;112(13):3892-7. doi: 10.1073/pnas.1502850112. Epub Mar. 16, 2015.
Rajur et al., Covalent protein-oligonucleotide conjugates for efficient delivery of antisense molecules. Bioconjug Chem. Nov.-Dec. 1997;8(6):935-40. doi: 10.1021/bc970172u.
Ramos-Casals et al., Autoimmune diseases induced by TNF-targeted therapies: analysis of 233 cases. Medicine (Baltimore). Jul. 2007;86(4):242-51.
Rethore et al., Use of templates to fabricate nanoscale spherical structures for defined architectural control. Small, 2010;6(4):488-98.
Rojanasakul et al., Antisense inhibition of silica-induced tumor necrosis factor in alveolar macrophages. J Biol Chem. Feb. 14, 1997;272(7):3910-4.
Romanucci et al., Synthesis, biophysical characterization and anti-HIV activity of d(TG3AG) Quadruplexes bearing hydrophobic tails at the 5'-end. Bioorg Med Chem. Feb. 1, 2014;22(3):960-6. doi: 10.1016/j.bmc.2013.12.051. Epub Jan. 4, 2014.
Rosi et al., Nanostructures in biodiagnostics, Chem. Rev., 105:1547 (2005).
Rosi et al., Oligonucleotide-modified gold nanoparticles for intracellular gene regulation. Science. May 19, 2006;312(5776):1027-30.
Rothblat et al., Cell cholesterol efflux: integration of old and new observations provides new insights. J Lipid Res. May 1999;40(5):781-96.
Rothrock et al., Synthesis of nitric oxide-releasing gold nanoparticles. J Am Chem Soc. Jul. 6, 2005;127(26):9362-3.
Rubenstein et al., Antisense oligonucleotide intralesional therapy for human PC-3 prostate tumors carried in athymic nude mice. J Surg Oncol. Jul. 1996;62(3):194-200. doi: 10.1002/(SICI)1096-9098(199607)62:3<194::AID-JSO9>3.0.CO;2-2.
Rush et al., Intracellular mRNA regulation with self-assembled locked nucleic acid polymer nanoparticles. J Am Chem Soc. May 28, 2014;136(21):7615-8. doi: 10.1021/ja503598z. Epub May 14, 2014.
Saraiva et al., Nanocarriers for nitric oxide delivery. J Drug Deliv. 2011;2011:936438. doi: 10.1155/2011/936438. Epub Aug. 22, 2011.
Schieren et al., Comparison of large unilamellar vesicles prepared by a petroleum ether vaporization method with multilamellar vesicles: ESR, diffusion and entrapment analyses. Biochim Biophys Acta. Aug. 3, 1978;542(1):137-53.
Schifferlers et al., Cancer siRNA therapy by tumor selective delivery with ligand-targeted sterically stabilized nanoparticle. Nucl. Acid Res., 2004;32(19): e149.
Schmidt, Clinical setbacks for toll-like receptor 9 agonists in cancer. Nat Biotechnol. Aug. 2007;25(8):825-6. Epub Aug. 2, 2007.
Schwab et al., An approach for new anticancer drugs: Oncogene-targered antisense DNA. Ann Oncol. 1994;5(Suppl4):S55-8.
Seela et al., Oligodeoxyribonucleotides containing 1,3-propanediol as nucleoside substitute. Nucl. Acids Res., 1987;15(7): 3113-29.
Seeman, "An Overview of Structural DNA Nanotechnology," Mol Biotechnol 37(3): 246-257 (2007).
Seferos et al., Locked nucleic acid-nanoparticle conjugates, Chem. Bio. Chem., 8:1230 (2007).
Seferos et al., Polyvalent DNA nanoparticle conjugates stabilize nucleic acids. Nano Lett. Jan. 2009;9(1):308-11.
Senior et al., Stability of small unilamellar liposomes in serum and clearance from the circulation: the effect of the phospholipid and cholesterol components, Life Sci. 30:2123 (1982).
Shahzad et al., Targeted delivery of small interfering RNA using reconstituted high-density lipoprotein nanoparticles. Neoplasia. Apr. 2011;13(4):309-19.
Sharma et al., Targeting mitogen-activated protein kinase/extracellular signal-regulated kinase kinase in the mutant (V600E) B-Raf signaling cascade effectively inhibits melanoma lung metastases. Cancer Res., 2006;66: 8200-9.
Shin et al., pH-responsive high-density lipoprotein-like nanoparticles to release paclitaxel at acidic pH in cancer chemotherapy. Int J Nanomedicine. 2012;7:2805-16. doi: 10.2147/IJN.S29817. Epub Jun. 6, 2012.
Shukoor et al., CpG-DNA loaded multifunctional MnO nanoshuttles for TLR9-specific cellular cargo delivery, selective immune-activation and MRI. J. Mater. Chem., 2012,22, 8826-8834.
Sigalov, A novel ligand-independent peptide inhibitor of TREM-1 suppresses tumor growth in human lung cancer xenografts and prolongs survival of mice with lipopolysaccharide-induced septic shock. Int Immunopharmacol. Jul. 2014:21(10:208-19. doi:10.1016/j.intimp.2014.05.001. Epub May 14, 2014.
Sokolova et al., The use of calcium phosphate nanoparticles encapsulating Toll-like receptor ligands and the antigen hemagglutinin to induce dendritic cell maturation and T cell activation. Biomaterials. Jul. 2010;31(21):5627-33. doi:10.1016/j.biomaterials.2010.03.067. Epub Apr. 24, 2010.
Song et al., Backbone-modified oligonucleotides for tuning the cellular uptake behaviour of spherical nucleic acids. Biomater Sci. Feb. 28, 2017;5(3):412-416. doi: 10.1039/c6bm00792a.

(56) References Cited

OTHER PUBLICATIONS

Sood, 'Good cholesterol' nanoparticles seek and destroy cancer cells. The University of Texas MD Anderson Cancer Center. 2011. Downloaded Apr. 4, 2011. http://healthorbit.ca/newsdetail.asp?opt=1&nltid=164032911.
Stahl et al., Deregulated Akt3 activity promotes development of malignant melanoma. Cancer Res., 2004;64: 7002-10.
Stengel et al., Determinants for Membrane Fusion Induced by Cholesterol-Modified DNA Zippers, J. Phys. Chem. B., 112:8264-74 (2008).
Stengel et al., DNA-Induced Programmable Fusion of Phospholipid Vesicles, J. Am. Chem. Soc., 129:9584-5 (2007).
Stephenson et al., Inhibition of Rous sarcoma viral RNA translation by a specific oligodeoxyribonucleotide. Proc. Natl. Acad. Sci. USA, 1978;75(1): 285-8.
Stoeva et al., Multiplexed detection of protein cancer markers with biobarcoded nanoparticle probes. J. Am. Chem. Soc., 2006;128:8378-9.
Storhoff et al., One-pot colorimetric differentiation of polynucleotides with single base imperfections using gold nanoparticle probes. J. Am. Chem. Soc., 1998;120:1959-64.
Storhoff et al., Sequence-Dependent Stability of DNA-Modified Gold Nanoparticles. Langmuir. 2002;18: 6666-6670.
Storhoff et al., What controls the optical properties of DNA-linked gold nanoparticle assemblies? J. Am. Chem. Soc., 2000;122: 4640-50.
Storz et al., An abundance of RNA regulators. Annu. Rev. Biochem., 2005;74:199-217.
Stunz et al., Inhibitory oligonucleotides specifically block effects of stimulatory CpG oligonucleotides in B cells. Eur J Immunol. May 2002;32(5):1212-22.
Sugihara et al., One-pot synthesis of biomimetic shell cross-linked micelles and nanocages by ATRP in alcohol/water mixtures. Angew. Chem. Int. Ed. Engl., 2010;48(20):3500-3.
Sulkowski et al., The influence of temperature, cholesterol content and pH on liposome stability, J. Mol. Struct., 744-747: 737 (2005).
Sundaram et al., Particle-mediated delivery of recombinant expression vectors to rabbit skin induces high-titered polyclonal antisera (and circumvents purification of a protein immunogen). Nucl. Acids Res., 1996;24(7): 1375-7.
Switaj et al., CpG immunostimulatory oligodeoxynucleotide 1826 enhances antitumor effect of interleukin 12 gene-modified tumor vaccine in a melanoma model in mice. Clin Cancer Res. Jun. 15, 2004;10(12 Pt 1):4165-75.
Tan et al., Facile synthesis of hybrid silica nanocapsules by interfacial templating condensation and their application in fluorescence imaging. Chem. Commun. (Camb.), Nov. 2009; 7(41):6240-2.
Taton et al., Scanometric DNA array detection with nanoparticle probes. Science, 2000;289(5485):1757-60.
Thompson et al. Nano Lett. 10, 2690-2693 (Year: 2010).
Tincer et al., Immunostimulatory activity of polysaccharide-poly(I:C) nanoparticles. Biomaterials. Jun. 2011;32(18):4275-82. doi: 10.1016/j.biomaterials.2011.01.028.Epub Apr. 2, 2011.
Tiwari et at, Functionalized gold nanoparticles and their biomedical applications. Nanomaterials. 2011;1:31-63. doi: 10.3390/nano1010031.
Toh et al. Liposomes as sterile preparations and limitations of sterilisation techniques in liposomal manufacturing, Asian Journal of Pharmaceutical Sciences (2013) 8(2):88-95.
Tondelli et al., "Highly efficient cellular uptake of c-myb antisense oligonucleotides through specifically desianed polymeric nanospheres," Nucl. Acids Res. 26:5425-5431 (1998).
Tondelli, et al., Highly efficient cellular uptake of c-myb antisense oligonucleotides through specifically designed polymeric nanospheres. Nucl. Acids Res. 1998;26:5425-5431.
Tran et al., Targeting V600EB-Raf and Akt3 using nanoliposomal-small interfering RNA inhibits cutaneous melanocytic lesion development. Cancer Res. Sep. 15, 2008;68(18):7638-49. doi: 10.1158/0008-5472.CAN-07-6614.
Tripathy et al., High Density Lipoprotein Nanoparticles Deliver RNAi to Endothelial Cells to Inhibit Angiogenesis. Part Part Syst Charact. Nov. 1, 2014;31(11):1141-1150.
Trong et al., Mechanisms of micellization and rheology of PEO-PPO-PEO triblock copolymers with various architectures, J. Colloid Interface Sci. 328:278-87 (2008).
Turberfield et al., DNA fuel for free-running nanomachines. Phys. Rev. Lett., 2003;90: 118102.
Versluis et al., In situ modification of plain liposomes with lipidated coiled coil forming peptides induces membrane fusion, J. Am. Chem. Soc . . . 135:8057 (2013).
Virmani et al., Comparison of two different methods for inoculating VX2 tumors in rabbit livers and hind limbs. J. Vase. Interv. Radial., 2008;19(6):931-6.
Vorobjev et al., Nuclease resistance and RNase H sensitivity of oligonucleotides bridged by oligomethylenediol and oligoethylene glycol linkers. Antisense Nucleic Acid Drug Dev. Apr. 2001;11(2):77-85.
Wang et al., Co-delivery of drugs and DNA from cationic core-shell nanoparticles self-assembled from a biodegradable copolymer. Nat Mater. Oct. 2006;5(10):791-6. doi: 10.1038/nmat1737. Epub Sep. 24, 2006. PMID: 16998471.
Wang et al., Doxorubicin-tethered responsive gold nanoparticles facilitate intracellular drug delivery for overcoming multidrug resistance in cancer cells. ACS Nano. May 24, 2011;5(5):3679-92. doi: 10.1021/nn200007z. Epub Apr. 12, 2011.
Wang, Synthetic CPG ODNs activate immune cells through the Toll-like receptor (TLR) pathway. Integrated DNA Technologies. 2019.
Wei et al., Polyvalent immunostimulatory nanoagents with self-assembled CpG oligonucleotide-conjugated gold nanoparticles. Angew Chem Int Ed Engl. Jan. 27, 2012;51(5):1202-6. doi:10.1002/anie.201105187. Epub Dec. 21, 2011.
West et al., Recognition and signaling by toll-like receptors. Annu Rev Cell Dev Biol. 2006;22:409-37.
Whitehead et al., Knocking down barriers: advances in siRNA delivery, Nat. Rev. Drug. Discov., 8:129 (2009).
Willis et al., Liposome-Anchored Vascular Endothelial Growth Factor Aptamers. Bioconjugate Chem. 1998;9(5):573-82.
Wilson et al., pH-Responsive nanoparticle vaccines for dual-delivery of antigens and immunostimulatory oligonucleotides. ACS Nano. May 28, 2013;7(5):3912-25. doi: 10.1021/nn305466z. Epub Apr. 30, 2013.
Wilton et al. Antisense oligonucleotide-induced exon skipping across the human dystrophin gene transcript. Mol Ther. Jul. 2007;15(7):1288-96. Epub Feb. 6, 2007.
Wolfe et al., Modulation of Tetraplex Formation by Chemical Modifications of a G4-Containing Phosphorothioate Oligonucleotide. J. Am. Chem. Soc. 1996, 118, 6301-6302 (Year: 1996).
Wolfrum et al., Mechanisms and optimization of in vivo delivery of lipophilic siRNAs. Nat Biotechnol. Oct. 2007;25(10):1149-57. Epub Sep. 16, 2007.
Wu et al., DNA aptamer-micelle as an efficient detection/delivery vehicle toward cancer cells. Proc Natl Acad Sci U S A. Jan. 5, 2010;107(1):5-10. doi: 10.1073/pnas.0909611107. Epub Dec. 22, 2009.
Wu et al., Intracellular fate of spherical nucleic acid nanoparticle conjugates. J Am Chem Soc. May 28, 2014;136(21):7726-33. doi: 10.1021/ja503010a. Epub May 19, 2014.
Xia, Nanomaterials at work in biomedical research. Nat. Mater., 2008;7(10):758-60.
Xiao et al., Mannosylated bioreducible nanoparticle-mediated macrophage-specific TNF-.alpha. RNA interference for IBD therapy. Biomaterials. Oct. 2013;34(30):7471-82. doi: 10.1016/j.biomaterials. 2013.06.008. Epub Jun. 29, 2013.
Xing et al., Selective delivery of an anticancer drug with aptamer-functionalized liposomes to breast cancer cells in vitro and in vivo, J. Mater. Chem. B., 1:5288 (2013).
Xu et al., Thermodynamics of DNA hybridization on gold nanoparticles. J. Am. Chem. Soc., 2005;127(38): 13227-31.
Yamamoto et al., Unique palindromic sequences in synthetic oligonucleotides are required to induce IFN [correction of INF] and

(56) References Cited

OTHER PUBLICATIONS augment IFN-mediated [correction of INF] natural killer activity. J Immunol. Jun. 15, 1992;148(12):4072-6.

Yang et al., Biomimetic, synthetic HDL nanostructures for lymphoma. Proc Natl Acad Sci U S A. Feb. 12, 2013;110(7):2511-6. doi: 10.1073/pnas.1213657110. Epub Jan. 23, 2013.

Yang et al., Evidence that processed small dsRNAs may mediate sequence-specific mRNA degradation during RNAi in *Drosophila* embryos. Curr. Biol., 2000;10: 1191-200.

Yang et al., Inhibition of a C-rich oligodeoxynucleotide on activation of immune cells in vitro and enhancement of antibody response in mice. Immunology. Dec. 2010;131(4):501-12. doi: 10.1111/j.1365-2567.2010.03322.x.

Yin et al., Supramolecular self-assembled nanoparticles mediate oral delivery of therapeutic TNF-.alpha. siRNA against systemic inflammation. Angew Chem Int Ed Engl. May 27, 2013;52(22):5757-61. doi: 10.1002/anie.201209991. Epub Apr. 22, 2013.

Yin Win et al., Effects of particle size and surface coating on cellular uptake of polymeric nonparticles for oral delivery of anticancer drugs. Biomaterials, 2005;26: 2713-22.

Zabner et al., Cellular and molecular barriers to gene transfer by a cationic lipid. J. Biol. Chem., 1995;270: 18997-9007.

Zamecnik et al., Inhibition of Rous sarcoma virus replication and cell transformation by a specific oligodeoxynucleotide. Proc. Natl. Acad. Sci. USA, 1978;75(1): 280-4.

Zamore et al., RNAi: double-stranded RNA directs the ATP-dependent cleavage of mRNA at 21 to 23 nucleotide intervals. Cell, Mar. 31, 2000;101: 25-33.

Zhang et al., A general approach to DNA-programmable atom equivalents. Nature Materials. Aug. 2013;12(8):741-6.

Zhang et al., An extremely stable and orthogonal DNA base pair with a simplified three-carbon backbone. J. Am. Chem. Soc., 2005;127:74-75.

Zhang et al., Antibody-linked spherical nucleic acids for cellular targeting, J. Am. Chem. Soc., 134:16488-91 (2012).

Zhang et al., Biomimetic nanocarrier for direct cytosolic drug delivery. Angew Chem Int Ed Engl. 2009;48(48):9171-5.

Zhang et al., Cationic shell-crosslinked knedel-like nanoparticles for highly efficient gene and oligonucleotide transfection of mammalian cells. Biomaterials, 2009;30(5):968-77.

Zhang et al., Informational liposomes: Complexes derived from cholesteryl-conjugated oligonucleotides and liposomes. Tetrahedron Letters. 1996. 37(35):6243-6.

Zhang et al., Nanopod formation through gold nanoparticle templated and catalyzed cross-linking of polymers bearing pendant propargyl ethers. J Am Chem Soc. Nov. 3, 2010;132(43):15151-3.

Zhang et al., Non-invasive multimodal functional imaging of the intestine with frozen micellar naphthalocyanines, Nat. Nanotechnol. 9:631-8 (2014).

Zhang et al., Structure-activity relationships of cationic shell-crosslinked knedel-like nanoparticles: shell composition and transfection efficiency/cytotoxicity, Biomaterials, 31:1805 (2010).

Zhang et al., TLR9-mediated siRNA delivery for targeting of normal and malignant human hematopoietic cells in vivo. Blood. Feb. 21, 2013;121(8):1304-15. doi: 10.1182/blood-2012-07-442590. Epub Jan. 3, 2013.

Zheng et al., A spherical nucleic acid platform based on self-assembled DNA biopolymer for high-performance cancer therapy. ACS Nano. Aug. 27, 2013;7(8):6545-54. doi: n402344v. Epub Jul. 23, 2013.

Zheng et al., Sterically controlled docking of gold nanoparticles on ferritin; surface by DNA hybridization. Nanotechnology. Jul. 8, 2011;22(27):275312. doi:; 10.1088/0957-4484/22/27/275312. Epub May 26, 2011.

Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas.1118425109. Epub Jul. 6, 2012.

Zimmer, Antisense oligonucleotide delivery with polyhexylcyanoacrylate nanoparticles as carriers. Methods, 1999;18: 286-95.

Zimmermann, et al., A Novel Silver(1)-Mediated DNA Base Pair. J. Am. Chem. Soc., 2002; 124:13684-13685.

Aryan et al., A New Era of Targeting the Ancient Gatekeepers of the Immune System: Toll-Like Agonists in the Treatment of Allergic Rhinitis and Asthma. International Archives of Allergy and Immunology. 2014;164:46-63. Epub May 21, 2014.

Bakker et al., Identification of a novel peptide derived from the melanocyte-specific gp100 antigen as the dominant epitope recognized by an HLA-A2.1-restricted anti-melanoma CTL line. Int J Cancer. Jul. 4, 1995;62(1):97-102. doi: 10.1002/ijc.2910620118.

Chan et al., Lipid-anchored DNA mediates vesicle fusion as observed by lipid and content mixing. Biointerphases. Jun. 2008;3(2):FA17. doi: 10.1116/1.2889062.

De Titta et al., Nanoparticle conjugation of CpG enhances adjuvancy for cellular immunity and memory recall at low dose. Proc Natl Acad Sci U S A. Dec. 3, 2013;110(49):19902-7. doi: 10.1073/pnas.1313152110. Epub Nov. 18, 2013.

Eisenhauer et al., New response evaluation criteria in solid tumours: revised RECIST guideline (version 1.1). Eur J Cancer. Jan. 2009;45(2):228-47. doi: 10.1016/j.ejca.2008.10.026. Epub Dec. 22, 2008.

Fang et al., Cancer cell membrane-coated nanoparticles for anticancer vaccination and drug delivery. Nano Lett. 2014;14(4):2181-8. Doi: 10.1021/nl500618u. Epub Mar. 28, 2014.

Goldberg, Immunoengineering: how nanotechnology can enhance cancer immunotherapy. Cell. Apr. 9, 2015;161(2):201-4. Doi: 10.1016/j.cell.2015.03.037.

Hirosue et al., Antigen delivery to dendritic cells by poly(propylene sulfide) nanoparticles with disulfide conjugated peptides: Cross-presentation and T cell activation. Vaccine. Nov. 23, 2010;28(50):7897-906. Doi: 10.1016/j.vaccine.2010.09.077. Epub Oct. 8, 2010.

Israelachvili et al., Physical principles of membrane organization. Q Rev Biophys. May 1980;13(2):121-200. doi: 10.1017/s0033583500001645.

Kim et al., pH-responsive biodegradable assemblies containing tunable phenyl-substituted vinyl ethers for use as efficient gene delivery vehicles. ACS Appl Mater Interfaces. Jun. 26, 2013;5(12):5648-58. Doi: 10.1021/am400977t. Epub Jun. 17, 2013. Author Manuscript, 28 pages.

Klinman et al., CpG motifs as immune adjuvants. Vaccine. Jan. 1999;17(1):19-25. Doi: 10.1016/s0264-410x(98)00151-0.

Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004;27(6):460-71. doi: 10.1097/00002371-200411000-00006.

Krieg, CpG still rocks! Update on an accidental drugj. Nucleic Acid Ther. Apr. 2012;22(2):77-89. doi: 10.1089/nat.2012.0340. Epub Feb. 21, 2012.

Liu et al., Structure-based programming of lymph-node targeting in molecular vaccines. Nature. Mar. 27, 2014;507(7493):519-22. Doi: 10.1038/nature12978. Epub Feb. 16, 2014. Author Manuscript, 23 pages.

Ming et al., Bioconjugates for targeted delivery of therapeutic oligonucleotides. Adv Drug Deliv Rev. Jun. 29, 2015;87:81-9. doi: 10.1016/j.addr.2015.02.002. Epub Feb. 15, 2015.

Perrault et al., Mediating tumor targeting efficiency of nanoparticles through design. Nano Lett. May 2009;9(5):1909-15. Doi: 10.1021/n1900031y.

Radovic-Moreno et al., Immunomodulatory spherical nucleic acids. Proc Natl Acad Sci U S A PNAS. Mar. 31, 2015;112(13):3892-7. doi: 10.1073/pnas.1502850112. Epub Mar. 16, 2015.

Raouane et al., Lipid conjugated oligonucleotides: a useful strategy for delivery. Bioconjug Chem. Jun. 20, 2012;23(6):1091-104. doi: 10.1021/bc200422w. Epub Mar. 15, 2012.

Samadikhah et al., Preparation, characterization, and efficient transfection of cationic liposomes and nanomagnetic cationic liposomes. Int J Nanomedicine. 2011;6:2275-83. doi: 10.2147/IJN.S23074. Epub Oct. 12, 2011.

Sharpe, Mechanisms of costimulation. Immunol Rev. May 2009;229(1):5-11. doi: 10.1111/j.1600-065X.2009.00784.x.

(56) References Cited

OTHER PUBLICATIONS

Thompson et al., Safety and Efficacy of PF-3512676 for the Treatment of Stage IV Renal Cell Carcinoma: An Open-Label, Multicenter Phase I/II Study. Clinical Genitourinary Cancer. Oct. 1, 2009;7(3):E58-65.
Townson et al., Re-examining the size/charge paradigm: differing in vivo characteristics of size- and charge-matched mesoporous silica nanoparticles. J Am Chem Soc. Oct. 30, 2013;135(43):16030-3. doi: 10.1021/ja4082414. Epub Oct. 16, 2013. Author Manuscript, 13 pages.
U.S. Appl. No. 18/019,857, filed Feb. 6, 2023, Anderson et al.
U.S. Appl. No. 18/020,501, filed Feb. 9, 2023, Anderson et al.

MULTIVALENT DELIVERY OF IMMUNE MODULATORS BY LIPOSOMAL SPHERICAL NUCLEIC ACIDS FOR PROPHYLACTIC OR THERAPEUTIC APPLICATIONS

RELATED APPLICATIONS

This application is a continuation of U.S. application Ser. No. 16/569,007, filed Sep. 12, 2019, which is a continuation of U.S. application Ser. No. 15/315,538, filed Dec. 1, 2016, which is a national stage filing under 35 U.S.C. § 371 of International Application No. PCT/US2015/034226, filed Jun. 4, 2015, which claims the benefit of the filing date priority under 35 U.S.C. § 119(e) to U.S. Provisional Application Ser. No. 62/007,528, entitled "MULTIVALENT DELIVERY OF IMMUNE MODULATORS BY LIPOSOMAL SPHERICAL NUCLEIC ACIDS FOR PROPHYLACTIC OR THERAPEUTIC APPLICATIONS" filed on Jun. 4, 2014, the entire contents of each of which are herein incorporated by reference in their entireties.

NAMES OF PARTIES TO A JOINT RESEARCH AGREEMENT

The inventions disclosed herein were made pursuant to a joint research agreement between Exicure Inc., now named Exicure Operating Company, and Northwestern University.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Aug. 18, 2021, is named A110770003US3-SEQ-DQB and is 5,636 bytes in size.

BACKGROUND OF THE INVENTION

The immune system is a complex network of cellular and humoral components that act in concert to recognize foreign and potentially dangerous substances in the body and eliminate them in a highly targeted and controlled fashion. It can generally be divided into the innate and adaptive immune systems. The innate immune system is germline encoded and is designed to respond to conserved motifs present on pathogens. The adaptive immune system develops its antigen specificity repertoire through controlled somatic recombination processes and can respond with exquisite specificity to a wide variety of antigen types. Stimulating innate and adaptive immune responses have been shown to be an effective strategy to treat or prevent a wide variety of diseases in animals, animal disease models, and humans.

The success of immunomodulatory approaches in treating or preventing a variety of infectious diseases has been extraordinary. Despite this, there are potentially many more diseases that could be addressed using an immunotherapy approach. Two critical limitations remain: (1) properly priming innate immune cells with the right signals delivered at the optimal time and in optimal ratios to safely boost their function while also providing a suitable environment for inducing an adaptive immune response, and (2) identifying the right antigen or combination of antigens that should be targeted by the adaptive response.

Current approaches for stimulating an immune response largely depend on mixtures of compounds that are known to be immunomodulatory in isolation. At present, compounds that are used in the clinic are bulk mixtures of immune stimulants, optionally combined with antigens, which have been empirically determined to induce innate and adaptive immune responses, respectively. Despite almost a century of development, conventional approaches have yielded only two FDA approved immune stimulants: (1) alum, which is a combination of aluminum salts, and (2) monophosphoryl lipid A. While alum in particular has an impressive track record of safety and efficacy in infectious diseases, it is becoming increasingly clear that these agents do not appear sufficient to induce effective immune responses to combat more complex diseases, such as intracellular pathogens, cancer, allergies, and allergic diseases, among others. Efforts to develop new immunostimulants have largely been unsuccessful, primarily due to lack of efficacy or due to safety concerns.

The immune system evolved over millennia to respond to pathogens such as bacteria, viruses, fungi, and helminths. Consequently, most immune cells are optimized to recognize, phagocytose, process, and then respond to motifs present on microorganisms and have receptors that are "tuned" to the ratios typically present on these organisms.

SUMMARY OF THE INVENTION

Liposomal spherical nucleic acids that function as multivalent immune modulators are provided according to aspects of the invention. The invention is based, in some aspects, on a nanostructure, comprising a liposomal core having a lipid bilayer, wherein an immune stimulant or an immune suppressor is associated with the lipid bilayer, and oligonucleotides positioned on the exterior of the liposomal core.

In some embodiments the nanostructure comprises a liposomal core having a lipid bilayer, wherein an immune stimulant or an immune suppressor is associated with the lipid bilayer, and oligonucleotides positioned on the exterior of the liposomal core, wherein the oligonucleotides form an oligonucleotide shell.

In other embodiments the nanostructure comprises a liposomal core having a lipid bilayer, wherein an immune stimulant or an immune suppressor is associated with the lipid bilayer, and oligonucleotides positioned on the exterior of the liposomal core, wherein the oligonucleotides form an oligonucleotide shell, wherein the oligonucleotide shell is comprised of at least one pattern recognition receptor modulating oligonucleotide.

In some embodiments the nanostructure comprises a liposomal core having a lipid bilayer, wherein an immune stimulant or an immune suppressor is associated with the lipid bilayer, and oligonucleotides positioned on the exterior of the liposomal core, wherein the oligonucleotides form an oligonucleotide shell, wherein the oligonucleotide shell is comprised of at least one pattern recognition receptor modulating oligonucleotide, wherein the pattern recognition receptor modulating oligonucleotide is a TLR agonist.

In other embodiments the nanostructure comprises a liposomal core having a lipid bilayer, wherein an immune stimulant or an immune suppressor is associated with the lipid bilayer, and oligonucleotides positioned on the exterior of the liposomal core, wherein the oligonucleotides form an oligonucleotide shell, wherein the oligonucleotide shell is comprised of at least one pattern recognition receptor modulating oligonucleotide, wherein the pattern recognition receptor modulating oligonucleotide is a TLR antagonist.

In other embodiments the TLR is selected from the group consisting of TLR3, TLR 7, TLR8, TLR9, and TLR13.

In some embodiments the nanostructure comprises a liposomal core having a lipid bilayer, wherein an immune stimulant or an immune suppressor is associated with the lipid bilayer, and oligonucleotides positioned on the exterior of the liposomal core, wherein the oligonucleotides form an oligonucleotide shell, wherein the oligonucleotide shell is comprised of at least one pattern recognition receptor modulating oligonucleotide, wherein the pattern recognition receptor modulating oligonucleotide is a RIG-I agonist.

In other embodiments the nanostructure comprises a liposomal core having a lipid bilayer, wherein an immune stimulant or an immune suppressor is associated with the lipid bilayer, and oligonucleotides positioned on the exterior of the liposomal core, wherein the oligonucleotides form an oligonucleotide shell, wherein the oligonucleotide shell is comprised of at least one pattern recognition receptor modulating oligonucleotide, wherein the pattern recognition receptor modulating oligonucleotide is a RIG-I antagonist.

In some embodiments the oligonucleotide shell is comprised of oligonucleotides and a carrier molecule.

In other embodiments wherein the oligonucleotide shell is comprised entirely of oligonucleotides.

In some embodiments the oligonucleotides are comprised of single-stranded or double-stranded DNA oligonucleotides.

In other embodiments the oligonucleotides are comprised of single-stranded or double-stranded RNA oligonucleotides.

In other embodiments the oligonucleotides are comprised of chimeric RNA-DNA oligonucleotides.

In another embodiment the oligonucleotides are comprised of combinations of single-stranded or double-stranded DNA, RNA, or chimeric RNA-DNA oligonucleotides.

In another embodiment the oligonucleotides of the oligonucleotide shell have structurally identical oligonucleotides.

In some embodiments the oligonucleotides of the oligonucleotide shell have at least two structurally different oligonucleotides.

In other embodiments the oligonucleotides of the oligonucleotide shell have 2-10 different nucleotide sequences.

In some embodiments the oligonucleotides have at least one phosphorothioate linkage.

In other embodiments the oligonucleotides do not have a phosphorothioate linkage.

In another embodiment the nanostructure comprises a liposomal core having a lipid bilayer, wherein an immune stimulant or an immune suppressor is associated with the lipid bilayer, and oligonucleotides positioned on the exterior of the liposomal core, wherein the oligonucleotides comprise CpG-motif containing oligonucleotides.

In some embodiments the CpG oligonucleotides are selected from the group consisting of A-class, B-class and C-class CpG oligonucleotides.

In another embodiment the nanostructure comprises a liposomal core having a lipid bilayer, wherein an immune stimulant or an immune suppressor is associated with the lipid bilayer, and oligonucleotides positioned on the exterior of the liposomal core, wherein the oligonucleotides comprise immunostimulatory single-stranded or double-stranded RNA.

In some embodiments at least one oligonucleotide has its 5'-terminus exposed to the outside surface of the nanostructure.

In other embodiments all of the oligonucleotides have their 5'-terminus exposed to the outside surface of the nanostructure.

In another embodiment the oligonucleotides are directly linked to the liposomal core.

In some embodiments the oligonucleotides are indirectly linked to the liposomal core through a linker.

In other embodiments the oligonucleotides are indirectly linked to the liposomal core through more than one linker.

In another embodiment the linker is one or more of the following linkers: tocopherols, sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, polyunsaturated sterols of different lengths, saturation states, saturated C8-C22 fatty acids, saturated C8-C22 ether derivatives of glycerol, saturated and unsaturated amide derivatives of C8-C22 fatty acids and mono- and 1,2- or 1, 3-di-amino glycerols and derivatives thereof.

In another embodiment the oligonucleotides comprise 2-1,000 oligonucleotides.

In some embodiments the liposomal core is comprised of one or more lipids selected from: sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, saturated C8-C22 fatty acids, saturated C8-C22 ether derivatives of glycerol, and saturated and unsaturated amide derivatives of C8-C22 fatty acids and mono- and 1,2- or 1,3-di-amino glycerols and derivatives thereof.

In another embodiment the liposomal core is comprised of one type of lipid.

In some embodiments the liposomal core is comprised of 2-10 different lipids.

In other embodiments wherein the immune stimulant is selected from the group consisting of monophosphoryl lipid A, lipid A from bacterial origin, 22:0 trehalose, dimethyl-dioctadecyl-ammonium, Kdo2 lipid A, inositol phosphates including IP3(1,3,4), IP3(1,3,5), IP3(1,4,5), IPR(1,3,4,5), LPA/S1P receptor selective agonists, PAF and PAF analogs, liponucleotides, cyclic LPA, bioactive ceramides, endocannabinoids, anandamides, lipid oxidation products, diacylglycerol phosphate, bacterial membrane lipids, N-acylglycine lipids, acyl carnitine lipids, mycolic acids, plant lipid extracts, FSL-1, PAM3CSK4, HKLM, LPS, FLA-ST, imiquimod, resiquimod, C12-IE-DAP, L18-MDP toll like receptor agonists, NOD receptor agonists, and pro-inflammatory immune receptor agonists.

In another embodiment the nanostructure further comprises an antigen.

In some embodiments the antigen is mixed together with the nanostructure.

In other embodiments the antigen is linked directly to the oligonucleotide shell.

In some embodiments the antigen is linked indirectly to the oligonucleotide shell through a linker.

In other embodiments the antigen is linked directly to the liposomal core.

In yet another embodiment the antigen is linked indirectly to the liposomal core through a linker.

In another embodiment wherein an antigen-oligonucleotide conjugate is linked to the liposomal core through oligonucleotide hybridization.

In some embodiments the nanostructure comprises a liposomal core having a lipid bilayer, wherein an immune stimulant or an immune suppressor is associated with the lipid bilayer, and oligonucleotides positioned on the exterior of the liposomal core, wherein the immune stimulant is associated with the liposomal core by being embedded within the liposomal core.

In other embodiments the nanostructure comprises a liposomal core having a lipid bilayer, wherein an immune stimulant or an immune suppressor is associated with the lipid bilayer, and oligonucleotides positioned on the exterior of the liposomal core, wherein the immune stimulant is associated with the liposomal core by being linked indirectly to the liposomal core.

In some embodiments the nanostructure comprises a liposomal core having a lipid bilayer, wherein an immune stimulant or an immune suppressor is associated with the lipid bilayer, and oligonucleotides positioned on the exterior of the liposomal core, wherein the immune stimulant is associated with the liposomal core by being linked directly to the liposomal core.

In some embodiments the nanostructure comprises a liposomal core having a lipid bilayer, wherein an immune stimulant or an immune suppressor is associated with the lipid bilayer, and oligonucleotides positioned on the exterior of the liposomal core, wherein the oligonucleotides form an oligonucleotide shell, wherein the oligonucleotides of the oligonucleotide shell are oriented radially outwards.

In other embodiments the linker is selected from the group consisting of tocopherols, sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, saturated C8-C22 fatty acids, saturated C8-C22 ether derivatives of glycerol, saturated and unsaturated amide derivatives of C8-C22 fatty acids and mono- and 1,2- or 1,3-di-amino glycerols, and derivatives thereof.

In some embodiments the antigen is encapsulated within the liposomal core in an inner aqueous layer.

In other embodiments the antigen is attached non-covalently to the oligonucleotide of the oligonucleotide shell.

In other embodiments the antigen is selected from the group consisting of a cancer antigen, a bacterial antigen, a viral antigen, a parasitic antigen, a hapten, and an allergen.

In some embodiments the nanostructure is a self-assembling nanostructure.

Another aspect of the invention comprises a method for treating a subject, comprising administering to a subject a nucleic acid nanostructure in an effective amount to promote an immune response.

In one embodiment the subject has a disorder and wherein the method is a method for treating the disorder.

In another embodiment the disorder is cancer.

In some embodiments the disorder is infectious disease.

In other embodiments the infectious disease is a viral infection.

In some embodiments the infectious disease is a bacterial infection.

In another embodiment the disorder is allergy.

In some embodiments the disorder is asthma.

In another embodiment the disorder is autoimmune disease.

In some embodiments further comprising administering a therapeutic protocol to the subject.

In another embodiment the therapeutic protocol is surgery.

In some embodiments the therapeutic protocol is radiation.

In other embodiments the therapeutic protocol is a medicament.

In one embodiment the method further comprises administering an adjuvant.

In one embodiment the subject has a disorder and wherein the method is a method for treating the disorder, wherein the nanostructure is associated with a targeting molecule.

In one embodiment the subject has a disorder and wherein the method is a method for treating the disorder, wherein the nanostructure is delivered by a route selected from the group consisting of oral, nasal, sublingual, intravenous, subcutaneous, mucosal, respiratory, direct injection, enema, and dermally.

In another aspect the composition for use in the treatment of disease comprises the nucleic acid nanostructure and embodiments thereof.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. The details of one or more embodiments of the invention are set forth in the accompanying Detailed Description, Examples, Claims, and Figures. Other features, objects, and advantages of the invention will be apparent from the description and from the claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 7A shows NF-kB activation and FIG. 7B shows TNF (OD). One-way ANOVA ****$p<0.0001$.

DETAILED DESCRIPTION OF CERTAIN EMBODIMENTS OF THE INVENTION

Toll-like receptors (TLRs) are a family of pattern recognition receptors (PRRs) that trigger activation of innate immune cells, promoting their effector functions and bridging innate and adaptive immunity. Agents that stimulate TLRs are being investigated extensively as potential therapeutic and prophylactic compounds due to the central role these receptors play in coordinating immune responses. Similar to the way that multiple TLRs and immune receptors are stimulated when an immune cell processes a pathogen, it has been shown that stimulation of multiple TLRs with multiple compounds can yield greater efficacy. However, effectively delivering multiple TLR agonists in combination can be quite difficult for a number of reasons: (1) synergy is often observed only in a narrow window of fixed concentration ratios between the two compounds, due to their typically different IC50 or EC50 values, (2) different physicochemical properties such as different size, charge, and hydrophobicity can make attaching them to each other difficult or make them have drastically different PK/PD/ADME properties, (3) the toxic levels of the compounds tend to be different, and (4) the target receptors of one or more of the different compounds may be inaccessible, such as the cytosol, or located in a degradative compartment, such as endosomes or lysosomes.

Figure 1:
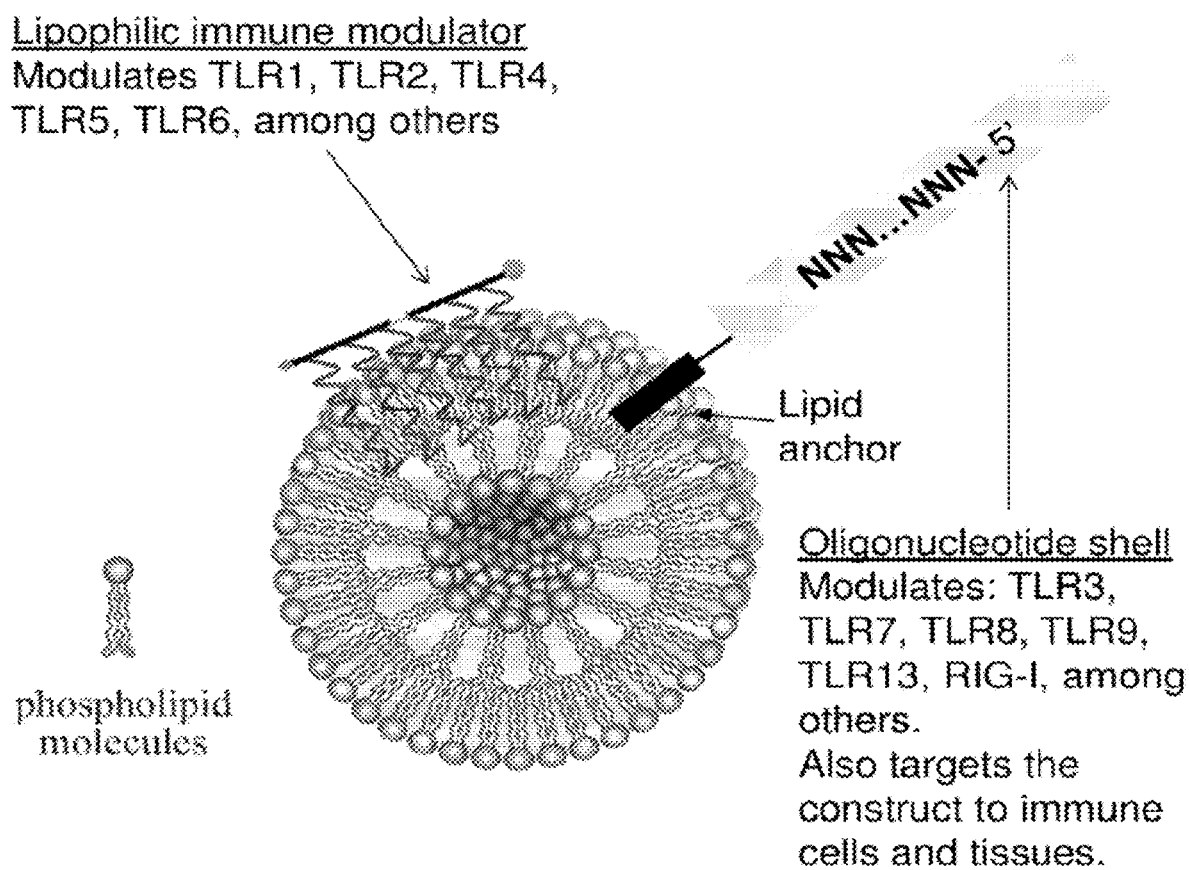
FIG. 1 shows a general structure of an exemplary liposomal nanostructure of the invention for co-delivery of oligonucleotide and lipophilic immune stimulants. The nanostructure includes: (1) a liposomal core, which contains lipophilic immune stimulants (TLR1, TLR2, TLR4, TLR5, TLR6, among others) attached to and possibly embedded in the lipid bilayer, and (2) an oligonucleotide shell, which has dual function in that it helps target the entire construct to immune cells and also acts to stimulate immune receptors that can recognize nucleic acids (TLR3, TLR7, TLR8, TLR9, TLR13, RIG-I, among others).
Figure 2:
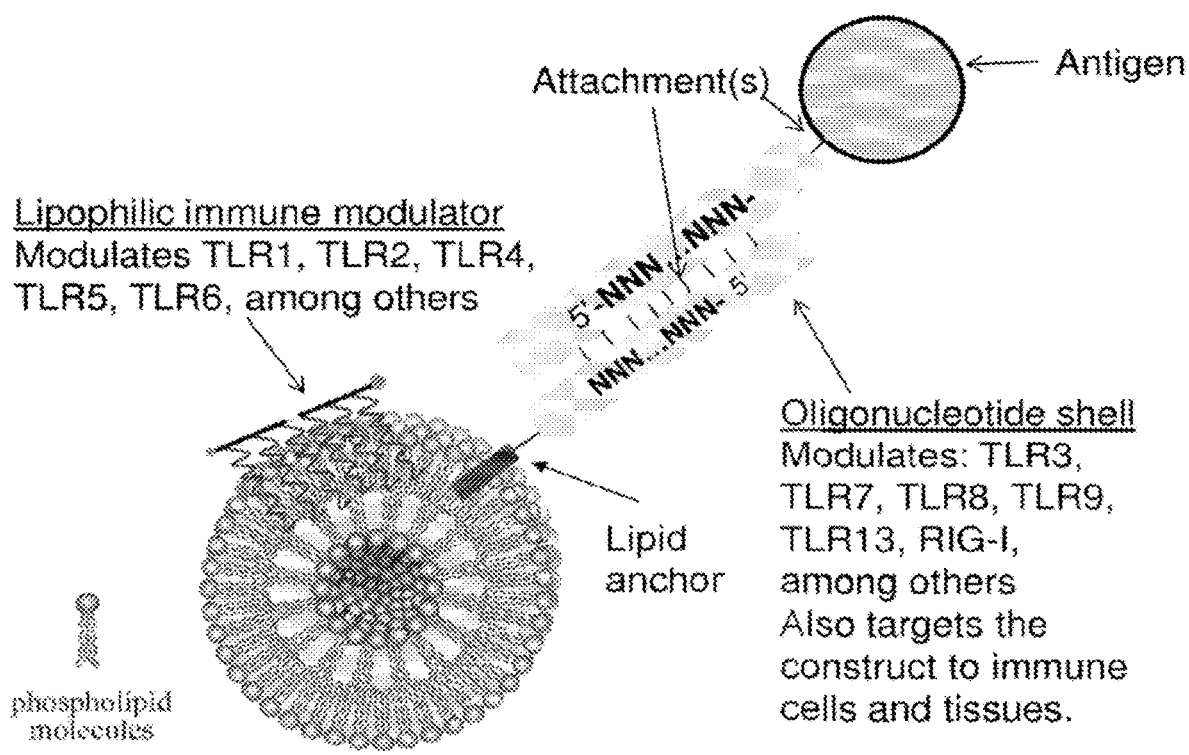
FIG. 2 shows a general structure of another exemplary antigen-conjugated liposomal nanostructure for co-delivery of oligonucleotide and lipophilic immune stimulants and antigen. The construct is similar to that shown in FIG. 1 but includes an additional modification whereby an antigen-conjugated oligonucleotide is attached non-covalently to the parent structure. The antigen is conjugated to the liposomal SNA via interactions with the oligonucleotide shell.
Figure 3:
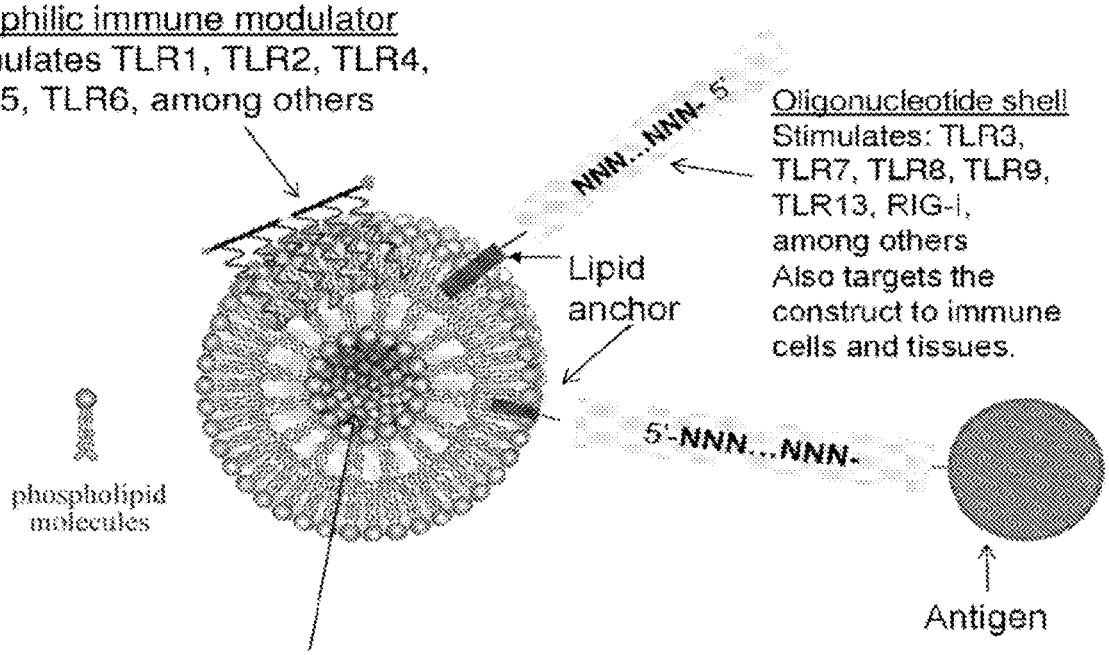
FIG. 3 shows another general structure of antigen-conjugated liposomal nanostructure for co-delivery of oligonucleotide and lipophilic immune stimulants and antigen. The antigen may also be encapsulated in the liposomal core.
Figure 6A:
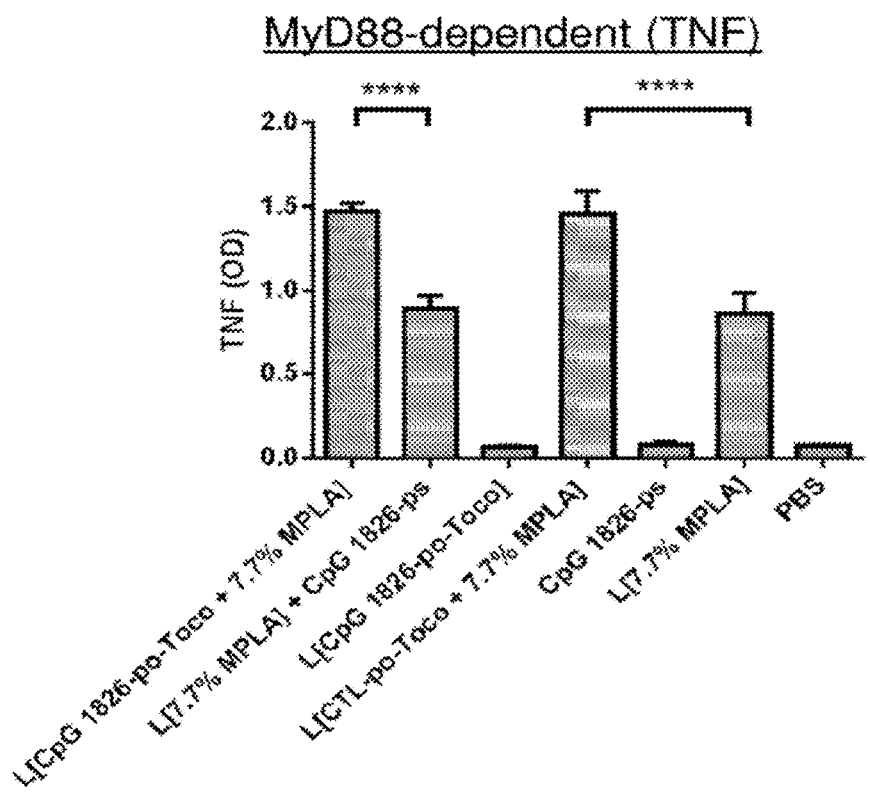
FIGS. 6A-6B are a set of bar graphs showing that nanostructure co-delivery of CpG and MPLA optimally activates both MyD88-dependent and -independent pathways. Liposomal nanostructures that deliver both CpG 1826 and MPLA in a single construct demonstrate elevated TNF (FIG. 6A) and IFN-alpha (FIG. 6B) levels that cannot be replicated either by delivering each in isolation, or by delivering both components in the same well but not on the same construct. ANOVA, $p<0.01$, **$p<0.0001$.
Figure 6B:
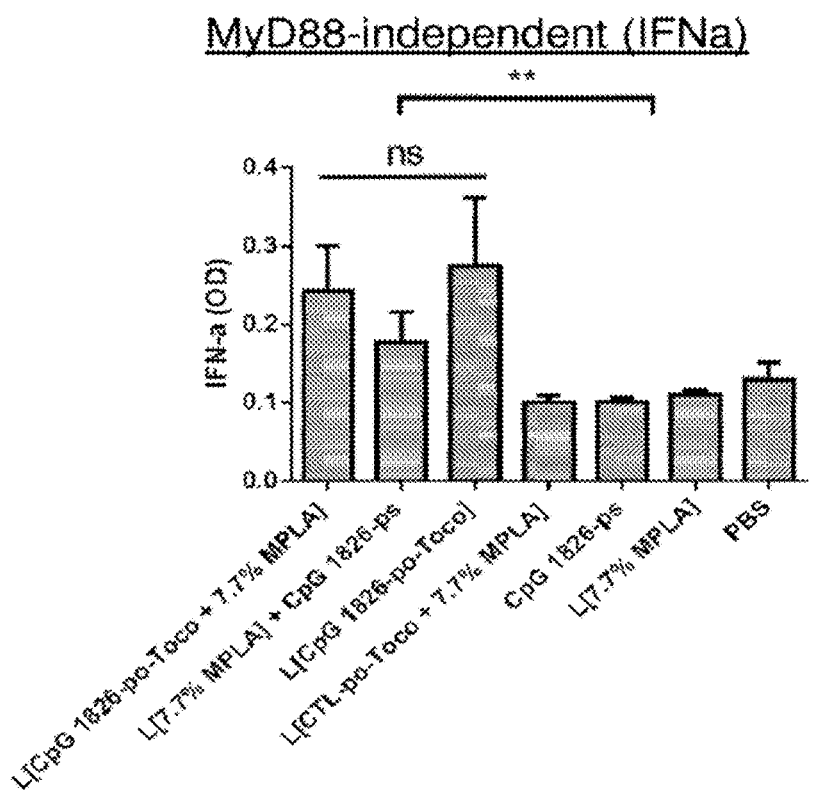
Figure 7A:
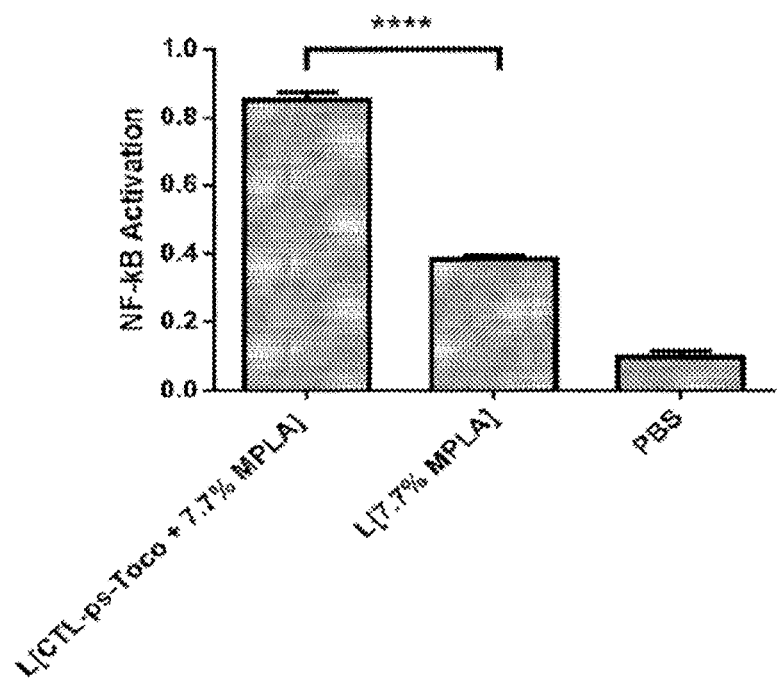
FIGS. 7A-7B are a set of bar graphs showing liposomal nanostructure delivery of MPLA improves activation of NF-kB even without CpG motif.
Figure 7B:
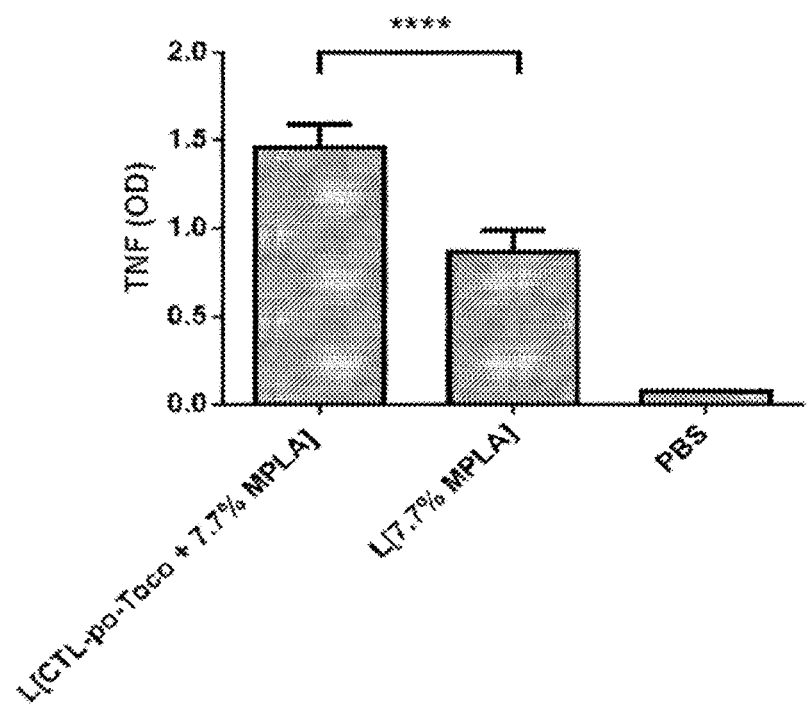

A novel class of nanostructures having unexpectedly high immune modulating activity have been developed according to the invention. These nanostructures are supra-molecular assemblies, which are immune-modulating liposomal spherical nucleic acids (sometimes referred to as SNAs). These nanostructures can deliver combinations of immune modulating materials in a highly spatiotemporally controlled manner to cells (Examples are shown in FIGS. 1-3). A distinctive feature of these nanostructures is the incorporation of immune modulating materials both within the external shell as well as within the core, which work in concert to achieve unexpected immune modulating effects in terms of the magnitude and quality of the immune response. These immunomodulating effects cannot be achieved by delivering the materials individually or in combination but not physically associated together in the same construct. It has been demonstrated according to the invention that the assembly of all components into a single structure is vital to achieving optimal effects (Data is shown in FIGS. 6-7).

In addition to the above, a method for achieving co-delivery of antigen with the multivalent immune-modulating structures was also developed (Examples are depicted in FIGS. 2-3). This enables these constructs to deliver both antigenic and co-stimulatory signals to bridge innate and adaptive immunity to induce robust immune responses against a variety of diseases (stimulatory application) or to elicit antigen-specific tolerance by delivering antigen in the absence of co-stimulation, achieved by lack of a stimulatory signal or by blocking immune signaling with antagonist molecules, leading to effector cell anergy or induction of regulatory T cells (regulatory application).

Currently, methods used in the clinic to induce immunologic effects generally fall into two categories: 1) compounds that activate or potentiate immune responses, such as vaccines and adjuvants, small molecule agonists of toll-like receptors such as imiquimod and resiquimod, or oligonucleotides such as ISS 1018 (Dynavax Technologies Corporation), among several others, and 2) compounds that act to reduce unwanted immune responses, such as corticosteroids, cyclosporine, and tacrolimus. These compounds have significant limitations known to those in the art.

Figure 12:
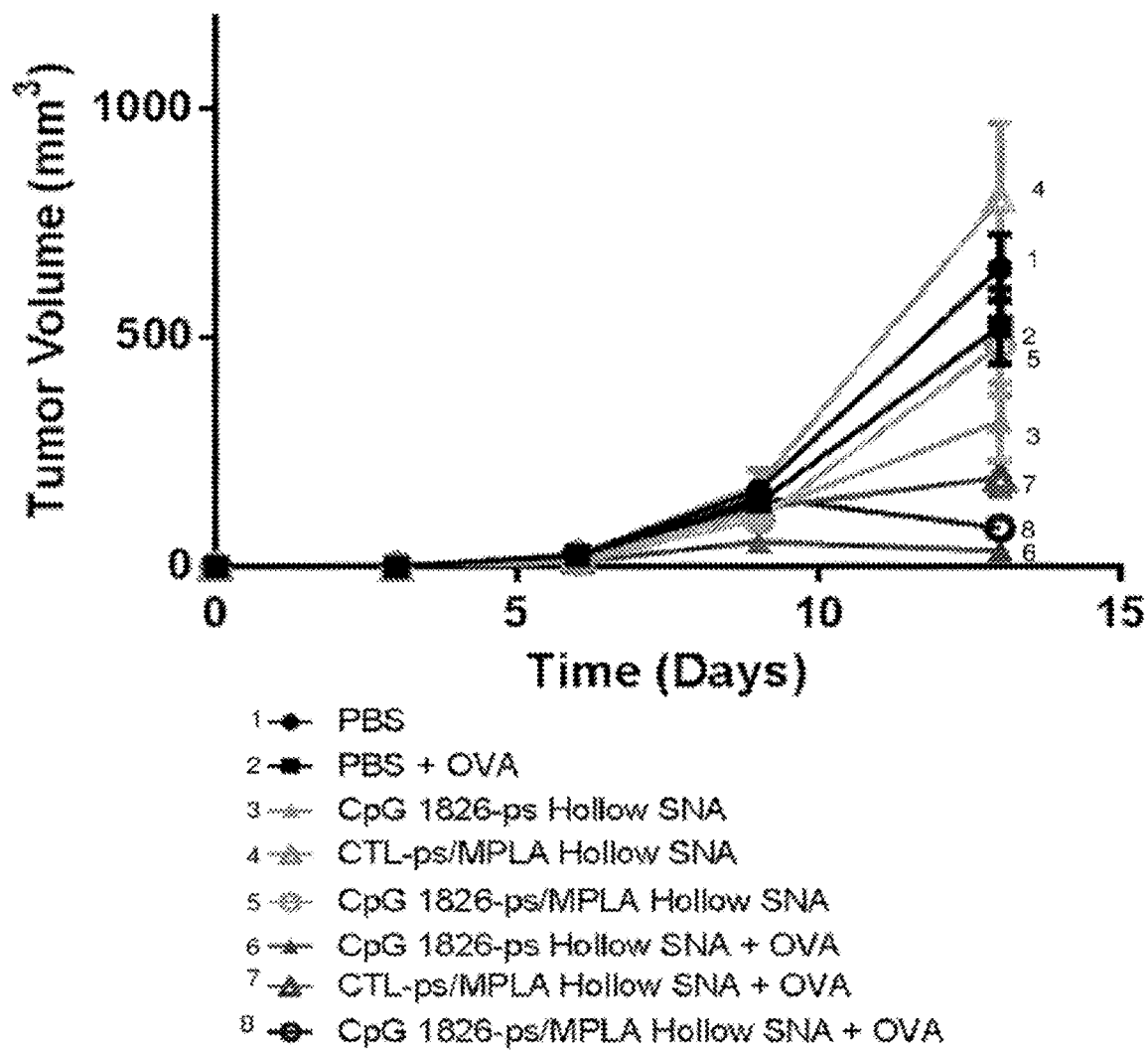
FIG. 12 is a graph showing that hollow nanostructures with antigen reduce tumor growth rates. C57BL/6 mice (N=10/group) were inoculated with $1\times10^6$ E.G7-OVA cells on day 0 then treated with the indicated compounds on days 3, 7, 10.

In general, immune stimulation attempts in the prior art have been limited by a lack of ability to activate robust cellular immune responses to target antigen, leading to failures to develop efficacious and cost-effective vaccines for various infectious diseases, such as HIV, tuberculosis, malaria, dengue, chlamydia, and others. Similarly, various experimental vaccine compounds for cancer have failed to reach their primary end point in late stage clinical trials. A key challenge that does not yet appear to be satisfactorily met is a formulation of antigen and immune stimulant that can achieve superior results. The nanostructure of the invention achieved these goals, producing activation of strong cellular responses to antigen in vivo with evidence of significant (95%) reduction of tumor burden (FIG. 12).

The nanostructure of the invention include: (1) a liposomal core having a lipid bilayer, which contains an immune stimulant embedded in or attached to the lipid bilayer, and (2) a layer of oligonucleotides, which may be an oligonucleotide shell, and which have dual function in that they help to target the nanostructure to immune cells and also act to stimulate immune receptors that can recognize nucleic acids (FIG. 1). Antigen may also be coupled to this construct, such that it will be delivered together with the co-stimulatory signals (FIG. 2). A similar construct to that shown in FIG. 1 undergoes an additional modification whereby an antigen-conjugated oligonucleotide is attached to the nanostructure. Alternatively or additionally a water-soluble immune stimulant or antigen can be encapsulated in the core.

The nanostructure of the invention includes a liposomal core. A liposomal core as used herein refers to a centrally located core compartment formed by a component of the lipids or phospholipids that form a lipid bilayer. "Liposomes" are artificial, self closed vesicular structure of various sizes and structures, where one or several membranes encapsulate an aqueous core. Most typically liposome membranes are formed from lipid bilayers membranes, where the hydrophilic head groups are oriented towards the aqueous environment and the lipid chains are embedded in the lipophilic core. Liposomes can be formed as well from other amphiphilic monomeric and polymeric molecules, such as polymers, like block copolymers, or polypeptides. Unilamellar vesicles are liposomes defined by a single membrane enclosing an aqueous space. In contrast, oligo- or multilamellar vesicles are built up of several membranes. Typically, the membranes are roughly 4 nm thick and are composed of amphiphilic lipids, such as phospholipids, of natural or synthetic origin. Optionally, the membrane properties can be modified by the incorporation of other lipids such as sterols or cholic acid derivatives.

The lipid bilayer is composed of two layers of lipid molecules. Each lipid molecule in a layer is oriented substantially parallel to adjacent lipid bilayers, and two layers that form a bilayer have the polar ends of their molecules exposed to the aqueous phase and the non-polar ends adjacent to each other, as shown in the diagrams of FIGS. 1-3. The central aqueous region of the liposomal core may be empty or filled fully or partially with water, an aqueous emulsion, antigen, immune stimulant, immune suppressor or other therapeutic or diagnostic agent.

"Lipid" refers to its conventional sense as a generic term encompassing fats, lipids, alcohol-ether-soluble constituents of protoplasm, which are insoluble in water. Lipids usually consist of a hydrophilic and a hydrophobic moiety. In water lipids can self organize to form bilayers membranes, where the hydrophilic moieties (head groups) are oriented towards the aqueous phase, and the lipophilic moieties (acyl chains) are embedded in the bilayers core. Lipids can comprise as well two hydrophilic moieties (bola amphiphiles). In that case, membranes may be formed from a single lipid layer, and not a bilayer. Typical examples for lipids in the current context are fats, fatty oils, essential oils, waxes, steroid, sterols, phospholipids, glycolipids, sulpholipids, aminolipids, chromolipids, and fatty acids. The term encompasses both naturally occurring and synthetic lipids. Preferred lipids in connection with the present invention are: steroids and sterol, particularly cholesterol, phospholipids, including phosphatidyl, phosphatidylcholines and phosphatidylethanolamines and sphingomyelins. Where there are fatty acids, they could be about 12-24 carbon chains in length, containing up to 6 double bonds. The fatty acids are linked to the backbone, which may be derived from glycerol. The fatty acids within one lipid can be different (asymmetric), or there may be only 1 fatty acid chain present, e.g. lysolecithins. Mixed formulations are also possible, particularly when the non-cationic lipids are derived from natural sources, such as lecithins (phosphatidylcholines) purified from egg yolk, bovine heart, brain, liver or soybean.

The liposomal core can be constructed from one or more lipids known to those in the art including but not limited to: sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and their derivatives.

An immune stimulant is associated with the lipid bilayer of the liposomal core. An immune stimulant, as used herein, is a substance that causes stimulation of the immune system such that one or more immune factors, i.e., cytokines, immune cells, antibodies, chemokines are induced or activated. The immune response may comprise a cellular and/or a humoral response. The immune stimulant can be, for example, a small molecule, a nucleic acid, a protein, or a combination thereof. The immune stimulant may also be capable of activating expression of immune stimulatory molecules on cells of a localized microenvironment.

The immune stimulant incorporated into the bilayer can be a wide variety of molecules including but not limited to: monophosphoryl lipid A, lipid A from bacterial origin, 22:0 trehalose, dimethyldioctadecyl-ammonium, Kdo2 lipid A, inositol phosphates including IP3(1,3,4), IP3(1,3,5), IP3(1, 4,5), IPR(1,3,4,5), LPA/S1P receptor selective agonists, PAF and PAF analogs, liponucleotides, cyclic LPA, bioactive ceramides, endocannabinoids, anandamides, lipid oxidation products, diacylglycerol phosphate, bacterial membrane lipids, N-acylglycine lipids, acyl carnitine lipids, mycolic acids, plant lipid extracts, FSL-1, PAM3CSK4, HKLM, LPS, FLA-ST, imiquimod, resiquimod, C12-IE-DAP, L18-MDP and other compounds known to those in the art that can stimulate toll like receptors, NOD receptors, and other pro-inflammatory immune receptors that would be productive towards inducing an immune response.

The immune stimulant is associated with the liposomal core. It may be associated with by being embedded within the core or it may be attached or linked, either indirectly (i.e. non-covalently or covalently through other molecules such a linkers) or directly (i.e. covalently).

The nanostructure of the invention also includes an oligonucleotide which is preferably a therapeutic oligonucleotide. An oligonucleotide, as used herein, refers to any nucleic acid containing molecule. The nucleic acid may be DNA, RNA, PNA, LNA, ENA or combinations or modifications thereof. It may also be single, double or triple stranded. A therapeutic oligonucleotide is an oligonucleotide that can function as a therapeutic and or diagnostic agent.

The oligonucleotides are positioned on the exterior of the liposomal core. At least one oligonucleotide is on the exterior. In some embodiments at least 25, 50, 75, 100, 200, 300, 400, 500, 600, 700, 800, 900 or 1,000 oligonucleotides or any range combination thereof are on the exterior of the liposomal core. In some embodiments, 1-1000, 10-500, 50-250, or 50-300 oligonucleotides are present on the surface. In some instance the oligonucleotides form an oligonucleotide shell. An oligonucleotide shell is formed when at least 50% of the available surface area of the exterior surface of the liposomal includes an oligonucleotide. In some embodiments at least 60%, 70%, 80%, 90%, 95%, 96%, 97% 98% or 99% of the available surface area of the exterior surface of the liposomal includes an oligonucleotide. The oligonucleotides of the oligonucleotide shell may be oriented in a variety of directions. In some embodiments the oligonucleotides are oriented radially outwards.

The oligonucleotides may be linked to the core or to one another and/or to other molecules such an antigens either directly or indirectly through a linker. The oligonucleotides may be conjugated to a linker via the 5' end or the 3' end. E.g. [Sequence, 5'-3']-Linker or Linker-[Sequence, 5'-3']. Some or all of the oligonucleotides of the nanostructure may be linked to one another either directly or indirectly through a covalent or non-covalent linkage. The linkage of one oligonucleotide to another oligonucleotide may be in addition to or alternatively to the linkage of that oligonucleotide to liposomal core. One or more of the oligonucleotides may also be linked to other molecules such as an antigen. The oligonucleotides may be linked to the antigen of the core either directly or indirectly through a covalent or non-covalent linkage.

The oligonucleotide shell can be a wide variety of molecules including but not limited to: single-stranded deoxyribonucleotides, ribonucleotides, and other single-stranded oligonucleotides incorporating one or a multiplicity of modifications known to those in the art, double-stranded deoxyribonucleotides, ribonucleotides, and other double-stranded oligonucleotides incorporating one or a multiplicity of modifications known to those in the art, oligonucleotide triplexes incorporating deoxyribonucleotides, ribonucleotides, or oligonucleotides that incorporate one or a multiplicity of modifications known to those in the art. In another embodiment one or a multiplicity of different oligonucleotides are present on the same surface of a single liposomal nanostructure.

The oligonucleotide shell may be anchored to the surface of the liposomal core through conjugation to one or a multiplicity of linker molecules including but not limited to: tocopherols, sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyl-lanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and their derivatives. The oligonucleotide may be a nucleic acid that interacts with a molecule or complex of molecules that when stimulated produce an immune response in response to that interaction. The molecule or complex of molecules may be a receptor. In some embodiments the oligonucleotide may be a pattern recognition receptor (PRR) modulating oligonucleotide. PRRs are a primitive part of the immune system composed of proteins expressed by cells of the innate immune system to identify pathogen-associated molecular patterns (PAMPs), which are associated with microbial pathogens or cellular stress, as well as damage-associated molecular patterns (DAMPs), which are associated with cell components released during cell damage. PRRs include but are not limited to membrane-bound PRRs, such as receptor kinases, toll-like receptors (TLR), and C-type lectin Receptors (CLR) (mannose receptors and asialoglycoprotein receptors); Cytoplasmic PRRs such as RIG-I-like receptors (RLR), RNA Helicases, Plant PRRs, and NonRD kinases; and secreted PRRs. PRR modulating oligonucleotides include but are not limited to TLR agonists, agonists or antagonists of RIG-I, transcription factors, cellular translation machinery, cellular transcription machinery, nucleic-acid acting enzymes, and nucleic acid associating autoantigens. One example of this embodiment is the use of unmethylated 5'-cytosine-phosphate-guanosine-3' (CpG) motifs. Another is the use of 5'-UUG-3' or 5'-UUA-3' motifs. Still another is the use of long double stranded RNA.

A TLR agonist, as used herein is a nucleic acid molecule that interacts with and stimulates the activity of a TLR. Toll-like receptors (TLRs) are a family of highly conserved polypeptides that play a critical role in innate immunity in mammals. At least ten family members, designated TLR1-TLR10, have been identified. The cytoplasmic domains of the various TLRs are characterized by a Toll-interleukin 1 (IL-1) receptor (TIR) domain. Medzhitov R et al. (1998) Mol Cell 2:253-8. Recognition of microbial invasion by TLRs triggers activation of a signaling cascade that is evolutionarily conserved in *Drosophila* and mammals. The TIR domain-containing adaptor protein MyD88 has been reported to associate with TLRs and to recruit IL-1 receptor-associated kinase (IRAK) and tumor necrosis factor (TNF) receptor-associated factor 6 (TRAF6) to the TLRs. The MyD88-dependent signaling pathway is believed to lead to activation of NF-κB transcription factors and c-Jun $NH_2$ terminal kinase (Jnk) mitogen-activated protein kinases (MAPKs), critical steps in immune activation and production of inflammatory cytokines. For a review, see Aderem A et al. (2000) Nature 406:782-87.

TLRs are believed to be differentially expressed in various tissues and on various types of immune cells. For example, human TLR7 has been reported to be expressed in placenta, lung, spleen, lymph nodes, tonsil and on plasmacytoid precursor dendritic cells (pDCs). Chuang T-H et al. (2000) *Eur Cytokine Netw* 11:372-8; Kadowaki N et al. (2001) *J Exp Med* 194:863-9. Human TLR8 has been reported to be expressed in lung, peripheral blood leukocytes (PBL), placenta, spleen, lymph nodes, and on monocytes. Kadowaki N et al. (2001) *J Exp Med* 194:863-9; Chuang T-H et al. (2000) *Eur Cytokine Netw* 11:372-8. Human TLR9 is reportedly expressed in spleen, lymph nodes, bone marrow, PBL, and on pDCs, and B cells. Kadowaki N et al. (2001) *J Exp Med* 194:863-9; Bauer S et al. (2001) *Proc Natl Acad Sci USA* 98:9237-42; Chuang T-H et al. (2000) *Eur Cytokine Netw* 11:372-8.

Nucleotide and amino acid sequences of human and murine TLR7 are known. See, for example, GenBank Accession Nos. AF240467, AF245702, NM_016562, AF334942, NM_133211; and AAF60188, AAF78035, NP_057646, AAL73191, and AAL73192, the contents of all of which are incorporated herein by reference. Human TLR7 is reported to be 1049 amino acids long. Murine TLR7 is reported to be 1050 amino acids long. TLR7 polypeptides include an extracellular domain having a leucine-rich repeat region, a transmembrane domain, and an intracellular domain that includes a TIR domain.

Nucleotide and amino acid sequences of human and murine TLR8 are known. See, for example, GenBank Accession Nos. AF246971, AF245703, NM_016610, XM_045706, AY035890, NM_133212; and AAF64061, AAF78036, NP_057694, XP_045706, AAK62677, and NP_573475, the contents of all of which is incorporated herein by reference. Human TLR8 is reported to exist in at least two isoforms, one 1041 amino acids long and the other 1059 amino acids long. Murine TLR8 is 1032 amino acids long. TLR8 polypeptides include an extracellular domain having a leucine-rich repeat region, a transmembrane domain, and an intracellular domain that includes a TIR domain.

Nucleotide and amino acid sequences of human and murine TLR9 are known. See, for example, GenBank Accession Nos. NM_017442, AF259262, AB045180, AF245704, AB045181, AF348140, AF314224, NM_031178; and NP_059138, AAF72189, BAB19259, AAF78037, BAB19260, AAK29625, AAK28488, and NP_112455, the contents of all of which are incorporated herein by reference. Human TLR9 is reported to exist in at least two isoforms, one 1032 amino acids long and the other 1055 amino acids. Murine TLR9 is 1032 amino acids long. TLR9 polypeptides include an extracellular domain having a leucine-rich repeat region, a transmembrane domain, and an intracellular domain that includes a TIR domain.

As used herein, the term "TLR signaling" refers to any aspect of intracellular signaling associated with signaling through a TLR. As used herein, the term "TLR-mediated immune response" refers to the immune response that is associated with TLR signaling. The level of TLR signaling may be enhanced over a pre-existing level of signaling or it may be induced over a background level of signaling.

A TLR3-mediated immune response is a response associated with TLR3 signaling. TLR3 agonists include but are not limited to dsRNA such as dsRNA having multiple AU motifs.

A TLR7-mediated immune response is a response associated with TLR7 signaling. TLR7-mediated immune response is generally characterized by the induction of IFN-α and IFN-inducible cytokines such as IP-10 and I-TAC. The levels of cytokines IL-1 α/β, IL-6, IL-8, MIP-1α/β and MIP-3a/(3 induced in a TLR7-mediated immune response are less than those induced in a TLR8-mediated immune response. TLR7 ligands include, without limitation, guanosine analogues such as C8-substituted guanosines, mixtures of ribonucleosides consisting essentially of G and U, guanosine ribonucleotides and RNA or RNA-like molecules (PCT/US03/10406), and adenosine-based compounds (e.g., 6-amino-9-benzyl-2-(3-hydroxy-propoxy)-9H-purin-8-ol, and similar compounds made by Sumitomo (e.g., CL-029)).

As used herein, the term "guanosine analogues" refers to a guanosine-like nucleotide (excluding guanosine) having a chemical modification involving the guanine base, guanosine nucleoside sugar, or both the guanine base and the guanosine nucleoside sugar. Guanosine analogues specifically include, without limitation, 7-deaza-guanosine.

Guanosine analogues further include C8-substituted guanosines such as 7-thia-8-oxoguanosine (immunosine), 8-mercaptoguanosine, 8-bromoguanosine, 8-methylguanosine, 8-oxo-7,8-dihydroguanosine, C8-arylamino-2'-deoxyguanosine, C8-propynyl-guanosine, C8- and N7-substituted guanine ribonucleosides such as 7-allyl-8-oxoguanosine (loxoribine) and 7-methyl-8-oxoguanosine, 8-aminoguanosine, 8-hydroxy-2'-deoxyguanosine, 8-hydroxyguanosine, and 7-deaza 8-substituted guanosine.

A TLR8-mediated immune response is a response associated with TLR8 signaling. This response is further characterized by the induction of pro-inflammatory cytokines such as IFN-γ, IL-12p40/70, TNF-α, IL-1α/β, IL-6, IL-8, MIP-1 α/β and MIP-3 α/β. TLR8 ligands include mixtures of ribonucleosides consisting essentially of G and U, guanosine ribonucleotides and RNA or RNA-like molecules (PCT/US03/10406). Additional TLR8 ligands are also disclosed in Gorden et al. J. Immunol. 2005, 174:1259-1268).

As used herein, a "TLR7/8 agonist" collectively refers to any nucleic acid that is capable of increasing TLR7 and/or TLR8 signaling (i.e., an agonist of TLR7 and/or TLR8). Some TLR7/8 ligands induce TLR7 signaling alone (e.g., TLR7 specific agonists), some induce TLR8 signaling alone (e.g., TLR8 specific agonists), and others induce both TLR7 and TLR8 signaling.

A TLR9-mediated immune response is a response associated with TLR9 signaling. This response is further characterized at least by the production/secretion of IFN-γ and IL-12, albeit at levels lower than are achieved via a TLR8-mediated immune response. As used herein, the term "TLR9 agonist" refers to any agent that is capable of increasing TLR9 signaling (i.e., an agonist of TLR9). TLR9 agonists specifically include, without limitation, immunostimulatory nucleic acids, and in particular CpG immunostimulatory nucleic acids.

"Immunostimulatory CpG nucleic acids" or "immunostimulatory CpG oligonucleotides" refers to any CpG-containing nucleic acid that is capable of activating an immune cell. At least the C of the CpG dinucleotide is typically, but not necessarily, unmethylated. Immunostimulatory CpG nucleic acids are described in a number of issued patents and published patent applications, including U.S. Pat. Nos. 6,194,388; 6,207,646; 6,218,371; 6,239,116; 6,339,068; 6,406,705; and 6,429,199.

A TLR13-mediated immune response is a response associated with TLR13 signaling. A TLR13 agonist is bacterial 23S rRNA.

The oligonucleotides may also be retinoic acid inducible gene-I (RIG-I) agonists or antagonists. RIG-I corresponds to GenBank Accession No. AF038963. RIG-I agonists include but are not limited to dsRNA such as Poly(I:C). RIG-I antagonists include short 5'triphosphate DNA or RNA.

An "immunostimulatory oligonucleotide" is any nucleic acid (DNA or RNA) containing an immunostimulatory motif or backbone that is capable of inducing an immune response. An induction of an immune response refers to any increase in number or activity of an immune cell, or an increase in expression or absolute levels of an immune factor, such as a cytokine. Immune cells include, but are not limited to, NK cells, CD4+T lymphocytes, CD8+T lymphocytes, B cells, dendritic cells, macrophage and other antigen-presenting cells. Cytokines include, but are not limited to, interleukins, TNF-α, IFN-α,β and γ, Flt-ligand, and co-stimulatory molecules. Immunostimulatory motifs include, but are not limited to CpG motifs and T-rich motifs.

A non-limiting set of immunostimulatory oligonucleotides includes:

```
dsRNA:
poly(A:C) and poly(I:C)
ssRNA:
                                       (SEQ ID NO: 4)
CCGUCUGUUGUGUGACUC (SEQ ID NO: 6)
GCCACCGAGCCGAAGGCACC (SEQ ID NO: 7)
UAUAUAUAUAUAUAUAUAUA (SEQ ID NO: 8)
UUAUUAUUAUUAUUAUUAUU (SEQ ID NO: 9)
UUUUAUUUUAUUUUAUUUUA (SEQ ID NO: 10)
UGUGUGUGUGUGUGUGUGUG (SEQ ID NO: 11)
UUGUUGUUGUUGUUGUUGUU (SEQ ID NO: 12)
UUUGUUUGUUUGUUUGUUUG (SEQ ID NO: 13)
UUAUUUAUUUAUUUAUUUAU (SEQ ID NO: 14)
UUGUUUGUUUGUUUGUUUGU (SEQ ID NO: 15)
GCCCGUCUGUUGUGUGACUC (SEQ ID NO: 16)
GUCCUUCAAGUCCUUCAA

DNA:
                                       (SEQ ID NO: 5)
GGTGCATCGATGCAGGGGGG (SEQ ID NO: 17)
TCCATGGACGTTCCTGAGCGTT (SEQ ID NO: 18)
TCGTCGTTCGAACGACGTTGAT (SEQ ID NO: 19)
TCGTCGACGATCCGCGCGCGCG
```

-continued

GGGGTCAACGTTGAGGGGGG (SEQ ID NO: 20)

TCGTCGTTTTGTCGTTTTGTCGTT (SEQ ID NO: 21)

TCGTCGTTGTCGTTTTGTCGTT (SEQ ID NO: 22)

GGGGGACGATCGTCGGGGGG (SEQ ID NO: 23)

GGGGACGACGTCGTGGGGGG (SEQ ID NO: 24)

TCGTCGTTTTCGGCGCGCGCCG (SEQ ID NO: 25)

TCGTCGTCGTTCGAACGACGTTGAT (SEQ ID NO: 26)

The terms "oligonucleotide" and "nucleic acid" are used interchangeably to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymidine (T) or uracil (U)) or a substituted purine (e.g., adenine (A) or guanine (G)). Thus, the term embraces both DNA and RNA oligonucleotides. The terms shall also include oligonucleosides (i.e., a oligonucleotide minus the phosphate) and any other organic base containing polymer. Oligonucleotides can be obtained from existing nucleic acid sources (e.g., genomic or cDNA), but are preferably synthetic (e.g., produced by nucleic acid synthesis). The oligonucleotides may be single stranded or double stranded. A double stranded oligonucleotide is also referred to herein as a duplex. Double-stranded oligonucleotides of the invention can comprise two separate complementary nucleic acid strands.

As used herein, "duplex" includes a double-stranded nucleic acid molecule(s) in which complementary sequences or partially complementary sequences are hydrogen bonded to each other. The complementary sequences can include a sense strand and an antisense strand. The antisense nucleotide sequence can be identical or sufficiently identical to the target gene to mediate effective target gene inhibition (e.g., at least about 98% identical, 96% identical, 94%, 90% identical, 85% identical, or 80% identical) to the target gene sequence.

A double-stranded oligonucleotide can be double-stranded over its entire length, meaning it has no overhanging single-stranded sequences and is thus blunt-ended. In other embodiments, the two strands of the double-stranded oligonucleotide can have different lengths producing one or more single-stranded overhangs. A double-stranded oligonucleotide of the invention can contain mismatches and/or loops or bulges. In some embodiments, it is double-stranded over at least about 70%, 80%, 90%, 95%, 96%, 97%, 98% or 99% of the length of the oligonucleotide. In some embodiments, the double-stranded oligonucleotide of the invention contains at least or up to 1, 2, 3, 4, 5, 6, 7, 8, 9, 10, 11, 12, 13, 14, or 15 mismatches.

Oligonucleotides associated with the invention can be modified such as at the sugar moiety, the phosphodiester linkage, and/or the base. As used herein, "sugar moieties" includes natural, unmodified sugars, including pentose, ribose and deoxyribose, modified sugars and sugar analogs. Modifications of sugar moieties can include replacement of a hydroxyl group with a halogen, a heteroatom, or an aliphatic group, and can include functionalization of the hydroxyl group as, for example, an ether, amine or thiol.

Modification of sugar moieties can include 2'-O-methyl nucleotides, which are referred to as "methylated." In some instances, oligonucleotides associated with the invention may only contain modified or unmodified sugar moieties, while in other instances, oligonucleotides contain some sugar moieties that are modified and some that are not.

In some instances, modified nucleomonomers include sugar- or backbone-modified ribonucleotides. Modified ribonucleotides can contain a non-naturally occurring base such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides can have the 2'-OH group replaced by an H, alkoxy (or OR), R or alkyl, halogen, SH, SR, amino (such as $NH_2$, NHR, $NR_2$,), or CN group, wherein R is lower alkyl, alkenyl, or alkynyl. In some embodiments, modified ribonucleotides can have the phosphodiester group connecting to adjacent ribonucleotides replaced by a modified group, such as a phosphorothioate group.

In some aspects, 2'-O-methyl modifications can be beneficial for reducing undesirable cellular stress responses, such as the interferon response to double-stranded nucleic acids. Modified sugars can include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy ($—OCH_2CH=CH_2$), 2'-propargyl, 2'-propyl, ethynyl, ethenyl, propenyl, and cyano and the like. The sugar moiety can also be a hexose.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In some embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. The term "alkenyl" includes unsaturated aliphatic groups analogous in length and possible substitution to the alkyls described above, but that contain at least one double bond. Unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-$N^6$-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In some aspects, the nucleomonomers of a oligonucleotide of the invention are RNA nucleotides, including modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

As used herein, the term "linkage" used in the context of an internucleotide linkage includes a naturally occurring, unmodified phosphodiester moiety (—O—($PO^{2-}$)—O—) that covalently couples adjacent nucleomonomers. As used herein, the term "substitute linkage" or "modified linkage" or modified internucleotide linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothioate linkages.

In some aspects, oligonucleotides of the invention comprise 3' and 5' termini (except for circular oligonucleotides). The 3' and 5' termini of a oligonucleotide can be substantially protected from nucleases, for example, by modifying the 3' or 5' linkages (e.g., U.S. Pat. No. 5,849,902 and WO 98/13526). Oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. Antisense Res. Dev. 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-0 that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3'linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

In some aspects, oligonucleotides can be chimeric RNA-DNA oligonucleotides which include both DNA and RNA.

The oligonucleotides are preferably in the range of 6 to 100 bases in length. However, nucleic acids of any size greater than 4 nucleotides (even many kb long) are capable of inducing a biological response according to the invention if sufficient stimulatory motifs are present. Preferably the nucleic acid is in the range of between 8 and 100 and in some embodiments between 8 and 50 or 8 and 30 nucleotides in size.

In some embodiments the oligonucleotides have a modified backbone such as a phosphorothioate (PS) backbone. In other embodiments the oligonucleotides have a phosphodiester (PO) backbone. In yet other embodiments oligonucleotides have a mixed or chimeric PO and PS backbone.

The nanostructure may also include an antigen. An antigen as used herein is a molecule capable of provoking an immune response in the body, especially the production of antibodies. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and multicellular organisms such as parasites and allergens. The term antigen broadly includes any type of molecule which is recognized by a host immune system as being foreign. Antigens include but are not limited to cancer antigens, microbial antigens, and allergens.

Figure 10:
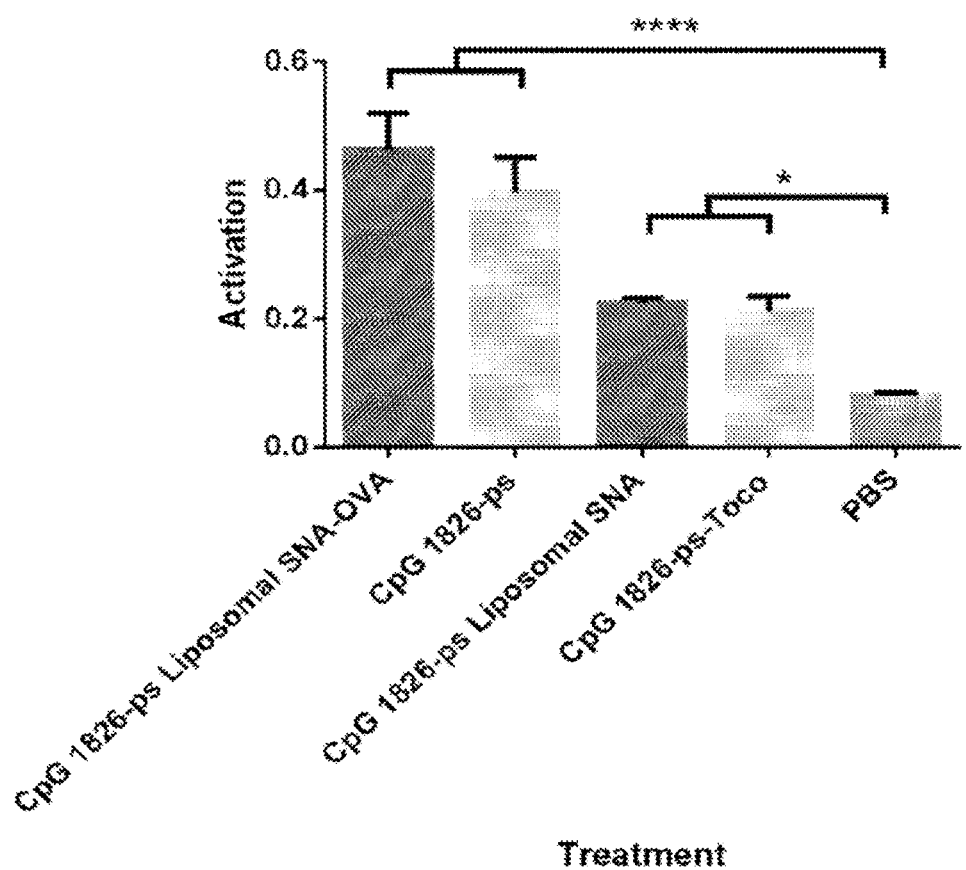
FIG. 10 is a graph showing antigen-conjugated liposomal nanostructures demonstrates activation of immune cells.
Figure 11:
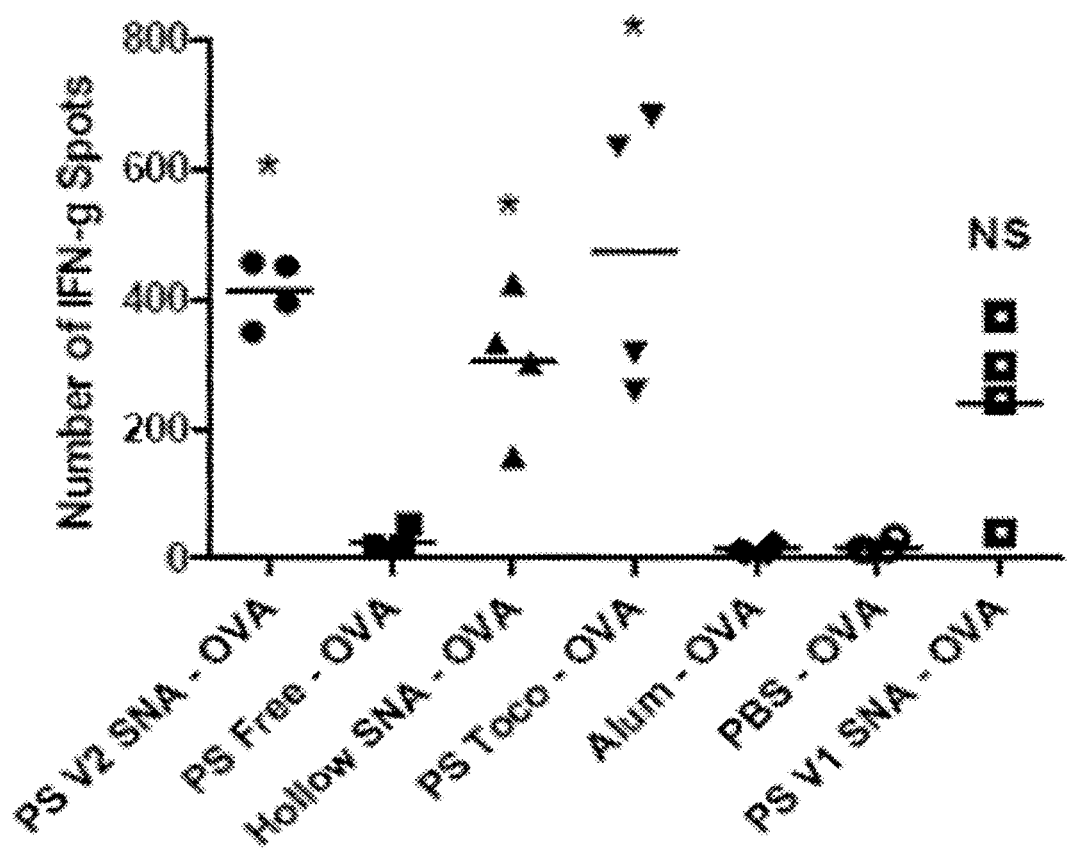
FIG. 11 is a graph showing that nanostructures induce cellular responses more effectively than free PS oligo and alum. C57BL/6 mice (N=4/group) were immunized with the indicated formulations on day 0 and 21 using ovalbumin as the model antigen. On day 28, splenocytes were collected and incubated overnight on IFN-γ ELISPOT plates with 1 uM OVA(257-264). The number of IFN-γ spots was quantified using an automated ELISPOT counter. *$p<0.05$, NS=non-significant

Antigen can be attached to the structures by the externally-facing oligonucleotide through covalent or non-covalent, e.g. Watson/Crick hybridization. Alternatively or additionally the antigen may be incorporated into the liposomal bilayer via conjugation to a hydrophobic moiety (FIGS. 2-3). The data presented herein demonstrates that this form of antigen delivery provokes unexpectedly more potent induction of immune stimulatory effects in vitro (FIG. 10) and induces effective antigen processing and presentation, leading to effective induction of an anti-tumor immune response in vivo at highly unexpected levels (FIG. 11-12). In yet another embodiment, antigen may be incorporated inside the inner aqueous layer of the liposome (FIG. 3).

In one embodiment, antigen is conjugated to the liposomal nanostructure via interactions with the oligonucleotide shell (FIG. 2). In some instances the antigen-oligonucleotide conjugate is linked to the liposomal core through oligonucleotide hybridization. In other words the oligonucleotide is hybridized to a complementary or partially complementary oligonucleotide to form a duplex or partial duplex. One or both of the oligonucleotides of the duplex is linked directly to the liposomal core and the antigen which is external facing (on the outside of the lipid bilayer) or which is internal (in the inner aqueous layer) and not directly linked to the liposomal core is linked to one or both of the oligonucleotides in the duplex. In another embodiment, antigen is conjugated to the liposomal nanostructure via direct interactions with the liposomal core (FIG. 3). The antigen can be anchored to the surface of the liposomal core through conjugation to one or a multiplicity of linker molecules including but not limited to: tocopherols, sphingolipids such as sphingosine, sphingosine phosphate, methylated sphingosines and sphinganines, ceramides, ceramide phosphates, 1-0 acyl ceramides, dihydroceramides, 2-hydroxy ceramides, sphingomyelin, glycosylated sphingolipids, sulfatides, gangliosides, phosphosphingolipids, and phytosphingosines of various lengths and saturation states and their derivatives, phospholipids such as phosphatidylcholines, lysophosphatidylcholines, phosphatidic acids, lysophosphatidic acids, cyclic LPA, phosphatidylethanolamines, lysophosphatidylethanolamines, phosphatidylglycerols, lysophosphatidylglycerols, phosphatidylserines, lysophosphatidylserines, phosphatidylinositols, inositol phosphates, LPI, cardiolipins, lysocardiolipins, bis(monoacylglycero) phosphates, (diacylglycero) phosphates, ether lipids, diphytanyl ether lipids, and plasmalogens of various lengths, saturation states, and their derivatives, sterols such as cholesterol, desmosterol, stigmasterol, lanosterol, lathosterol, diosgenin, sitosterol, zymosterol, zymostenol, 14-demethyllanosterol, cholesterol sulfate, DHEA, DHEA sulfate, 14-demethyl-14-dehydrlanosterol, sitostanol, campesterol, ether anionic lipids, ether cationic lipids, lanthanide chelating lipids, A-ring substituted oxysterols, B-ring substituted oxysterols, D-ring substituted oxysterols, side-chain substituted oxysterols, double substituted oxysterols, cholestanoic acid derivatives, fluorinated sterols, fluorescent sterols, sulfonated sterols, phosphorylated sterols, and polyunsaturated sterols of different lengths, saturation states, and their derivatives.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, Cancer Research, 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of viruses that have been found in humans include but are not limited to: Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and other viruses (e.g. the agent of delta hepatitis (thought to be a defective satellite of hepatitis B virus), Hepatitis C; Norwalk and related viruses, and astroviruses).

Both gram negative and gram positive bacteria serve as antigens in vertebrate animals. Such gram positive bacteria include, but are not limited to, *Pasteurella* species, Staphylococci species, and *Streptococcus* species. Gram negative bacteria include, but are not limited to, *Escherichia coli*, *Pseudomonas species*, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Rickettsia*, and *Actinomyces israelli*.

Examples of fungi include *Cryptococcus neoformans, Histoplasma capsulatum, Coccidioides immitis, Blastomyces dermatitidis, Chlamydia trachomatis, Candida albicans*.

Other infectious organisms (i.e., protists) include *Plasmodium* spp. such as *Plasmodium falciparum, Plasmodium malariae, Plasmodium ovale*, and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma* rhodesiense (African sleeping sickness), *Trypanosoma cruzi* (Chagas' disease), and *Toxoplasma gondii*.

Other medically relevant microorganisms have been described extensively in the literature, e.g., see C. G. A Thomas, *Medical Microbiology*, Bailliere Tindall, Great Britain 1983, the entire contents of which is hereby incorporated by reference.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

The nanostructures of the invention may be delivered to a subject in vivo or ex vivo for therapeutic and/or diagnostic use or may be used in vitro, ex vivo or in vivo for research purposes. Alternatively the nanostructures may be used for the purpose of provoking an immune response for generating reagents such as antibodies or cytokines which can be harvested.

The nanostructures may be administered alone or in any appropriate pharmaceutical carrier, such as a liquid, for example saline, or a powder, for administration in vivo. They can also be co-delivered with larger carrier particles or within administration devices. The nanostructures may be formulated or unformulated. The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients. In some embodiments, nanostructures are mixed with a substance such as a lotion (for example, aquaphor) and are administered to the skin of a subject, whereby the nanostructures are delivered through the skin of the subject. It should be appreciated that any method of delivery of nanoparticles known in the art may be compatible with aspects of the invention. The nanostructures may also be sterile.

For use in therapy, an effective amount of the nanostructures can be administered to a subject by any mode that delivers the nanostructures to the desired cell. Administering pharmaceutical compositions may be accomplished by any means known to the skilled artisan. Routes of administration include but are not limited to oral, parenteral, intramuscular, intravenous, subcutaneous, mucosal, intranasal, sublingual, intratracheal, inhalation, ocular, vaginal, dermal, rectal, and by direct injection.

Thus, the invention in one aspect involves the finding that the nanostructures of the invention are highly effective in mediating immune stimulatory effects. These nanostructures (stimulatory and regulatory) are useful therapeutically and prophylactically for modulating the immune system to treat cancer, infectious diseases, allergy, asthma, autoimmune disease, and other disorders and to help protect against opportunistic infections following cancer chemotherapy.

Thus the nanostructures of the invention are useful as a vaccine for the treatment of a subject at risk of developing or a subject having allergy or asthma, an infection with an infectious organism or a cancer in which a specific cancer antigen has been identified. The nanostructures can also be formulated without an antigen or allergen for protection against infection, allergy or cancer, and in this case repeated doses may allow longer term protection. A subject at risk as used herein is a subject who has any risk of exposure to an infection causing pathogen or a cancer or an allergen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or directly to the organism or even any subject living in an area where an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject may be exposed to the antigen, i.e., during pollen season, then that subject is at risk of exposure to the antigen.

A subject having an infection is a subject that has been exposed to an infectious pathogen and has acute or chronic detectable levels of the pathogen in the body. The nanostructures can be used with or without an antigen to mount an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

A subject shall mean a human or vertebrate animal including but not limited to a dog, cat, horse, cow, pig, sheep, goat, turkey, chicken, primate, e.g., monkey, and fish (aquaculture species), e.g. salmon. Thus, the invention can also be used to treat cancer and tumors, infections, autoimmune disease and allergy/asthma in non-human subjects.

As used herein, the term treat, treated, or treating when used with respect to an disorder such as an infectious disease, autoimmune disease, cancer, allergy, or asthma refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

The nanostructures of the invention may also be coated with or administered in conjunction with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites.

The nanostructures of the invention may also be used for regulating the immune response such that the level of some immune factors are decreased. Achieving specific immune downregulation or "tolerance" is a significant challenge, as the prior art, in general, acts by broadly downregulating immune responses. This non-specific approach can lead to a high incidence of side effects, toxicity, and an increased risk of acquiring infectious diseases, among others. No commercially available compounds or structures have demonstrated the ability to induce potent and specific anti-inflammatory effects in the clinic. A challenge is delivery of the appropriate signals to immune cells, such as antigen, in the absence of additional co-stimulatory signals.

The nanostructures of the invention solve some of these problems encountered by the prior art. In some embodiments an antigen can be delivered intracellularly efficiently via conjugation to a nanostructure of the invention in a manner that achieves or promotes tolerance. The methods may involve antagonizing toll-like receptors during the antigen delivery process in order to enhance the ability to induce antigen-specific tolerance. The nanostructures used for these embodiments of the invention include a liposomal core which is attached to an immune suppressor, such as a TLR 4 immune suppressor and oligonucleotides positioned on the exterior of the core.

These regulatory nanostructures are useful for downregulating an immune response or anytime it is desirable to induce tolerance. For instance, they are useful for treating and preventing autoimmune disease, allergy, asthma, or other conditions where a component of the pathology involves an overactive immune response, such as liver fibrosis or idiopathic pulmonary fibrosis.

A subject having an allergy is a subject that has or is at risk of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, urticaria (hives) and food allergies, and other atopic conditions.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: Canine (*Canis familiaris*); *Dermatophagoides* (e.g. *Dermatophagoides farinae*); *Felis* (*Felis domesticus*); *Ambrosia* (*Ambrosia artemiisfolia; Lolium* (e.g. *Lolium perenne* or *Lolium multiflorum*); *Cryptomeria* (*Cryptomeria japonica*); *Alternaria* (*Alternaria alternata*); *Alder; Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

Autoimmune disease is a class of diseases in which an subject's own antibodies react with host tissue or in which immune effector T cells are autoreactive to endogenous self peptides and cause destruction of tissue. Thus an immune response is mounted against a subject's own antigens, referred to as self antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

A "self-antigen" as used herein refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to the destruction of the tumor or cancer. Thus, in some aspects of the invention aimed at treating autoimmune disorders it is not recommended that the nanostructure be formulated with self antigens, particularly those that are the targets of the autoimmune disorder.

In other instances, the nanostructures may include small amounts of self-antigens. A number of animal studies have demonstrated that mucosal administration of low doses of antigen can result in a state of immune hyporesponsiveness or "tolerance." The active mechanism appears to be a cytokine-mediated immune deviation away from a Th1 towards a predominantly Th2 and Th3 (i.e., TGF-β dominated) response. The active suppression with low dose antigen delivery can also suppress an unrelated immune response (bystander suppression) which is of considerable interest in the therapy of autoimmune diseases, for example, rheumatoid arthritis and SLE. Bystander suppression involves the secretion of Th1-counter-regulatory, suppressor cytokines in the local environment where proinflammatory and Th1 cytokines are released in either an antigen-specific or antigen-nonspecific manner. "Tolerance" as used herein is used to refer to this phenomenon. Indeed, oral tolerance has been effective in the treatment of a number of autoimmune diseases in animals including: experimental autoimmune encephalomyelitis (EAE), experimental autoimmune myasthenia gravis, collagen-induced arthritis (CIA), and insulin-dependent diabetes mellitus. In these models, the prevention and suppression of autoimmune disease is associated with a shift in antigen-specific humoral and cellular responses from a Th1 to Th2/Th3 response.

In another aspect, the present invention is directed to a kit including one or more of the compositions previously discussed. A "kit," as used herein, typically defines a package or an assembly including one or more of the compositions of the invention, and/or other compositions associated with the invention, for example, as previously described. Each of the compositions of the kit, if present, may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions that may be associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

In some embodiments, a kit associated with the invention includes one or more components of the nanostructure. For instance the kit may include liposomes for forming a liposome core, an immune stimulant or TLR4 immune suppressor and or oligonucleotides for the exterior of the nanostructure. A kit can also include one or more antigens and or other therapeutic agents.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the use of the compositions, for example, for a particular use, e.g., to a sample. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example 1

In one embodiment reduced to practice, oligonucleotides of sequence 5'-TCCATGACGTTCCTGACGTT-3' (SEQ ID NO:1; designated as "CpG 1826") were 3'-modified with alpha-tocopherol and incorporated into small unilamellar vesicles composed of (92% w/w) 1,2-dioleoyl-sn-glycero-3-phosphatidylcholine (DOPC) mixed with (8% w/w) monophosphoryl lipid A (FIG. 1). In a sub-embodiment, these structures were further conjugated with ovalbumin, a model protein antigen via Watson-Crick type hybridization of an ovalbumin-oligo construct, where the oligo portion was complementary to CpG 1826 (5'-AACGTCAGGAACGTCATGGA-3' SEQ ID NO:2) (FIG. 2). The oligonucleotide here was selected on the basis of its ability to stimulate TLR9, whereas MPLA was selected for its ability to stimulate TLR4.

Liposomal SNA (Nanostructure) Synthesis 25 mg of 1,2-dioleoyl-sn-glycero-3-phosphatidylcholine (DOPC) dissolved in 4 mL dichloromethane (DCM) was mixed with 1 mg monophosphoryl lipid A (MPLA) dissolved in 1 mL of chloroform in a glass container. The lipids were then dried onto the walls of the glass container in a thin film by gently drying under argon until all solvent has evaporated. Any residual solvent was removed by overnight lyophilization. The next day, the lipids were reconstituted in 10 mL of liposome buffer (150 mM NaCl, 20 mM HEPES) by vortex and sonication, then passed through 2-5 freeze thaw cycles prior to serial extrusion through 100 nm, 50 nm, then 30 nm extrusion membranes. Following extrusion, 1 umol of oligonucleotide (5'-TCCATGACGTTCCTGACGTT-3' SEQ ID NO:1) with a 3'-alpha-tocopherol group covalently attached) was mixed with the 26 mg of lipid and incubated overnight at 4 C to form the liposomal SNAs. The following day, the liposomal SNAs were purified by tangential flow filtration using a 300 kDa membrane cutoff filter using >5 volume exchanges of 1×PBS.

Some liposomal SNAs were additionally modified to contain ovalbumin by conjugating the ovalbumin first to an oligonucleotide complementary to CpG 1826 (5'-AACGTCAGGAACGTCATGGA-3' SEQ ID NO:2). This ovalbumin-oligonucleotide conjugate was then hybridized to the liposomal SNAs by incubating at a 2-fold excess of ovalbumin-oligonucleotide conjugate relative to oligonucleotide on the liposomal SNA for 3 hours at 37 C, followed by overnight incubation at 4 C. Excess ovalbumin-oligonucleotide conjugate was removed by tangential flow filtration.

In Vitro Testing

Figure 4:
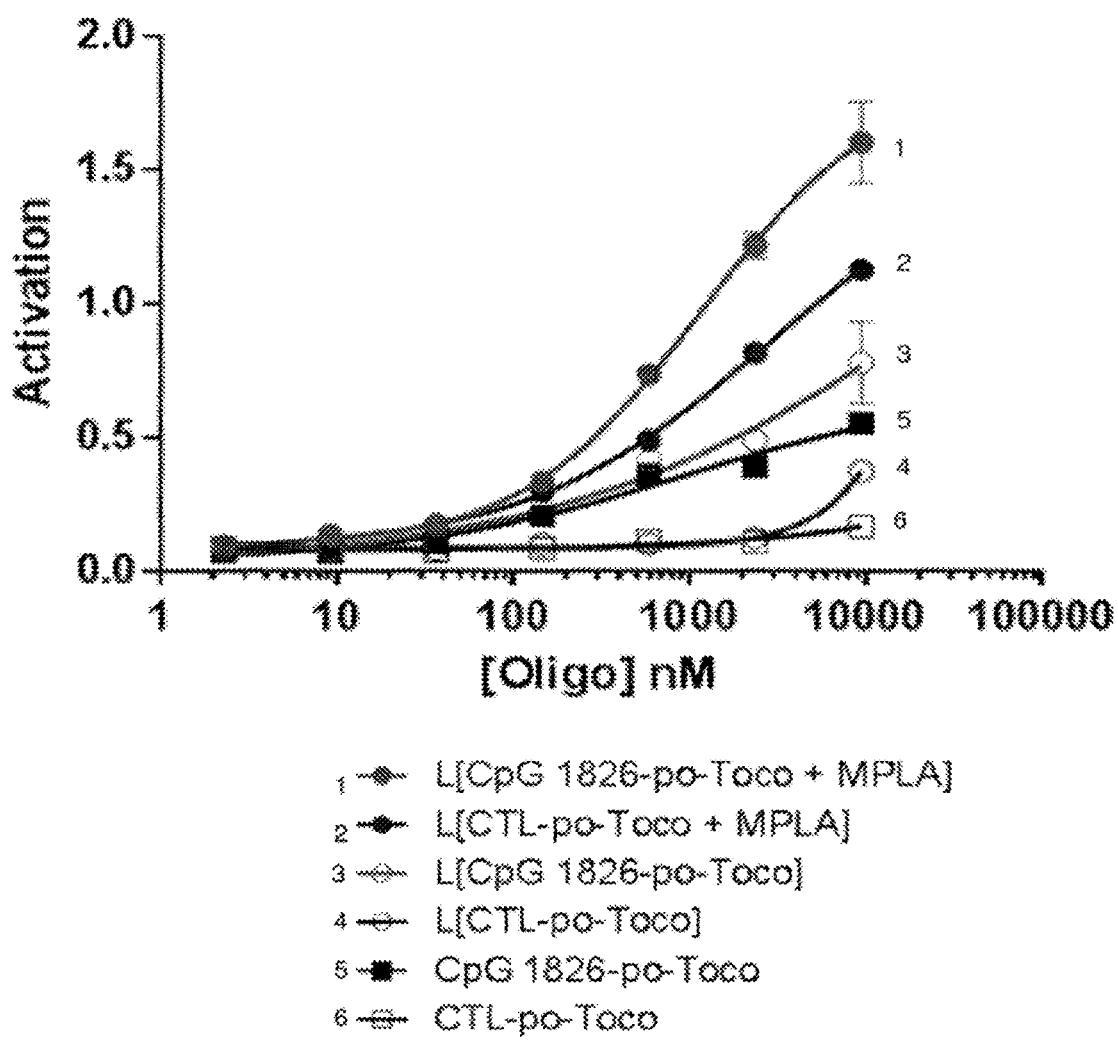
FIG. 4 is a graph showing that stimulating both TLR4 and TLR9 via liposomal nanostructures induce greater activation than either in isolation. Liposomal nanostructures which carry agonists of both TLR4 and TLR9 induce greater activation of the RAW Blue cells than either alone in isolation.
Figure 5A:
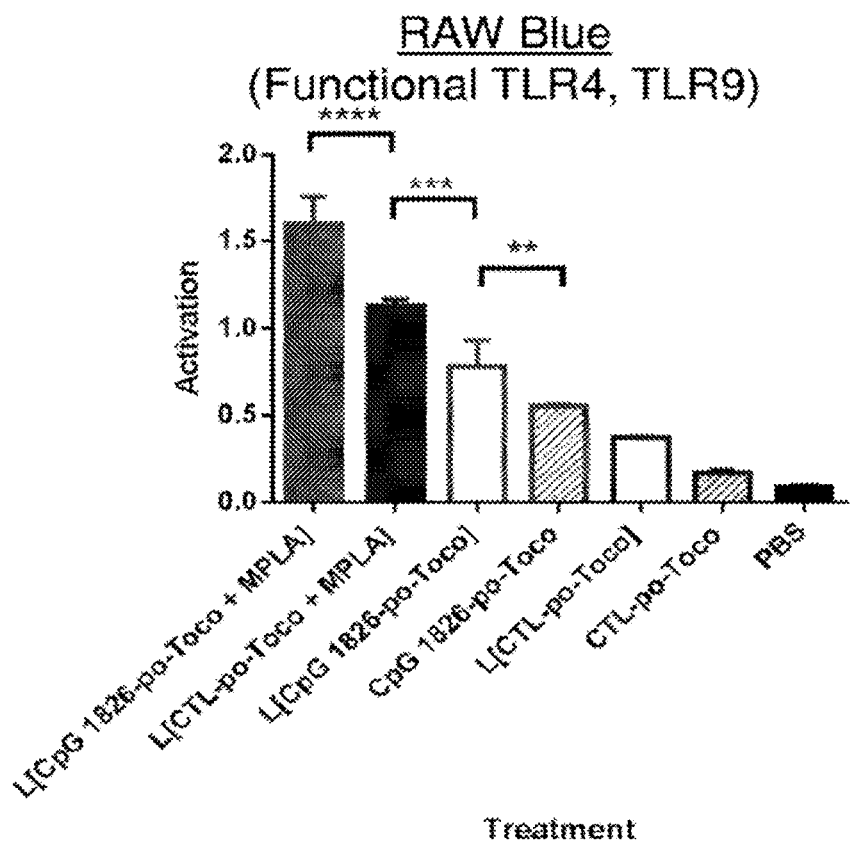
FIGS. 5A-5B are a set of bar graphs showing that activation of NF-kB by MPLA is dependent on functional TLR4. Activation of NF-kB by liposomal SNAs containing MPLA depended on functional TLR4, as the RAW Blue cell line (FIG. 5A) but not the Ramos Blue cell line (FIG. 5B) demonstrated NF-kB activation in response to stimulation. One-way ANOVA **$p<0.0001$, *$p<0.001$, **$p<0.01$.
Figure 5B:
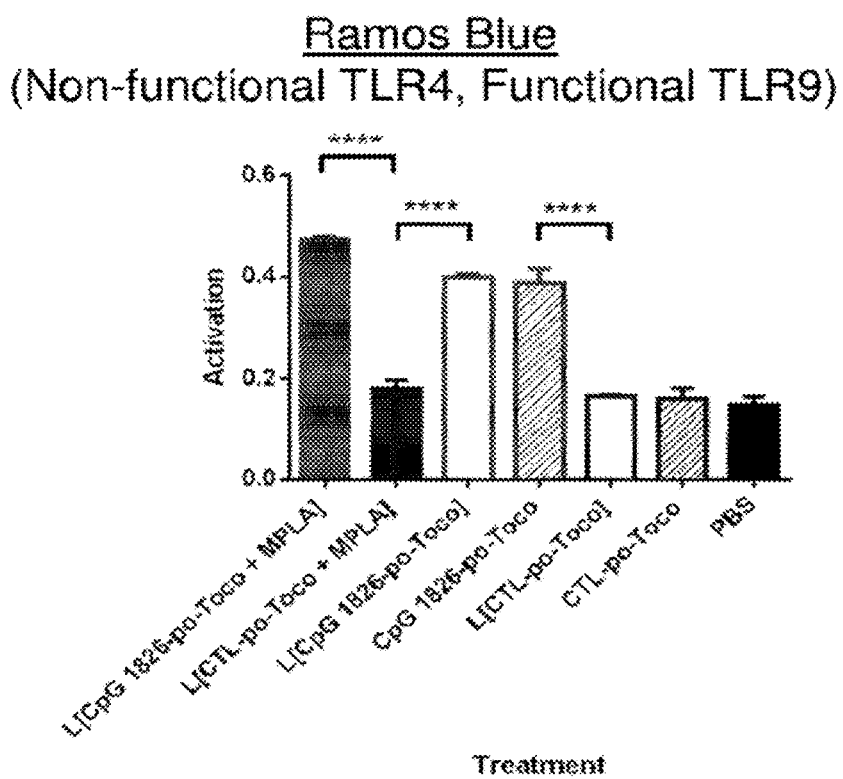

The compounds were serially diluted 1:4. 20 uL of this mixture was seeded in duplicate in a 96 well plate. RAW Blue cells (InVivoGen), a reporter murine macrophage cell line derived from RAW 264.7 cells containing a NF-kB inducible secreted alkaline phosphatase (SEAP) were seeded at 100k cells/well in 180 uL per well and added to the test compounds on the 96 well plate. Ramos Blue cells (InvivoGen), a reporter human B cell line derived from Ramos cells containing a NF-kB inducible SEAP were seeded at 306k cells/well in 180 uL per well and added to the test compounds on the 96 well plate. Importantly, Ramos Blue cells do not have functional signaling through TLR4. The cells were incubated with the test compound overnight at 37 C, 5% CO2 in a humidified chamber. The following day, the supernatants were probed for SEAP activity using the QuantiBlue reagent (InVivoGen) following the manufacturer recommended protocol. The results show that liposomal SNAs which carry agonists of both TLR4 and TLR9 induce greater activation of the RAW Blue cells that either alone in isolation (FIG. 4). Importantly, the results show that activation of NF-kB by liposomal SNAs containing MPLA depended on functional TLR4, as the RAW Blue cell line but not the Ramos Blue cell line demonstrated NF-kB activation in response to stimulation (FIG. 5).

To further profile the response triggered by liposomal SNAs containing both TLR9 and TLR4 agonists, the ability of liposomal SNAs to induce activation of MyD88-dependent and MyD88-independent pathways was tested, as measured by activation levels of TNF and IFN-alpha, respectively. For this, 6 million human peripheral blood mononuclear cells (PBMCs) were resuspended at 1 million/mL in RPMI-1640 supplemented with 10% FBS and 1% penicillin/streptomycin and seeded at 180k/well with 20 uL of test compound. Following overnight incubation, the supernatant was probed for TNF and IFN-alpha levels by ELISA. The results show that liposomal SNAs that deliver both CpG 1826 and MPLA in a single construct demonstrate elevated TNF and IFN-alpha levels that cannot be replicated either by delivering each in isolation, or by delivering both components in the same well but not on the same construct (FIG. 6). Even when a sequence that did not activate TLR9 (designated as "CTL-ps": 5'-TCCATGAGCTTCCT-GAGCTT-3' SEQ ID N0:3) was used to construct the liposomal SNA, enhanced activity of MPLA was observed (FIG. 7), suggesting that the liposomal SNA delivers MPLA more efficiently than a liposomal formulation.

Figure 8:
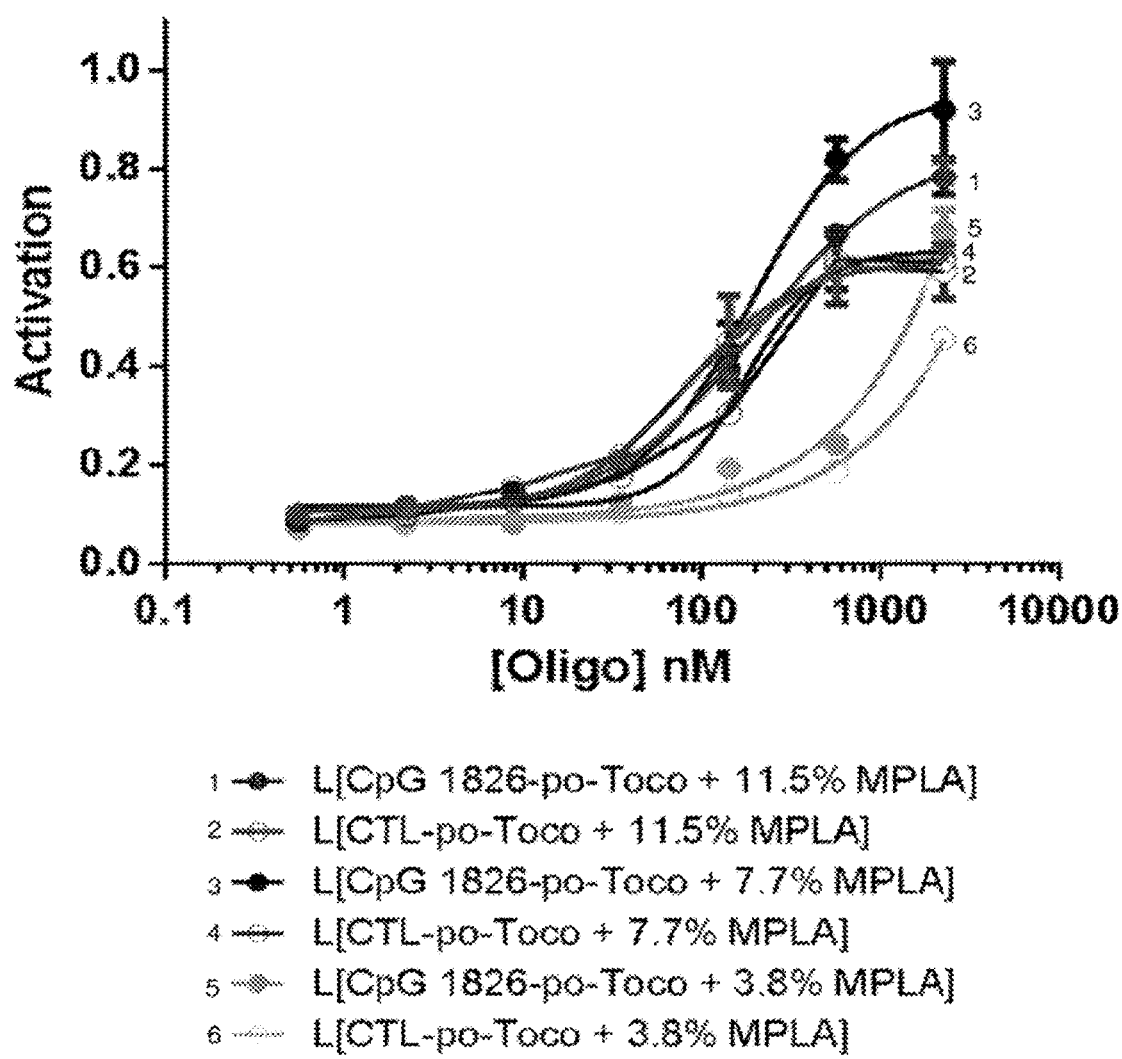
FIG. 8 is a graph showing that increasing MPLA feed into nanostructures formulation above 3.8% but not beyond 7.7% improves activity. In the RAW Blue cell line, it was observed that increasing the MPLA feed up to 7.7% MPLA but not up to 11.5% increased the potency of activation of the liposomal SNA.
Figure 9:
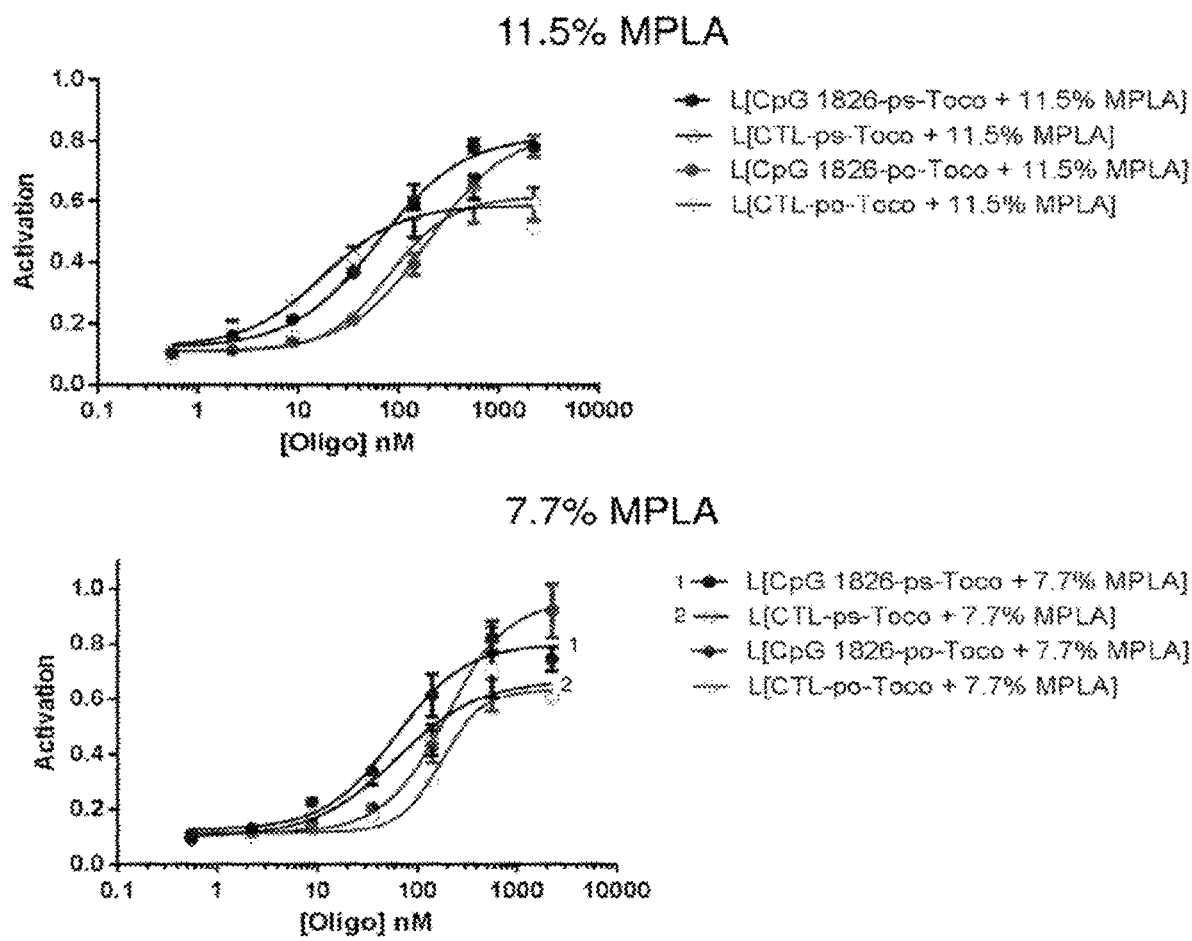
FIG. 9 is a set of graphs showing that phosphorothioate (PS) linkages increase potency but not maximal stimulation in murine immune cells at 11.5% MPLA (top panel) or 7.7% MPLA (bottom panel). In the RAW Blue cells, a shift was observed in the potency of the liposomal nanostructures but not in the maximal stimulation, though this is anticipated to be species dependent.

Next, parameters that might modulate the efficacy of the liposomal SNAs were identified. The quantity of MPLA feed into the liposomal formulation step might play a role, as well as the internucleotide linkage chemistry (PO vs PS). Accordingly, liposomal SNAs were developed with increasing MPLA feed from 3.8% (w/w) to 11.5% (w/w) and constructs containing both PO and PS linkages and tested them for activity in RAW Blue cells. In this cell line, it was observed that increasing the MPLA feed up to 7.7% MPLA but not up to 11.5% increased the potency of activation of the liposomal SNA (FIG. 8). In the RAW Blue cells, a shift was observed in the potency of the liposomal SNA but not in the maximal stimulation (FIG. 9), though this is anticipated to be species dependent.

Finally, the ability of antigen-conjugated liposomal SNAs to activate immune cells was tested. Ovalbumin loaded liposomal SNAs were incubated as described with RAW Blue cells overnight at the level of SEAP probed by QuantiBlue assay. Conjugation of antigen to the liposomal SNAs appeared to increase their activity (FIG. 10). It is possible that this occurs due to the presence of additional CpG motifs introduced by the complementary oligonucleotide that is attached to the ovalbumin, which formed duplexes with CpG 1826.

In Vivo Testing

This form of antigen delivery has been shown to induce more potent induction of immune stimulatory effects in vitro (FIG. 10) and induce effective antigen processing and presentation, leading to effective induction of an anti-tumor immune response in vivo (FIGS. 11-12).

C57BL/6 mice (N=4/group) were immunized (2000 μL s.c., 100 μg ovalbumin equivalent dose) with the indicated formulations on day 0 and 21 using ovalbumin as the model antigen (FIG. 11). On day 28, splenocytes were collected and incubated overnight on IFN-γ ELISPOT plates with 1 uM OVA(257-264). The number of IFN-γ spots was quantified using an automated ELISPOT counter. This study shows that SNAs induce cellular responses more effectively than free PS oligo and alum. *p<0.05, NS=non-significant.

In another experiment, C57BL/6 mice (N=11/group) were inoculated with $1 \times 10^6$ E.G7-OVA cells (ATCC #CRL-2113) on day 0 then treated with the indicated compounds on days 3, 7, 10 (2000 μL s.c., 100 μg ovalbumin equivalent dose). Tumor volume was calculated by measuring the length and width of the subcutaneous tumor and applying the formula tumor volume=(length)×(width)×(width)/2. The results demonstrate activation of strong cellular responses to antigen in vivo with evidence of significant (95%) reduction of tumor burden (FIG. 12).

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one or all of the group members are present in, employed in or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A nanostructure, comprising:
   a liposomal core having a lipid bilayer and an oligonucleotide shell oriented radially outwards positioned on the exterior of the liposomal core,
   wherein an antigen is encapsulated within the liposomal core,
   wherein the oligonucleotide shell comprises at least one CpG-motif containing oligonucleotide, and
   wherein the CpG-motif containing oligonucleotide is indirectly linked to the liposomal core through a lipid anchor.

2. The nanostructure of claim 1, wherein the oligonucleotide shell further comprises a double-stranded DNA oligonucleotide, single-stranded RNA oligonucleotide, double-stranded RNA oligonucleotide, chimeric RNA-DNA oligonucleotide, or combinations of single-stranded DNA oligonucleotide, double-stranded DNA oligonucleotide, single-stranded RNA oligonucleotide, double-stranded RNA oligonucleotide, or chimeric RNA-DNA oligonucleotides.

3. The nanostructure of claim 1, wherein the oligonucleotide shell further comprises at least one non-CpG-motif containing oligonucleotide.

4. The nanostructure of claim 1, wherein at least one CpG-motif containing oligonucleotide in the oligonucleotide shell has its 5'-terminus exposed to the outside surface of the nanostructure or all of the oligonucleotides in the oligonucleotide shell have their 5'-terminus exposed to the outside surface of the nanostructure.

5. The nanostructure of claim 1, wherein the oligonucleotide shell comprises at least 25 oligonucleotides.

6. The nanostructure of claim 1, wherein the oligonucleotide shell comprises 50-300 oligonucleotides.

7. The nanostructure of claim 1, wherein the CpG-motif containing oligonucleotide comprises or consists of a sequence of SEQ ID NO: 1 or SEQ ID NO: 21.

8. The nanostructure of claim 1, wherein the lipid anchor is cholesterol.

9. The nanostructure of claim 1, wherein the liposomal core is comprised of phospholipids.

10. The nanostructure of claim 1, wherein the liposomal core is comprised of 1,2-dioleoyl-sn-glycero-3-phosphatidylcholine (DOPC).

11. The nanostructure of claim 1, wherein the nanostructure further comprises an additional antigen.

12. The nanostructure of claim 11, wherein the additional antigen is directly linked to an oligonucleotide of the oligonucleotide shell or to the liposomal core.

13. The nanostructure of claim 11, wherein the additional antigen is indirectly linked to an oligonucleotide of the oligonucleotide shell or to the liposomal core through a lipid anchor.

14. The nanostructure of claim 11, wherein the additional antigen is attached to an oligonucleotide to form an antigen-oligonucleotide conjugate, and wherein the oligonucleotide is hybridized to the CpG-motif containing oligonucleotide.

15. The nanostructure of claim 11, wherein the additional antigen is selected from the group consisting of a cancer antigen, a bacterial antigen, a viral antigen, a parasitic antigen, a hapten, and an allergen.

16. The nanostructure of claim 1, wherein the antigen is selected from the group consisting of a cancer antigen, a bacterial antigen, a viral antigen, a parasitic antigen, a hapten, and an allergen.

17. The nanostructure of claim 16, wherein the cancer antigen is associated with a cancer selected from the group consisting of biliary tract cancer, brain cancer, breast cancer, cervical cancer, choriocarcinoma, colon cancer, endometrial cancer, esophageal cancer, gastric cancer, lymphoma, liver cancer, lung cancer, skin cancer, oral cancer, ovarian cancer, pancreas cancer, prostate cancer, rectal cancer testicular cancer, thyroid cancer and renal cancer.

18. The nanostructure of claim 16, wherein the cancer antigen is associated with a cancer selected from the group consisting of small cell lung cancer, non-small cell lung cancer, melanoma, hairy cell leukemia, chronic myelogenous leukemia, cutaneous T-cell leukemia, multiple myeloma, follicular lymphoma, squamous cell carcinoma and bladder cell carcinoma.

19. A method for treating a disorder in a subject, comprising
   administering to a subject the nanostructure of claim 1 in an effective amount to promote an immune response in the subject to treat the disorder.

20. The method of claim 19, wherein the disorder is cancer, infectious disease, a viral infection, a bacterial infection, allergy, asthma, or autoimmune disease.

* * * * *

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
tccatgacgt tcctgacgtt                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
aacgtcagga acgtcatgga                           20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
tccatgagct tcctgagctt                           20

<210> SEQ ID NO 4
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 4
ccgucuguug ugugacuc                             18

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
ggtgcatcga tgcaggggggg                          20

<210> SEQ ID NO 6
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 6
gccaccgagc cgaaggcacc                           20

<210> SEQ ID NO 7
<211> LENGTH: 20
<212> TYPE: RNA
<213> ORGANISM: Artificial Sequence

```
<220> FEATURE:
<223> OTHER INFORMATION: Synthetic Polynucleotide

<400> SEQUENCE: 7
uauauauaua uauauauaua                                            20

<210> SEQ ID NO 8
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 8
uuauuauuau uauuauuauu                                            20

<210> SEQ ID NO 9
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 9
uuuuauuuua uuuuauuuua                                            20

<210> SEQ ID NO 10
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 10
ugugugugug ugugugugug                                            20

<210> SEQ ID NO 11
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 11
uuguuguugu uguuguuguu                                            20

<210> SEQ ID NO 12
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 12
uuuguuuguu uguuuguuug                                            20

<210> SEQ ID NO 13
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 13
uuauuuauuu auuuauuuau uuau                                       24
```

```
<210> SEQ ID NO 14
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 14
uuguuuguuu guuuguuugu uugu                                              24

<210> SEQ ID NO 15
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 15
gcccgucugu ugugugacuc                                                   20

<210> SEQ ID NO 16
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 16
guccuucaag uccuucaa                                                     18

<210> SEQ ID NO 17
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 17
tccatggacg ttcctgagcg tt                                                22

<210> SEQ ID NO 18
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 18
tcgtcgttcg aacgacgttg at                                                22

<210> SEQ ID NO 19
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 19
tcgtcgacga tccgcgcgcg cg                                                22

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 20
ggggtcaacg ttgaggggggg                                            20

<210> SEQ ID NO 21
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 21
tcgtcgtttt gtcgttttgt cgtt                                        24

<210> SEQ ID NO 22
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 22
tcgtcgttgt cgttttgtcg tt                                          22

<210> SEQ ID NO 23
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 23
gggggacgat cgtcggggggg                                            20

<210> SEQ ID NO 24
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 24
ggggacgacg tcgtggggggg g                                          21

<210> SEQ ID NO 25
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 25
tcgtcgtttt cggcgcgcgc cg                                          22

<210> SEQ ID NO 26
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 26
tcgtcgtcgt tcgaacgacg ttgat                                       25
```